US008349556B2

(12) United States Patent
Kutyavin

(10) Patent No.: US 8,349,556 B2
(45) Date of Patent: Jan. 8, 2013

(54) USE OF BASE-MODIFIED DEOXYNUCLEOSIDE TRIPHOSPHATES TO IMPROVE NUCLEIC ACID DETECTION

(76) Inventor: Igor Kutyavin, Woodinville, WA (US)

( * ) Notice: Subject to any disclaimer, the term of this patent is extended or adjusted under 35 U.S.C. 154(b) by 725 days.

(21) Appl. No.: 12/298,895

(22) PCT Filed: Apr. 30, 2007

(86) PCT No.: PCT/US2007/067826
§ 371 (c)(1),
(2), (4) Date: Aug. 12, 2009

(87) PCT Pub. No.: WO2007/127992
PCT Pub. Date: Nov. 8, 2007

(65) Prior Publication Data
US 2010/0151455 A1    Jun. 17, 2010

Related U.S. Application Data

(60) Provisional application No. 60/795,705, filed on Apr. 28, 2006, provisional application No. 60/849,526, filed on Oct. 4, 2006.

(51) Int. Cl.
*C12Q 1/68* (2006.01)
*C12P 19/34* (2006.01)
*C07H 21/02* (2006.01)
*C07H 19/34* (2006.01)
*G01N 15/06* (2006.01)
*G01N 31/00* (2006.01)

(52) U.S. Cl. ...... 435/6.1; 435/91.1; 435/91.2; 536/23.1; 536/24.3; 536/26.6; 422/430; 422/68.1

(58) Field of Classification Search .................. 435/6.1, 435/91.1, 91.2; 536/23.1, 24.3, 26.6; 422/430, 422/68.1
See application file for complete search history.

(56) References Cited

U.S. PATENT DOCUMENTS 4,458,066 A    7/1984    Caruthers et al.
(Continued)

FOREIGN PATENT DOCUMENTS

WO    WO 99/009213    2/1999
(Continued)

OTHER PUBLICATIONS

Seela et al. Bioorganic & Medicinal Chemistry Letters 10, 2000, 289-292.*
(Continued)

*Primary Examiner* — Jezia Riley
(74) *Attorney, Agent, or Firm* — Barry L. Davidson; Davis Wright Tremaine LLP

(57) ABSTRACT

Aspects of the invention provide novel and surprisingly effective methods for the detection of nucleic acids, comprising nucleic acid amplification using base-modified deoxynucleoside 5'-triphosphates (dNTPs). Particular aspects relate to methods for enhancing hybridization properties of oligonucleotide primers and probes in assays detecting nucleic acids, comprise amplifying target DNAs in presence of base-modified duplex-stabilizing deoxyribonucleoside 5'-triphosphates to provide for modified target DNAs, and thereby considerably improving performance of the detection assays. The disclosed methods allow for increasing of the reaction temperature in PCR-based detection systems or, alternatively, reducing the length of the oligonucleotide primers and probes. Certain aspects relates to improvement of real time PCR assays, wherein nucleic acids of interest are detected as the reaction proceeds using fluorescent agents or oligonucleotide FRET probes.

57 Claims, 11 Drawing Sheets

U.S. PATENT DOCUMENTS

| | | | |
|---|---|---|---|
| 4,683,195 | A | 7/1987 | Mullis et al. |
| 4,683,202 | A | 7/1987 | Mullis |
| 5,168,038 | A | 12/1992 | Tecott et al. |
| 5,210,015 | A | 5/1993 | Gelfand et al. |
| 5,234,809 | A | 8/1993 | Boom et al. |
| 5,270,184 | A | 12/1993 | Walker et al. |
| 5,418,149 | A | 5/1995 | Gelfand et al. |
| 5,691,142 | A | 11/1997 | Dahlberg et al. |
| 5,723,591 | A | 3/1998 | Livak et al. |
| 5,824,517 | A | 10/1998 | Cleuziat et al. |
| 5,837,450 | A | 11/1998 | Dahlberg et al. |
| 5,846,717 | A | 12/1998 | Brow et al. |
| 5,854,033 | A | 12/1998 | Lizardi |
| 5,925,517 | A | 7/1999 | Tyagi et al. |
| 5,985,557 | A | 11/1999 | Prudent et al. |
| 5,994,069 | A | 11/1999 | Hall et al. |
| 6,001,567 | A | 12/1999 | Brow et al. |
| 6,063,603 | A | 5/2000 | Davey et al. |
| 6,090,543 | A | 7/2000 | Prudent et al. |
| 6,174,670 | B1 | 1/2001 | Wittwer et al. |
| 6,214,587 | B1 | 4/2001 | Dattagupta et al. |
| 6,251,639 | B1 | 6/2001 | Kurn |
| 6,348,314 | B1 | 2/2002 | Prudent et al. |
| 6,410,278 | B1 | 6/2002 | Notomi et al. |
| 6,569,627 | B2 | 5/2003 | Wittwer et al. |
| 6,589,743 | B2 | 7/2003 | Sorge |
| 6,808,897 | B2 | 10/2004 | Shaw et al. |
| 6,875,572 | B2 | 4/2005 | Prudent et al. |
| 6,902,914 | B2 | 6/2005 | Ward et al. |
| 6,913,881 | B1 | 7/2005 | Aizenstein et al. |
| 7,252,940 | B2 | 8/2007 | Kutyavin et al. |
| 2003/0224359 | A1 | 12/2003 | Dempcy et al. |

FOREIGN PATENT DOCUMENTS

| | | |
|---|---|---|
| WO | WO 00/075371 | 12/2000 |
| WO | WO 2007/127992 | 11/2007 |

OTHER PUBLICATIONS

U.S. Appl. No. 60/795,705, filed Apr. 28, 2006, Kutyavin.
U.S. Appl. No. 60/849,526, filed Oct. 4, 2006, Kutyavin.
Afonina et al., "Efficient priming of PCR with short oligonucleotides conjugated to a minor groove binder," Nucleic Acids Research, 1997, pp. 2657-2660, vol. 25.
Afonina et al., "Minor Groove Binder-Conjugated DNA Probes for Quantitative DNA Detection by Hybridization-Triggered Fluorescence," BioTechniques, 2002, pp. 940-949, vol. 32.
Afonina et al., "Single Nucleotide Polymorphism Detection with MGB Eclipse™ Assays," Journal of Clinical Ligand Assays, 2002, pp. 268-275, vol. 25.
An et al., "Characterization of a Thermostable UvrD Helicase and Its Participation in Helicase-dependant Amplification," The Journal of Biological Chemistry, 2005, pp. 28952-28958, vol. 280.
Andras et al., "Strategies for Signal Amplification in Nucleic Acid Detection," Molecular Biotechnology, 2001, pp. 29-44, vol. 19.
Auer et al., "Selective amplification of RNA utilizing the nucleotide analog dITP and *Thermus thermophilus* DNA polymerase," Nucleic Acids Research, 1996, pp. 5021-5025, vol. 24.
Bailly et al., "Binding of Daunomycin to Diaminopurine- and/or Inosine-Substituted DNA," Biochemistry, 1998, pp. 1033-1045, vol. 37.
Bailly et al., "Transferring the purine 2-amino group from guanines to adenines in DNA changes the sequence-specific binding of antibiotics," Nucleic Acids Research, 1995, pp. 885-892, vol. 23.
Bailly et al., "The use of diaminopurine to investigate structural properties of nucleic acids and molecular recognition between ligands and DNA," Nucleic Acids Research, 1998, pp. 4309-4314, vol. 26.
Beaucage et al., "Deoxynucleoside Phosphoramidites—A New Class of Key Intermediates for Deoxypolynucleotide Synthesis," Tetrahedron Letters, 1981, pp. 1859-1862, vol. 22.
Becker-Andre, "Absolute mRNA quantification using the polymerase chain reaction (PCR). A novel approach by a PCR aided transcript titration assay (PATTY)," Nucleic Acids Research, 1989, pp. 9437-9446, vol. 17.
Bedinger et al., "Sequence-specific Pausing during in Vitro DNA Replication on Double-stranded DNA Templates," The Journal of Biological Chemistry, 1989, pp. 16880-16886, vol. 264.
Belyavsky et al., "PCR-based cDNA library construction: general cDNA libraries at the level of a few cells," Nucleic Acids Research, 1989, pp. 2919-2932, vol. 17.
Bierne et al., "When replication forks stop," Molecular Microbiology, 1994, pp. 17-23, vol. 13.
Bonnet et al., "Thermodynamic basis of the enhanced specificity of structured DNA probes," The Proceedings of the National Academy of Sciences, 1999, pp. 6171-6176, vol. 96.
Breslauer et al., "Predicting DNA duplex stability from the base sequence," The Proceedings of the National Academy of Sciences, 1986, pp. 3746-3750, vol. 83.
Brown et al., "Chemical Synthesis and Cloning of a Tyrosine tRNA Gene," Methods in Enzymology, 1979, pp. 109-151, vol. 68.
Burgner et al., "Improved Allelic Differentiation Using Sequence-Specific Oligonucleotide Hybridization Incorporating an Additional Base-Analogue Mismatch," Nucleosides, Nucleotides & Nucleic Acids, 2004, pp. 755-765, vol. 23.
Butkus et al., "Synthesis and physical characterization of DNA fragments containing N4-methytcytosine and 5-methylcytosine," Nucleic Acids Research, 1987, pp. 8467-8478, vol. 15.
Cardullo et al., "Detection of nucleic acid hybridization by nonradiative fluorescence resonance energy transfer," The Proceedings of the National Academy of Sciences, 1988, pp. 8790-8794, vol. 85.
Clegg et al., "Fluorescence resonance energy transfer," Current Opinion in Biotechnology, 1995, pp. 103-110, vol. 6.
Clegg et al., "Fluorescence Resonance Energy Transfer and Nucleic Acids," Methods in Enzymology, 1992, pp. 353-388, vol. 211.
Clementi et al., "Quantitative PCR and RT-PCR in Virology," PCR Methods and Applications, 1993, pp. 191-196, vol. 2.
Demple et al., "Exonuclease III and endonuclease IV remove 3' blocks from DNA synthesis primers in $H_2O_2$-damaged *Escherichia coli*," The Proceedings of the National Academy of Sciences, 1986, pp. 7731-7735, vol. 83.
Didenko et al., "DNA Probes Using Fluorescence Resonance Energy Transfer (FRET): Designs and Applications," Biotechniques, 2001, pp. 1106-1121, vol. 31.
Dierick et al., "Incorporation of dITP or 7-deaza dGTP during PCR improves sequencing of the product," Nucleic Acids Research, 1993, pp. 4427-4428, vol. 21.
Di Giusto et al., "Strong positional preference in the interaction of LNA oligonucleotides with DNA polymerase and proofreading exonuclease activities: implications for genotyping assays," Nucleic Acids Research, 2004, p. e32, vol. 32 (8 pages).
Diviacco et al., "A novel procedure for quantitative polymerase chain reaction by coamplification of competitive templates," Gene, 1992, pp. 313-320, vol. 122.
Dobrikov et al., "Incorporation of (α-P-Borano)-2',3'-dideoxycytidine 5'-Triphosphate into DNA by Drug-Resistant MMLV Reverse Transcriptase and Taq DNA Polymerase," Nucleosides, Nucleotides & Nucleic Acids, 2003, pp. 1651-1655, vol. 22.
Doty et al., Strand Separation and Specific Recombination in Deoxyribonucleic Acids: Physical Chemical Studies, The Proceedings of the National Academy of Science, 1960, pp. 461-476, vol. 46.
Fong et al., "Rapid Solid-Phase Immunoassay for Detection of Methicillin-Resistant *Staphylococcus aureus* Using Cycling Probe Technology," Journal of Clinical Microbiology, 2000, pp. 2525-2529, vol. 38.
Freeman et al., "Quantitative RT-PCR: Pitfalls and Potential," BioTechniques, 1999, pp. 112-125, vol. 26.
Gaffney et al., "The Influence of the Purine 2-Amino Group on DNA Conformation and Stability—II," Tetrahedron, 1984, pp. 3-13, vol. 40.
Goldenberg et al., "Use of locked nucleic acid oligonucleotides as hybridization/FRET probes for quantification of 16S rDNA by real-time PCR," BioTechniques, 2005, pp. 29-32, vol. 38
Gourlain et al., "Enhancing the catalytic repertoire of nucleic acids. II. Simultaneous incorporation of amino and imidazolyl functionalities by two modified triphosphates during PCR," Nucleic Acids Research, 2001, pp. 1898-1905, vol. 29.

Gu et al., "Multiplexed, Real-Time PCR for Quantitative Detection of Human Adenovirus," Journal of Clinical Microbiology, 2003, pp. 4636-4641, vol. 41.

Gundry et al., "Rapid F508del and F508C Assay Using Fluorescent Hybridization Probes," Genetic Testing, 1999, pp. 365-370, vol. 3.

Hacia et al., "Enhanced high density oligonucleotide array-based sequence analysis using modified nucleoside triphosphates," Nucleic Acids Research, 1998, pp. 4975-4982, vol. 26.

Hafner et al., "Isothermal Amplification and Multimerization of DNA by Bst DNA Polymerase," BioTechniques, 2001, pp. 852-867, vol. 30.

Harvey et al., "Characterization and applications of CataCleave probe in real-time detection assays," Analytical Biochemistry, 2004, pp. 246-255, vol. 333.

Held et al., "Challenging artificial genetic systems: thymidine analogs with 5-position sulfur functionality," Nucleic Acids Research, 2002, pp. 3857-3869, vol. 30.

Higuchi et al., "Kinetic PCR Analysis: Real-time Monitoring of DNA Amplification Reactions," Bio/Technology, 1993, pp. 1026-1030, vol. 11.

Higuchi et al., "Simultaneous Amplification and Detection of Specific DNA Sequences," Bio/Technology, 1992, pp.413-417, vol. 10.

Howard et al., "$2NH_2A \cdot T$ Helices in the Ribo- and Deoxypolynucleotide Series. Structural and Energetic Consequences of $2NH_2A$ Substitution," Biochemistry, 1984, pp. 6723-6732, vol. 23.

Howard et al., "A New Polynucleotide Complex Stabilized by Three Interbase Hydrogen Bonds, Poly-2-aminoadenylic Acid + Polytiridylic Acid," Journal of Biological Chemistry, 1966, pp. 4293-4295, vol. 241.

Howard et al., "Poly(2-aminoadenylic acid): Interaction with Poly(uridylic acid)," Biochemistry, 1976, pp. 3783-3795, vol. 15.

Innis et al., "DNA sequencing with *Thermus aquaticus* DNA polymerase and direct sequencing of polymerase chain reaction-amplified DNA," The Proceedings of the National Academy of Sciences, 1988, pp. 9436-9440, vol. 85.

Jaeger et al., "Generation and Enzymatic Amplification of High-Density Functionalized DNA Double Strands," Angewandte Chemie, 2004, pp. 3337-3340, vol. 43.

Johnson et al., "Locked nucleic acid (LNA) single nucleotide polymorphism (SNP) genotype analysis and validation using real-time PCR," Nucleic Acids Research, 2004, p. e55, vol. 32 (9 pages).

Kempeneers et al., "Investigation of the DNA-dependent cyclohexenyl nucleic acid polymerization and the cyclohexenyl nucleic acid-dependent DNA polymerization," Nucleic Acids Research, 2005, pp. 3828-3836, vol. 33.

Kutyavin et al., "3'-Minor groove binder-DNA probes increase sequence specificity at PCT extension temperatures," Nucleic Acids Research, 2000, pp. 655-661, vol. 28.

Kutyavin et al., "Oligonucleotides Containing 2-Aminoadenine and 2-Thiothymine Act as Selectively Binding Complementary Agents," Biochemistry, 1996, pp. 11170-11176, vol. 35.

Kutyavin et al., "Oligonucleotides with conjugated dihydropyrroloindole tripeptides: base composition and backbone effects on hybridization," Nucleic Acids Research, 1997, pp. 3718-3723, vol. 25.

Kutyavin et al., "Use of Base-Modified Duplex-Stabilizing Deoxynudeoside 5'-Triphosphates to Enhance the Hybridization Properties of Primers and Probes in Detection Polymerase Chain Reaction," Biochemistry, 2008, pp. 13666-13673, vol. 47.

Kuwahara et al., "Comparison study on PCR amplification of modified DNA by using various kinds of polymerase and modified nucleoside triphosphates," Nucleic Acids Symposium Series No. 49, 2005, pp. 275-276.

Kuwahara et al., "Enzymatic incorporation of chemically-modified nucleotides into DNAs," Nucleic Acids Research Supplement No. 2, 2002, pp. 83-84.

Kuwahara et al., "Simultaneous incorporation of three different modified nucleotides during PCR," Nucleic Acids Research Supplement No. 3, 2003 pp. 37-38.

Kuwahara et al., "Substrate Properties of C5-Substituted Pyrimidine 2'-Deoxynudeoside 5'-Triphosphates for Thermostable DNA Polymerases During PCR," Bioorganic & Medicinal Chemistry Letters, 2003, pp. 3735-3738, vol. 13.

Laduca et al., "Site-Specific Pausing of Deoxyribonucleic Acid Synthesis Catalyzed by Four Forms of *Escherichia coli* DNA Polymerase III," Biochemistry, 1983, pp. 5177-5188, vol. 22.

Latorra et al., "Design considerations and effects of LNA in PCR primers," Molecular and Cellular Probes, 2003, pp. 253-259, vol. 17.

Latorra et al., "Enhanced Allele-Specific PCR Discrimination in SNP Genotyping Using 3' Locked Nucleic Acid (LNA) Primers," Human Mutation, 2003, pp. 79-85, vol. 22.

Lebedev et al., "Oligonucleotides containing 2-aminoadenine and 5-methylcytosine are more effective as primers for PCR amplification than their nonmodified counterparts," Genetic Analysis: Biomolecular Engineering, 1996, pp. 15-21, vol. 13.

Lee et al., "Enhancing the catalytic repertoire of nucleic acids: a systematic study of linker length and rigidity," Nucleic Acids Research, 2001, pp. 1565-1573, vol. 29.

Lewin et al., "Use of Real-Time PCR and Molecular Beacons to Detect Virus Replication in Human Immunodeficiency Virus Type 1-Infected Individuals on Prolonged Effective Antiretroviral Therapy," Journal of Virology, 1999, pp. 6099-6103, vol. 73.

Lie et al., "Advances in quantitative PCR technology: 5' nuclease assays," Current Opinion in Biotechnology, 1998, pp. 43-48, vol. 9.

Livak et al., "Oligonucleotides with Fluorescent Dyes at Opposite Ends Provide a Quenched Probe System Useful for Detecting PCR Product and Nucleic Acid Hybridization," PCR Methods and Applications, 1995, pp. 357-362, vol. 4.

Lutfalla et al., "Performing Quantitative Reverse-Transcribed Polymerase Chain Reaction Experiments," Methods in Enzymology, 2006, pp. 386-400, vol. 410.

Mackay et al., "Real-Time PCR Fluorescent Chemistries," Methods in Molecular Biology, 2007, pp. 237-262, vol. 353.

Mackay et al., "Real-Time PCR in virology," Nucleic Acids Research, 2002, pp. 1292-1305, vol. 30.

Marmur et al., "Strand Separation and Specific Recombination in Deoxyribonucleic Acids: Biological Studies," The Proceedings of the National Academy of Sciences, 1960, pp. 453-461, vol. 46.

Marras et al., "Efficiencies of fluorescence resonance energy transfer and contact-mediated quenching in oligonucleotide probes," Nucleic Acids Research, 2002, p. e122, vol. 30 (8 pages).

Masud et al., "Enzymatic synthesis of modified DNA by PCR," Nucleic Acids Research Supplement No. 1, 2001, pp. 21-22.

Masud et al., "Modified DNA Bearing 5-(Methoxycarbonyl-methyl)-2'-deoxyuridine: Preparation by PCR with Thermophilic DNA Polymerase and Post-synthetic Derivatization," ChemBioChem, 2003, pp. 584-588, vol. 4.

Matthes et al., "Comparative Inhibition of Hepatitis B Virus DNA Polymerase and Cellular DNA Polymerases by Triphosphates of Sugar-Modified 5-Methyldeoxycytidines and of Other Nucleoside Analogs," Antimicrobial Agents and Chemotherapy, 1991, pp. 1254-1257, vol. 35.

Miller et al., "A simple salting out procedure for extracting DNA from human nucleated cells," Nucleic Acids Research, 1988, p. 1215, vol. 16.

Narang et al, "Improved Phosphotriester Method for the Synthesis of Gene Fragments," Methods in Enzymology, 1979, pp. 90-98, vol. 68.

Nazarenko et al., "Effect of primary and secondary structure of oligodeoxyribonucleotides on the fluorescent properties of conjugated dyes," Nucleic Acids Research, 2002, pp. 2089-2095, vol. 30.

Nazarenko et al., "Multiplex quantitative PCR using self-quenched primers labeled with a single fluorophore," Nucleic Acids Research, 2002, p. e37, vol. 30 (7 pages).

Nguyen et al., "Quantitative assessment of the use of modified nucleoside triphosphates in expression profiling: differential effects on signal intensities and impacts on expression ratios," BMC Biotechnology, 2002, p. 14, vol. 2 (15 pages).

Niesters, "Quantitation of Viral Load Using Real-Time Amplification Techniques," Methods, 2001, pp. 419-429, vol. 25.

Notomi et al., "Loop-mediated isothermal amplification of DNA," Nucleic Acids Research, 2000, p. e63, vol. 28 (7 pages).

Oehlenschläger et al., "Detection of HIV-1 RNA by nucleic acid sequence-based amplification combined with fluorescence correlation spectroscopy," The Proceedings of the National Academy of Sciences, 1996, pp. 12811-12816, vol. 93.

Ohbayashi et al., "Expansion of repertoire of modified DNAs prepared by PCR using KOD Dash DNA polymerase," Organic & Biomolecular Chemistry, 2005, pp. 2463-2468, vol. 3.

Ono et al., "2'-Fluro modified nucleic adds: polymerase-directed synthesis, properties and stability to analysis by matrix-assisted laser desorption/ionization mass spectrometry," Nucleic Acids Research, 1997, pp. 4581-4588, vol. 25.

Ono et al., "Synthesis of decadeoxyribonucleotides containing $N^6$-methylcytosine, and 5'-methylcytosine: recognition and cleavage by restriction endonucleases (nucleosides and nucleotides part 74)," Nucleic Acids Research, 1987, pp. 219-232, vol. 15.

Ortiz et al., "PNA molecular beacons for rapid detection of PCR amplicons," Molecular and Cellular Probes, 1998, pp. 219-226, vol. 12.

Piatek et al., "Molecular beacon sequence analysis for detecting drug resistance in *Mycobacterium tuberculosis*," Nature Biotechnology, 1998, pp. 359-363, vol. 16.

Porter et al., "Direct PCR sequencing with bomated nucleotides," Nucleic Acids Research, 1997, pp. 1611-1617, vol. 25.

Prosnyak et al., "Substitution of 2-Aminoadenine and 5-Methylcytosine for Adenine and Cytosine in Hybridization Probes Increases the Sensitivity of DNA Fingerprinting," Genomics, 1994, pp. 490-494, vol. 21.

Reid et al., "Insertion and Extension of Acyclic, Dideoxy, and Ara Nucleotides by Herpesviridae, Human α and Human β Polymerases," The Journal of Biological Chemistry, 1988, pp. 3898-3904, vol. 263.

Robelek et al., "Multiplexed Hybridization Detection of Quantum Dot-Conjugated DNA Sequences Using Surface Plasmon Enhanced Fluorescence Microscopy and Spectrometry," Analytical Chemistry, 2004, pp. 6160-6165, vol. 76.

Santalucia, "A unified view of polymer, dumbbell, and oligonucleotide DNA nearest-neighbor thermodynamics," The Proceedings of the National Academy of Sciences, 1998, pp. 1460-1465, vol. 95.

Sawai et al., "Synthesis of New Modified DNAs by Hyperthermophilic DNA Polymerase: Substrate and Template Specificity of Functionalized Thymidine Analogues Bearing an sp3-Hybridized Carbon at the C5 α-Position for Several DNA Polymerases," Bioconjugate Chemistry, 2002, pp. 309-316, vol. 13.

Scheit et al., "Synthesis and physiochemical properties of two analogs of poly(dA): poly(2-aminopurine-9-β-D-deoxyribonucleotide) and poly 2-amino-deoxyadenylic acid," Nucleic Acids Research, 1982, pp. 4059-4069, vol. 10.

Schneeberger et al., "Quantitative Detection of Reverse Transcriptase-PCR Products by Means of a Novel and Sensitive DNA Stain," PCR Methods and Applications, 1995, pp. 234-238, vol. 4.

Schweitzer et al., "Combining nucleic acid amplification and detection," Current Opinion in Biotechnology, 2001, pp. 21-27, vol. 12.

Seela et al., "7-Deazapurine containing DNA: efficiency of $c^7G_d$ TP, $c^7 A_d$TP and $c^7 I_d$TP incorporation during PCR-amplification and protection from endodeoxyribonuclease hydrolysis," Nucleic Acids Research, 1992, pp. 55-61, vol. 20.

Selvin, "Fluorescence Resonance Energy Transfer," Methods in Enzymology, 1995, pp. 300-334, vol. 246.

Simeonov et al., "Single nucleotide polymorphism genotyping using short, fluorescently labeled locked nucleic acid (LNA) probes and fluorescence polarization detection," Nucleic Acids Research, 2002, p. e91, vol. 30 (5 pages).

Simpson et al., "A Method for Specific Cloning and Sequencing of Human HPRT cDNA for Mutation Analysis," Biochemical and Biophysical Research Communications, 1988, pp. 487-492, vol. 151.

Spargo et al., "Detection of *M. tuberculosis* DNA using Thermophilic Strand Displacement Amplification," Molecular and Cellular Probes, 1996, pp. 247-256, vol. 10.

Strauss et al., "Substrate Binding by Human Apurinic/Apyrimidinic Endonuclease Indicates a Briggs-Haldane Mechanism," The Journal of Biological Chemistry, 1997, pp. 1302-1307, vol. 272.

Stryer et al., "Energy Transfer: A Spectroscopic Ruler," The Proceedings of the National Academy of Sciences, 1967, pp. 719-726, vol. 58.

Summers et al., "Boranophosphates as Mimics of Natural Phosphodiesters in DNA," Current Medicinal Chemistry, 2001, pp. 1147-1155, vol. 8.

Szer, "Secondary Structure of Poly-5-Methylcytidylic Acid," Biochemical and Biophysical Research Communications, 1965, pp. 182-186, vol. 20.

Szer et al., "The Structure of Poly-5-methylcytidylic Acid and its Twin-stranded Complex with Poly-inosinic Acid," Journal of Molecular Biology, 1966, pp. 174-187, vol. 17.

Takagi et al., "Characterization of DNA Polymerase from *Pyrococcus sp.* Strain KOD1 and Its Application to PCR," Applied and Environmental Microbiology, 1997, pp. 4504-4510, vol. 63.

Thelwell et al., "Mode of action and application of Scorpion primers to mutation detection," Nucleic Acids Research, 2000, pp. 3752-3761, vol. 28.

Timofeev et al., "Binding specificity and stability of duplexes formed by modified oligonucleotides with a 4096-hexanucleotide microarray," Nucleic Acids Research, 2001, pp. 2626-2634, vol. 29.

Tyagi et al., "Molecular Beacons: Probes that Fluoresce upon Hybridization," Nature Biotechnology, 1996, pp. 303-308, vol. 14.

Tyagi et al, "Wavelength-shifting molecular beacons," Nature Biotechnology, 2000, pp. 1191-1196, vol. 18.

Uesugi et al., "Synthesis and Properties of d(ATACGCGTAT) and Its Derivatives Containing One and Two 5-Methylcytosine Residues. Effect of the Methylation on Deoxyribunucleic Acid Conformation," Chemical Pharmaceutical Bulletin, 1986, pp. 51-60, vol. 34.

Vincent et al., "Helicase-dependant isothermal DNA amplification," EMBO Reports, 2004, pp. 795-800, vol. 5.

Walker et al., "DNA detection by strand displacement amplification and fluorescence polarization with signal enhancement using DNA binding protein," Nucleic Acids Research, 1996, pp. 348-353, vol. 24.

Walker et al., "Isothermal in vitro amplification of DNA by a restriction enzyme/DNA polymerase system," The Proceedings of the National Academy of Sciences, 1992, pp. 392-396, vol. 89.

Walsh et al., "Chelex® 100 as a Medium for Simple Extraction of DNA for PCR-Based Typing from Forensic Material," 1991, BioTechniques, pp. 506-513, vol. 10.

Wang et al., "The Effect of a Single Boranophosphate Substitution with Defined Configuration on the Thermal Stability and Conformation of a DNA Duplex," Nucleosides, Nucleotides, and Nucleic Acids, 2005, pp. 951-955, vol. 24.

Whitcombe et al., "Detection of PCR products using self-probing amplicons and fluorescence," Nature Biotechnology, 1999, pp. 804-807, vol. 17.

Wilson et al., "Abasic site binding by the human apurinic endonuclease, Ape, and determination of the DNA contact sites," Nucleic Acids Research, 1997, pp. 933-939, vol. 25.

Wong et al., "PCR with 5-methyl-dCTP replacing dCTP," Nucleic Acids Research, 1991, pp. 1081-1085, vol. 19.

Yi et al., "Molecular Zipper: a fluorescent probe for real-time isothermal DNA amplification," Nucleic Acids Research, 2006, p. e81, vol. 34 (5 pages).

You et al., "Design of LNA probes that improve mismatch discrimination," Nucleic Acids Research, 2006, p. e60, vol. 34 (11 pages).

Baner et al., "Signal amplification of padlock probes by rolling circle replication," Nucleic Acids Research, 1998, pp. 5073-5078, vol. 26.

Modrusan et al., "CPT-EIA assays for the detection of vancomycin resistant vanA and vanB genes in *Enterococci*," Diagnostic Microbiology and Infectious Disease, 2000, pp. 45-50, vol. 37.

* cited by examiner

USE OF BASE-MODIFIED DEOXYNUCLEOSIDE TRIPHOSPHATES TO IMPROVE NUCLEIC ACID DETECTION

CROSS-REFERENCE TO RELATED APPLICATIONS

This application is the United States nationalization, under 35 U.S.C. §371, of International Application No. PCT/US2007/067826, filed 30 Apr. 2007, which claims the benefit of priority to U.S. Provisional Patent Application Ser. Nos. 60/795,705 filed Apr. 28, 2006, and 60/849,526 filed 4 Oct. 2006, all of which are incorporated by reference herein in their entirety.

FIELD OF THE INVENTION

Aspects of the invention relate generally to novel and improved nucleic acid detection methods, and more particularly to novel and improved PCR-based nucleic acid detection methods comprising the use of base-modified, duplex-stabilizing nucleoside triphosphates.

BACKGROUND

I. DNA Detection Technologies

Nucleic acid detection assays and sensitivity. Known DNA and/or RNA detection techniques are based on the principle of complementarity. For example, an oligonucleotide sequence is selected based on its ability to form a complementary duplex with a desired or predetermined nucleic acid target sequence, and the complementary duplex is detected, indicating the presence of the targeted nucleic acid in the reaction mixture. Such hybridization based detection assays should, at least in principal, detect the nucleic acid of interest regardless of its concentration in the test sample. However, the sensitivity of such direct detection hybridization assays is limited, and although some highly sensitive technologies for direct nucleic acid detection are currently under development, amplification of targeted nucleic acids is an important component of typical DNA detection systems. Numerous amplification technologies are known in the art, the most notorious examples including: *Strand Displacement Amplification* (SDA) (Walker G. T. et al, U.S. Pat. No. 5,270,184; Dattagupta N. et al, U.S. Pat. No. 6,214,587; Walker G. T. et al (1996) *Nucleic Acids Res.*, 24, 384-353); *Rolling Circle Amplification* (RCA) (Lizardi P., U.S. Pat. No. 5,854,033); *Linear target Isothermal Multimerization and Amplification* (LIMA) (Hafner G. J. et al (2001) BioTechniques, 30, 852-867); *Loop-Mediated Amplification* (LMA) (Notomi T. and Hase T., U.S. Pat. No. 6,410,278; Notomi T. et al (2000) *Nucleic Acids Res.*, 28, e63); *Isothermal Amplification using chimeric or composite RNA/DNA primers* (Cleuziat P. and Mandrand B., U.S. Pat. No. 5,824,517; Kurn N. (2001) U.S. Pat. No. 6,251,639); *Nucleic Acid Sequence-Based Amplification* (NASBA) (Oehlenschlager F. et al (1996) *Proc. Natl. Acad. Sci. USA*, 93, 12811-12816; Davey C. and Malek L. T., U.S. Pat. No. 6,063,603); and other methods. By far, the most common element among these technologies is the use of oligonucleotide primers that form complementary hybridization complexes with desired/predetermined target sequences of the test nucleic acids, initiating synthesis of DNA copies and providing for target nucleic acid amplification.

Nucleic acid detection using polymerase chain reactions (PCR); limitations in primer design; impediments to nucleic acid detection. DNA consists of only two base pairs, A-T and G-C, and the sequence and orientation of these base pairs in a DNA duplex largely underlies the diversity of life at all comparative genetic levels. In particular, the difference in stability between G-C and A-T base pairs is an important factor in defining DNA function and diversity. However, such differences in duplex stability between A-T and G-C rich sequences pose a serious problem for nucleic acid detection. Whether in the form of a probe or primer, a useful detection oligonucleotide must be able to form a stable complementary hybridization complex with a respective target nucleic acid sequence under suitable conditions to facilitate amplification and/or detection. Significantly, identification of suitable detection oligonucleotides is often challenging or problematic because of thermodynamic diversity of the target nucleic acids; for example, identification of detection oligonucleotides having sufficient utility at the elevated temperatures characteristic of art-recognized Polymerase Chain Reaction (PCR) methods (e.g., Mullis K. B. et al, U.S. Pat. No. 4,683,195 and Mullis K. B., U.S. Pat. No. 4,683,202) is often problematic, and in some instances precluded, because of the presence of particular A-T and G-C sequence compositions in the target sequences (e.g., A-T-rich and/or G-C-rich sequences).

Polymerase chain reaction (PCR) methodology has revolutionized the detection of nucleic acids, where at least in theory, as little as a single copy of DNA or RNA can be amplified and detected. A typical PCR-based detection assay consists of at least two primers and a fluorescent probe. Fluorescence can be detected at the nanomolar level, which is well within the range of PCR sensitivity and productivity. PCR primers are typically designed to bind to opposite DNA strands; that is, the primers bind in an orientation such that extension of one creates a template for the other primer. The PCR reaction runs in cycles in which DNA fragments synthesized in the previous cycle are 'strand-separated' in a denaturation step (typically at 95° C.), followed by rapid cooling to start an 'annealing-extension' stage (typically carried out at 55-65° C.). In annealing stage, the primers bind again to the amplified strands and get extended by a thermophilic DNA polymerase. Under optimal PCR conditions, the concentration of the amplified DNA fragment doubles at each PCR cycle reaching a detectable level after ~20-40 cycles depending on the initial target amount/load.

*Thermus aquaticus* DNA polymerase ("Taq"; Taq polymerase) continues to be the standard, most commonly used enzyme for primer extension in 'detection' PCR because of its thermostability under the characteristic elevated temperatures of the PCR denaturation step/stage. Taq polymerase exhibits maximum activity at approximately 75° C., incorporating more than 60 nucleotides per second, (Takagi M. et al., *Appl. Environ. Microbiol.*, 63: 4504-4510, 1997; Innis M. A. et al., *Proc. Natl. Acad. Sci. USA*, 85: 9436-9440, 1988), thus defining an optimal extension temperature for PCR. In principal, performing PCR at such elevated temperatures (e.g. 75° C.) affords several advantages. For example, extending at elevated temperatures decreases the temperature gap/difference between denaturation (e.g., 95° C.) and annealing/extension steps/stages to 20° C., saving time on temperature ramping during a PCR cycle, and this saved time can be significant for particular real-time PCR instruments (e.g., like the ABI 7700 or 7900, and the Bio-Rad iCycler™). Additionally, PCR at elevated temperatures is more sequence specific, because misamplification and formation of primer-dimers is enhanced/accelerated at reduced temperatures. However, despite the benefits of conducting PCR at such optimal Taq temperatures, use of annealing temperatures above 70° C. is exceptionally rare, and for practical reasons (e.g., probe/target duplex stability) the most commonly used temperatures for primer annealing range from ~56-58 to ~60-62° C., and rather, after annealing, an additional extension stage (>72° C.) is commonly introduced to enhance the efficiency of the extension step/stage. Unfortunately, while elevating the temperature for an additional extension stage (>72° C.) enhances this aspect of the PCR reaction, even short exposure of the reaction to low annealing temperature can trigger "mispriming" and primer-dimer formation. Nonetheless, the typical annealing ranges (from ~56-58 to ~60-62° C.) persist in view of the structural and thermodynamic diversity of the nucleic acid or DNA per se; that is, A/T-rich duplexes are significantly less stable than duplexes with relatively elevated G/C content, and reaction conditions utilizing more elevated annealing temperatures would significantly limit the scope of prior art methods. For example, the exemplary Tm data shown in FIG. 1 illustrates the problem of the efficiency differential between annealing and optimal Taq extension.

In FIG. 1, the primer no. 1 (SEQ ID NO:1) is a completely AT-rich 22-mer oligonucleotide which was randomly designed to avoid long mono- and dinucleotide repeats, and to have an equal A/T base ratio. Other primers, nos. 2-23 (SEQ ID NOS:2-23), were derived based on SEQ ID NO:1, by gradually increasing GC-content by changing T to C and A to G, respectively. As can be seen, the thermal stability of these exemplary 22-mer oligonucleotides varies in a broad range of temperatures from 43 to 85° C., depending upon the GC base content. For example, primers with GC contents below 35-40% do not meet stability requirements for PCR at 60° C., clarifying why the preferred range of GC content used by all modern software for PCR primer design is within a range of ~40-80%. In practice, a 22-mer represents a typical length for a PCR primer, and this primer length generally addresses the minimum $T_m$ requirements. However, unless the extension extends through a 'GC island,' increasing the primer length for analysis within AT-rich sequences does not overcome the associated thermal stability problem. FIG. 2 illustrates that thermal stability of $(dA-dT)_n$ homopolymers tends to reach a 'plateau' value slightly above 60° C., and increased stabilization efficiency per base (° C./base) decreases rapidly for oligonucleotides longer than 25-30-mers. Additionally, extremely AT-rich primers cannot be used for PCR at temperatures>70° C. Moreover, long primers (>30-40-mers) have limited use because of associated low manufacturing yields and quality.

Polymorphic variations and gene expression studies. Gene expression studies are among the least likely PCR applications to be associated with problems in system designs because the target gene sequences are usually relatively long, providing ample sequence distance for design of suitable primers and a probe. By contrast, PCR system designs for detection of polymorphisms (e.g., SNPs) are limited to or restricted by the location of the target polymorphism, and establishing a good system or detection design is typically difficult, in not impossible when the target polymorphism is located within a thermoliable target region with an AT content exceeding ~65-70%. Generally speaking, PCR amplicons should be as short as possible, because the length of amplicons generally inversely affects the PCR yield and, consequently, the overall performance of nucleic acid detection assays.

PCR instrumentation. The SMARTCYCLER™ (Cepheid Corporation) is an example of a real-time fluorescent instrument that can perform PCR assays with individualized temperature and time profiles for each reaction cell or compartment. However, the instrument has only 16 PCR reaction compartments and, while exceptional, is consequently not particularly suited for high-throughput analysis. All other commercially available instruments provide for the use of common or uniform PCR conditions for all reaction cells in the reaction run. For these instruments, therefore, selection of an elevated temperature PCR regime may preclude detection of many targets of interest, narrowing the analytical scope. Therefore, the profile uniformity requirement is a major factor influencing and/or dictating the choice of assay temperature.

Additionally, in many FRET system designs (e.g., TaqMan™, and Beacons™), the $T_m$ scale of the probe must be at least 5° C. more stable than that of the primers to precluded diminishment of the fluorescent signal below acceptable levels. This requirement contributes to the motivation for use of lower annealing temperatures. For example, where the primers are designed to perform at an annealing temperature of 70° C., the probe $T_m$ must be >75° C., which is a difficult requirement to achieve.

Enhancement of probe and primer hybridization properties. A number of techniques to enhance probe and primer hybridization properties are known in the art. For example, conjugation with a 'major groove binding moiety' (MGB-moiety; Kutyavin I. V. et al., *Nucleic Acids Res.*, 25: 3718-3723, 1997) is a robust duplex stabilizing agent that has revitalized TaqMan™ technology (Kutyavin I. V. et al., *Nucleic Acids Res.*, 28: 655-661, 2000). Likewise, in the case of MGB-tailed Eclipse probes (Afonina I. A. et al., *BioTechniques*, 32: 940-949, 2002), enablement of a substantial reduction in probe length adventitiously resulted in lower fluorescence backgrounds. For example, relatively short 12-18-mer MGB-TaqMan™ probes were shown to provide for improved SNP discrimination (Kutyavin I. V. et al., *Nucleic Acids Res.*, 28:655-661, 2000), and provision of relatively good signal levels and straightforward manufacturing contributes to the commercial success and wide acceptance of such probes. Additionally, Locked Nucleic Acid™ ("LNA™") derivatives are successful modifications used in the design of FRET probes (Goldenberg, O. et al., *Biotechniques*, 38: 29-32, 2005; You, Y. et al., *Nucleic Acids Res.*, 34: e60, 2006), as well as Protein Nucleic Acid ("PNA") derivative (Ortiz, E. et al., *Mol. Cell. Probes*, 12, 219-226, 1998). Unfortunately, however, DNA polymerase (e.g., Taq) does not tolerate many, if not most of the structural modifications potentially applicable in probe designs. For example, although LNA nucleotide analogs can be incorporated in to the oligonucleotide primers, the number of these modifications is limited. Examples of use of LNA-modified primers are described in Latorra D. et al *Mol. Cell. Probes*, 17: 253-259, 2003; Latorra D. et al., *Hum. Mutat.*, 22:79-85, 2003; Di Giusto D. A. and King G. C., *Nucleic Acids Res.*, 32: e32, 2004.

Therefore, there is a pronounced need in the art for versatile and simple approaches to improve PCR amplification and detection of compositionally deviant or extreme nucleic acid sequences, and in particular in the context of A-T-rich target sequences.

II. Enzymatic Synthesis of Nucleic Acids Using Modified Analogues of Nucleoside 5'-Triphosphates Regardless of the significant progress made up to date in nucleic acids detection, the methods of enhancing the hybridization properties of primers and probes are still not optimal Base-modified primers. Manufacturing of modified oligonucleotides carrying duplex-stabilizing moieties and nucleotide analogs is limited, complex and expensive. For example, Lebedev Y. and coworkers (*Genet. Anal.*, 13: 15-21, 1996) have demonstrated the benefits of using PCR primers and probes that contain modified bases such as 5-methyl cytosine (5-MeC) and 2,6-diamino-purine (2-amA) in place of cytosine and adenine, respectively (Prosnyak M. I. et al., *Genomics,* 21: 490-494, 1994). These oligonucleotides have a higher than normal affinity for complementary sequences and they perform better than their normal counterparts in PCR amplification. Significantly, use of such primers and probes allows amplification at annealing temperatures as high as 72° C. (Lebedev Y. et al., *Genet. Anal.,* 13:15-21, 1996). Unfortunately, these base-modified primers have not adopted in the art, most likely because of the relatively high cost of manufacturing.

Use of modified nucleoside 5'-triphosphates in primer extension and PCR. Use of modified 5'-triphosphates in preparing modified DNA or RNA polymers has been reported for applications in bioengineering, nanotechnology, molecular biology and medicine. Chemical synthesis of polynucleotides is inefficient and difficult, and certain structural modifications can not be chemically introduced because of their relative instability. Enzymatic synthesis is an alternative approach to prepare the desired biopolymers, and numerous studies have been conducted to determine the scope of nucleotide modifications that support enzymatic synthesis.

Modified polynucleotides have been used in: nucleic acid sequencing (Ward B. et al (2005) U.S. Pat. No. 6,902,914; Porter K. W. et al (1997) *Nucleic Acids Res.,* 25:1611-1617); and development of immobilization and labeling techniques, and studies of nucleic acid interactions with proteins (Seela F. and Röling A. (1992) *Nucleic Acids Res.,* 20: 55-61; Bailly C. and Waring M. J. (1995) *Nucleic Acids Res.,* 23: 885-892; Bailly C. et al (1998) *Biochemistry,* 37: 1033-1045; Bailly C. and Waring M. J. (1998) *Nucleic Acids Res.,* 26: 4309-4314). Additionally, certain nucleotide modifications have been used in: enhancing the catalytic repertoire of nucleic acids (Jäger S. and Famulok M. (2004) *Angew. Chem. Int. Ed.,* 43: 3337-3340; Lee S. E. et al (2001) *Nucleic Acids Res.,* 29: 1565-1573; Held H. A. and Benner S. A (2002) *Nucleic Acids Res.,* 30: 3857-3869; Kuwahara M. et al (2003) *Nucleic Acids Res. Suppl.,* 3: 37-38); protecting polynucleotides from exo- and endo-nucleases (Ward B. et al (2005) U.S. Pat. No. 6,902,914; Summers J. S. and Shaw B. R. (2001) *Current Medicinal Chemistry,* 8: 1147-1155; Shaw B. R. et al (2004) U.S. Pat. No. 6,808,897; Porter K. W. et al (1997) *Nucleic Acids Res.,* 25: 1611-1617; Seela F. and Röling A. (1992) *Nucleic Acids Res.,* 20: 55-61); and providing duplex DNA polymers to study methyl-dependant endonucleases (Wong K. K. and McClelland, M. (1991) *Nucleic Acids Res.,* 19: 1081-1085).

However, examples of using modified dNTP derivatives to prepare polynucleotides with enhanced hybridization properties are exceptionally rare. Specifically, the reported studies relate to enzymatic synthesis of single-stranded, fluorescently labeled RNAs for detection and characterization by microarray hybridization, where base-modified analogues of ribonucleoside 5'-triphosphates (rNTPs) were used in RNA polymerization with the intent to improve microarray hybridization signals across a wide range of sequences and expression levels. For example, Nguyen A. et al (*BMC Biotechnology,* 2:14, 2002) used duplex-stabilizing ribonucleoside 5'-triphosphates (rNTPs) such as 2,6-diaminopurine r(2-amA)TP, 5-methyl uridine r(5-MeU)TP and 5-methyl cytosine r(5-MeC)TP 5'-triphosphates, whereas Hacia J. G. and coworkers (*Nucleic Acids Res.,* 26:4975-4982, 1998) studied r(2-amA)TP, r(5-MeU)TP and 5-(1-propynyl)-uridine r(5-PrU)TP analogs. Nguyen et al found that RNA samples containing 2,6-diamino-purine increased signal intensity for a majority of the sequences while two other duplex-stabilizing modifications used, r(5-MeU)TP and r(5-MeC)TP led to a signal decrease. By contrast, Hacia et al., reported positive results for 5-methyluridine-containing target RNAs that displayed localized enhancements in hybridization signal while maintaining single nucleotide mismatch hybridization specificities comparable with those of unmodified RNA targets. On the other hand, they observed reduction of hybridization signal intensities for r(2-amA)-containing RNA targets. Therefore, these reported results are inconsistent and inconclusive and do not clarify the art with respect to any general or further applicability of the use of base-modified analogues of ribonucleoside 5'-triphosphates (rNTPs).

Nucleotide polymerases have been shown to be especially sensitive to modifications of the sugar moiety in nucleotides (Kempeneers V. et al (2005) *Nucleic Acids Res.,* 33:3828-3836). Certain sugar modifications in dNTPs inhibit viral DNA polymerases making these compounds interesting for medicinal chemistry as drug candidates (Matthes E. et al (1991) *Antimicrob. Agents Chemother.,* 35:1254-1257; Reid R. et al (1988) *J. Biol. Chem.,* 263:3898-3904). 2'-Fluoro modified 2'-deoxyribo nucleosides are additional examples of sugar modification in dNTPs, but use of these derivatives in DNA polymerization is limited (Ono T. et al (1997) *Nucleic Acids Res.,* 25:4581-4588). Ono, T. et al., identified only four DNA polymerases Pfu(exo-), Vent(exo-), Deep Vent(exo-) and UITma that were able to incorporate 2'-fluoro dNTPs derivatives with reasonable efficiency. Relatively minor modifications at the α-phosphate moiety of dNTPs can be tolerated by DNA polymerases (Dobrikov M. I. et al (2003) *Nucleosides Nucleotides Nucleic Acids,* 22:1651-1655), with the most recognized examples being thio- (Ward B. et al (2005) U.S. Pat. No. 6,902,914) and borano-phosphate derivatives (Summers J. S. and Shaw B. R. (2001) *Current Medicinal Chemistry,* 8:1147-1155; Shaw B. R. et al (2004) U.S. Pat. No. 6,808,897). Substrate properties of these modified dNTPs are comparable with those of natural nucleotides and this makes possible their application in PCR-based sequencing (Ward B. et al (2005) U.S. Pat. No. 6,902,914; Porter K. W. et al (1997) *Nucleic Acids Res.,* 25: 1611-1617). However, these modifications have a negatively effect on DNA hybridization properties (Wang J. X. et al (2005) *Nucleosides Nucleotides Nucleic Acids,* 24: 951-955) and this makes these borano-modified dNTPs effectively useless in practicing detection PCR.

Ironically, dNTP derivatives which lead to the duplex destabilization have found the most applicability in PCR. Seela & Röling (*Nucleic Acids Res.,* 20:55-61. 1992) investigated substrate properties of 7-deazapurine analogues of dNTPs and found that 7-deaza deoxyriboguanisine 5'-triphosphate ($c^7G_dTP$) can completely replace the natural dGTP in PCR reactions, whereas two other studied derivatives, 7-deaza deoxyriboadenosine 5'-triphosphate ($c^7A_dTP$) and 7-deaza deoxyriboinosine 5'-triphosphate ($c^7I_dTP$) required the presence of the parent dNTPs. It was also shown that these are duplex destabilizing modifications. Gourlain T. et al., (*Nucleic Acids Res.,* 29: 1898-1905, 2001) showed that substrate properties of $c^7A_dTP$ can be improved via incorporation of pendant aminopropyl, Z-aminopropenyl and aminopropynyl side chains at the C7-position of the heterocyclic system, however, accurate measurements of PCR yield were not done and the utility and applicability of these derivatives to detection PCR has not been established. Substitution of the N7 position in purines by a carbon atom reduces duplex stability and this property can be effectively used, for example, in resolving the notorious problems of poly G-rich sequences. For example, Dierick H. et al., (*Nucleic Acids Res.,* 21:4427-4428, 1993) used $c^7G_dTP$ and $c^7I_dTP$ analogs to avoid premature enzyme pausing during sequencing of PCR templates. Such destabilizing effects are especially profound for deoxyinosine, and the respective dITP analogue was successfully used for selective RT-PCR amplification of mRNAs in the presence of genomic DNA (Auer T. et al (1996) *Nucleic Acids Res.*, 24:5021-5026). However the reported data indicate that application of dITP in PCR is extremely limited and these base-modified nucleoside triphosphates cannot be used as complete substitution for natural dGTP.

Deoxyuridine triphosphate (dUTP) is yet another example of a duplex-destabilizing dNTP that is commonly used in PCR. It is usually applied as a complete substitution for thymidine 5'-triphosphate (dTTP). DNAs containing dU nucleosides can be selectively cleaved in presence of uracil glycosylase (Demple B. et al (1986) *Proc. Natl. Acad. Sci. USA*, 83:7731-7735; Wilson III D. M. et al (1997) *Nucleic Acids Res.*, 25:933-939; Strauss P. R. et al (1997) *J. Biol. Chem.*, 272:1302-1307) and treatment of the samples prior to PCR reactions helps in preventing contamination carryovers from sample to sample (Gelfand D. H. et al (1995) U.S. Pat. No. 5,418,149).

Pyrimidines substituted at the 5-position are reasonably tolerated by DNA polymerases making the respective dNTP analogues promising for use in PCR. The modifying moieties can be as big as imidazole 4-acetic- and urocanic acid coupled via 3-amino-propynyl and E-3-aminopropenyl linkers (Lee S. E. et al (2001) *Nucleic Acids Res.*, 29:1565-1573). In contract to these rigid linkers, flexible alkyls negatively affect dNTP substrate properties. Held, H. A. et al., (*Nucleic Acids Res.*, 30:3857-3869, 2002) examined eight different polymerases for their ability to incorporate 5-modified 2'-deoxyuridine derivatives that carry a protected thiol group appended via alkyl-type linkers containing either three or four carbon atoms. The polymerases reacted differentially with the base-modified dUTP in PCR. Although no accurate data about PCR yield was provided, the authors claimed that PCR products were observed in many cases. Similar results were obtained by Kuwahara, M. et al., (*Nucleic Acids Res. Suppl.*, 3:37-38, 2003), who studied modified analogs of 2'-deoxycytidine triphosphates, bearing (6-aminohexyl) carbamoylmethyl or 7-amino-2,5-dioxaheptyl linkers at the C5-position. Both analogs were found to be good substrates for Vent(exo-) DNA polymerase in PCR, resulting in full-length modified DNAs.

It is presently unclear whether there is a positive or negative thermodynamic contribution on duplex formation in reported studies using particular base-modified dNTPs (Lee S. E. et al (2001) *Nucleic Acids Res.*, 29:1565-1573; Held H. A. and Benner S. A (2002) *Nucleic Acids Res.*, 30:3857-3869; Kuwahara M. et al (2003) *Nucleic Acids Res. Suppl.*, 3:37-38; Gourlain T. et al (2001) *Nucleic Acids Res.*, 29:1898-1905; Jäger S. and Famulok M. (2004) *Angew. Chem. Int. Ed.*, 43:3337-3340). Moreover, in the cases where a duplex-stabilizing effect of the base modification has been indicated, for example in the case of 5-methyl-cytosine (Szer W. (1965) *Biochem. Biophys. Res. Commun.*, 20:182-186; Ono A. and Ueda T. (1987) *Nucleic Acids Res.*, 15:219-232; Butkus V. et al (1987) *Nucleic Acids Res.*, 15:8467-8478; Szer W. and Shugar D. (1966) *J. Mol. Biol.*, 17:174-187; and Uesugi S. et al (1986) *Chem. Pharm. Bull.*, 34:51-60), PCR complications were reported providing no amplification product in some cases (see, Wong K. K. and McClelland, M. (1991) *Nucleic Acids Res.*, 19:1081-1085).

2,6-Diaminopurine is another base analog with a profound duplex-stabilizing effect (Howard F. B. et al (1966) *J. Biol. Chem.*, 241:4293-4295; Howard F. B. et al (1976) *Biochemistry*, 15:3783-3795; Howard F. B. and Miles H. T. (1984) *Biochemistry*, 23:6723-6732; Scheit K. H. and Rackwitz H.-R. (1982) *Nucleic Acids Res.*, 10:4059-4069; Gaffney B. L. et al (1984) *Tetrahedron*, 40:3-13). According to Kuwahara M. et al., (*Nucleic Acids Res. Suppl.*, 3:37-38, 2003), however, use of the respective d(2-amA)TP analog in PCR is restricted to relatively short amplicons. Bailly, C. et al described PCR-assisted synthesis of a relatively long 160 bp double stranded DNA fragment by using 2,6-diaminopurine deoxynucleoside triphosphates as a complete replacement of dATP (Bailly C. and Waring M. J. (1995) *Nucleic Acids Res.*, 23:885-892; Bailly C. et al (1998) *Biochemistry*, 37:1033-1045; Bailly C. and Waring M. J. (1998) *Nucleic Acids Res.*, 26:4309-4314), but the authors reported using significantly abnormal PCR conditions (annealing temperature and time) reflecting the limits on the utility of d(2-amA)TP in PCR. Unfortunately, all of the above cited studies did not include accurate comparisons of the modified dNTPs with the substrate properties of the respective natural deoxynucleoside 5'-triphosphates, so the practical utility of these analogs for detection PCR remains ambiguous and uncertain in the art.

In summary therefore, the traditional approaches to duplex stabilization that concentrate on the primer and probe modification are impractical, and the utility of incorporating base analogs during amplification in detection PCR remains ambiguous and uncertain in the art.

There is, therefore, and despite some progress in the use of modified nucleotides, a pronounced need in the art for versatile, simple, and inexpensive approaches to stabilize complementary complexes of oligonucleotides while providing for fast and robust amplification and detection of target nucleic acids. There is a pronounced need in the art for a versatile and simple approach to improve PCR amplification and detection of compositionally deviant or extreme nucleic acid sequences, and in particular in the context of A-T-rich target sequences.

and scorpion primer (SEQ ID NO:28) structure also shown. In the Scorpion primer (SEQ ID NO:28), a hairpin forming FRET probe (complementary end sequences are underlined) is connected to the 5'-end of the forward primer via a long and flexible C18-linker (Glen Research). The primers and probe used were made from all natural nucleoside, or alternatively incorporated modified bases. When base-modified oligonucleotides were used, the positions shown in bold-faced font were substituted with 2,6-diamino-purine or 5-methyl cytosine respectively. Underlined in the sequence of SEQ ID NO:24 is the binding site of the reverse primer (shown in reverse, 3'→5' orientation). "FAM" refers to 6-fluorescein and "Q" refers to BLACK HOLE QUENCHER™ (BHQ1) from Biosearch Technologies.

Figure 1:
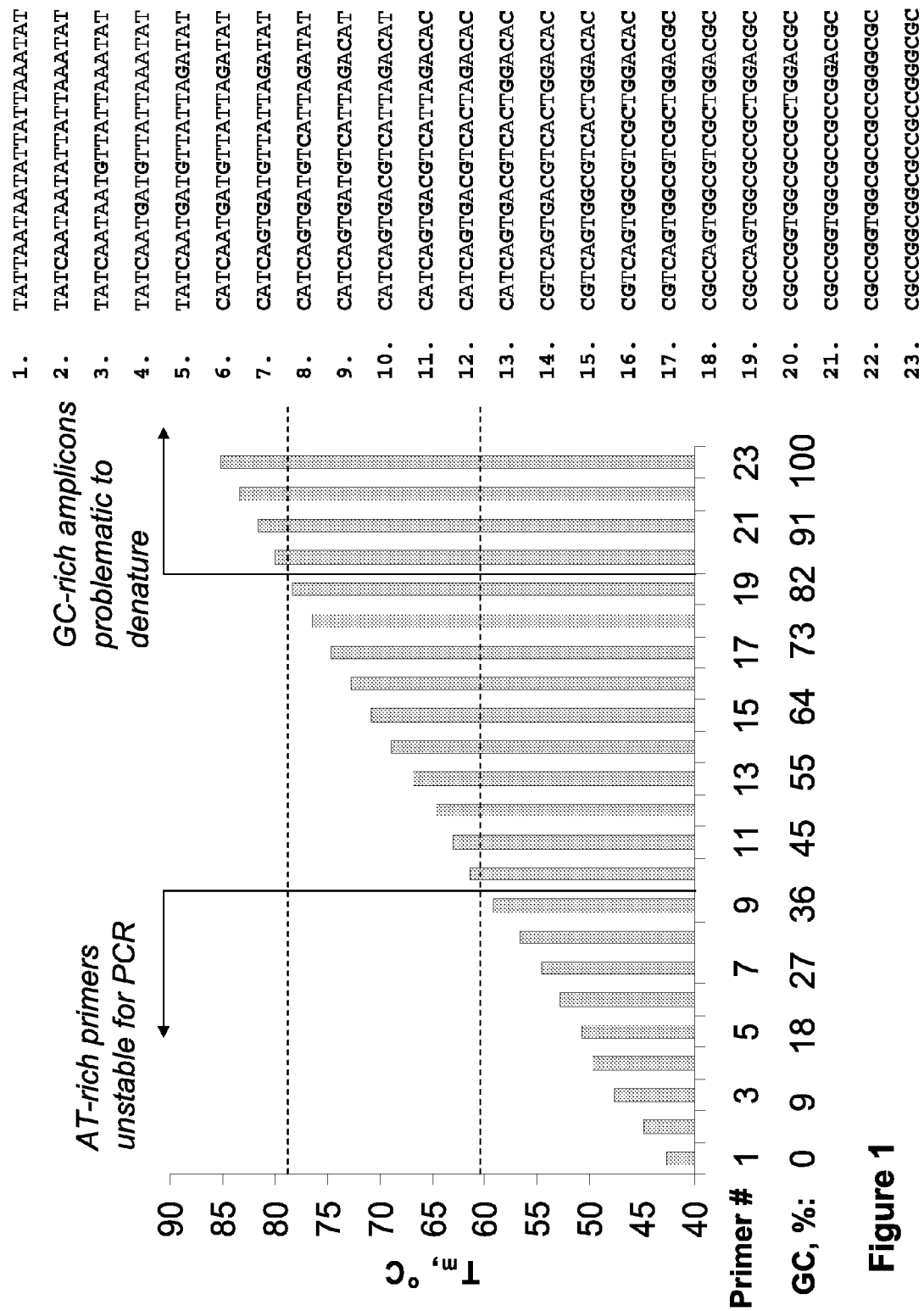
FIG. 1 shows, according to exemplary aspects of the present invention, a bar diagram showing the dependence between melting temperatures (Tm) and G/C-base content of 22-mer PCR primers (SEQ ID NOS:1-23). Sequences of the primers are shown on the right. Tm calculations were based on conditions corresponding to 40 mM NaCl, 5 mM $MgCl_2$, 20 mM Tris-HCl (pH 8.0) with 200 nM primer and 200 nM complement. Primers between the vertical lines are preferred in PCR assay designs. Primers with G/C content<40% have Tm values too low to form stable hybrids under harsh PCR conditions (e.g., 60° C.), whereas primers with G/C content>80% can over stabilize the amplicon if the rest of amplicon has a high G/C content.
Figure 2:
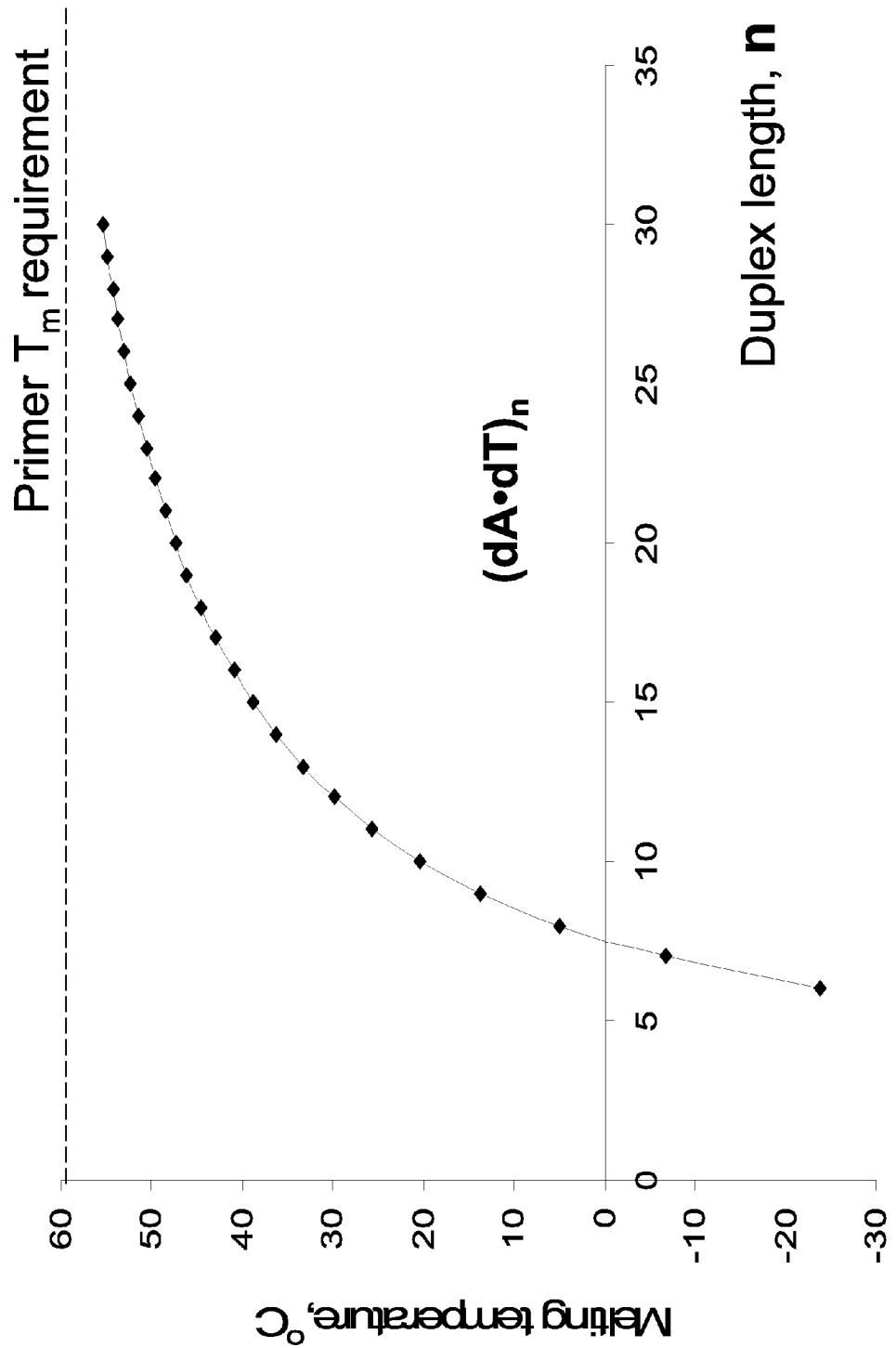
FIG. 2 shows, according to exemplary aspects of the present invention, dependence of the stability of a homopolymer $(dA \cdot dT)_n$ duplex plotted vs. duplex length. Melting temperatures were calculated using the approach and conditions described in FIG. 1.

FIGS. 5A-5D show exemplary results of fluorescence monitoring obtained for TaqMan® detection assays during real-time PCR on a SmartCycler™ (Cepheid). Structures of the target oligonucleotide (SEQ ID NO:24), forward (SEQ ID NO:25) and reverse (SEQ ID NO:26 PCR primers and TaqMan® probe (SEQ ID NO:27) used are as in FIG. 2. Final concentrations of components in the reaction mixtures (25 µl) at the start of PCR were: forward and reverse PCR primers—200 nM; TaqMan® probe—200 nM; target oligonucleotide—10,000 copies per reaction; dNTPs—200 µM each; JUMP START™ DNA polymerase (Sigma)—0.04 U/µl in 50 mM KCl, 2 mM MgCl$_2$, 20 mM Tris-HCl (pH 8.0). Background fluorescence was subtracted. The PCR cycling profile (95° 2')→(95°10"→X°45")$_{55}$ was used with the annealing temperature "X" varying from 65 to 75° C.

FIG. 5A shows an exemplary set of experiments where unmodified primers and TaqMan® probe were employed with all natural dNTPs.

FIG. 5B shows results of exemplary experiments that are analogous to those of FIG. 5A, but wherein natural 2'-deoxyriboadenosine-5'-triphosphate (dATP) was completely substituted with 2'-deoxyribo-2,6-diaminopurine nucleoside-5'-triphosphate (d(2-amA)TP).

In FIG. 5C, base-modified primers and probes were used in the set of exemplary experiments, but wherein all nucleoside triphosphates (dNTPs) were natural.

FIG. 5D represents real-time TaqMan® assays where both system modifications of FIG. 5B and FIG. 5C were combined and employed at the same time; that is, base-modified primers and probe were used with complete d(2-amA)TP substitution of dATP.

FIGS. 6A-6D show results of the real-time TaqMan® assays when one of natural dNTPs (used in FIG. 6A) was completely substituted with: 5-bromo-2'-deoxyribouridine-5'-triphosphate (d(5-BrU)TP, FIG. 6B); 5-propynyl-2'-deoxyribouridine-5'-triphosphate (d(5-PrU)TP, FIG. 6C) and 5-methyl-2'-deoxyribo-cytidine-5'-triphosphate (d(5-MeC)TP, FIG. 6D), respectively. FIG. 6A is identical to FIG. 5A, and it is shown here to facilitate direct comparison. PCR primers and TaqMan® probe were unmodified. Other PCR reaction compositions, component concentrations and temperature/time profiles were the same as described in the exemplary experiments shown in FIG. 3.

FIGS. 7A-7D show results of real-time fluorescence monitoring in exemplary TaqMan® assays at variable annealing temperatures (shown in ° C. for every curve). FIG. 7B shows fluorescent curves in the PCR reaction when two natural dNTPs (dATP and dTTP) were completely substituted with their respective base-modified analogs d(2-amA)TP and d(5-PrU)TP. Results in FIG. 7A are identical to those shown in FIG. 5A. PCR primers and TaqMan® probe were unmodified. Other PCR reaction compositions, component concentrations and temperature/time profiles were the same as described or the exemplary experiments of FIG. 5. The panel diagrams FIGS. 7C and 7D that are shown below FIGS. 7A and 7B, respectively, are the same results as shown in FIGS. 7A and 7B, but are plotted in logarithm scale. Fluorescent curve thresholds ("C$_t$") are shown by arrows, and were determined as cycle numbers at which the logarithm curves (i) point to, or (ii) intercept the X axis.

FIGS. 8A and 8B show real-time fluorescence curves. FIG. 8A shows the combined real-time fluorescence curves obtained for the same TaqMan® assay and reaction composition used in the FIG. 7B experiments, however the PCR profile was different; namely, (95° 2')→(9X°YY"→67° 45")$_{55}$. In this case, the annealing temperature was constant (67° C.), and the denaturation conditions were varied in temperature (X=95-97° C.) and time (YY=10 or 15 seconds) as indicated for every curve. PCR primers and TaqMan® probe were unmodified. Other PCR reaction compositions and component concentrations were the same as described in FIG. 5. FIG. 8B (right) shows the same experiments as in FIG. 8A, but fluorescence is plotted in logarithm scale. Fluorescent curve thresholds ("C$_t$") are shown by arrows for the 95°10" and 97°15" curves.

Figure 5:
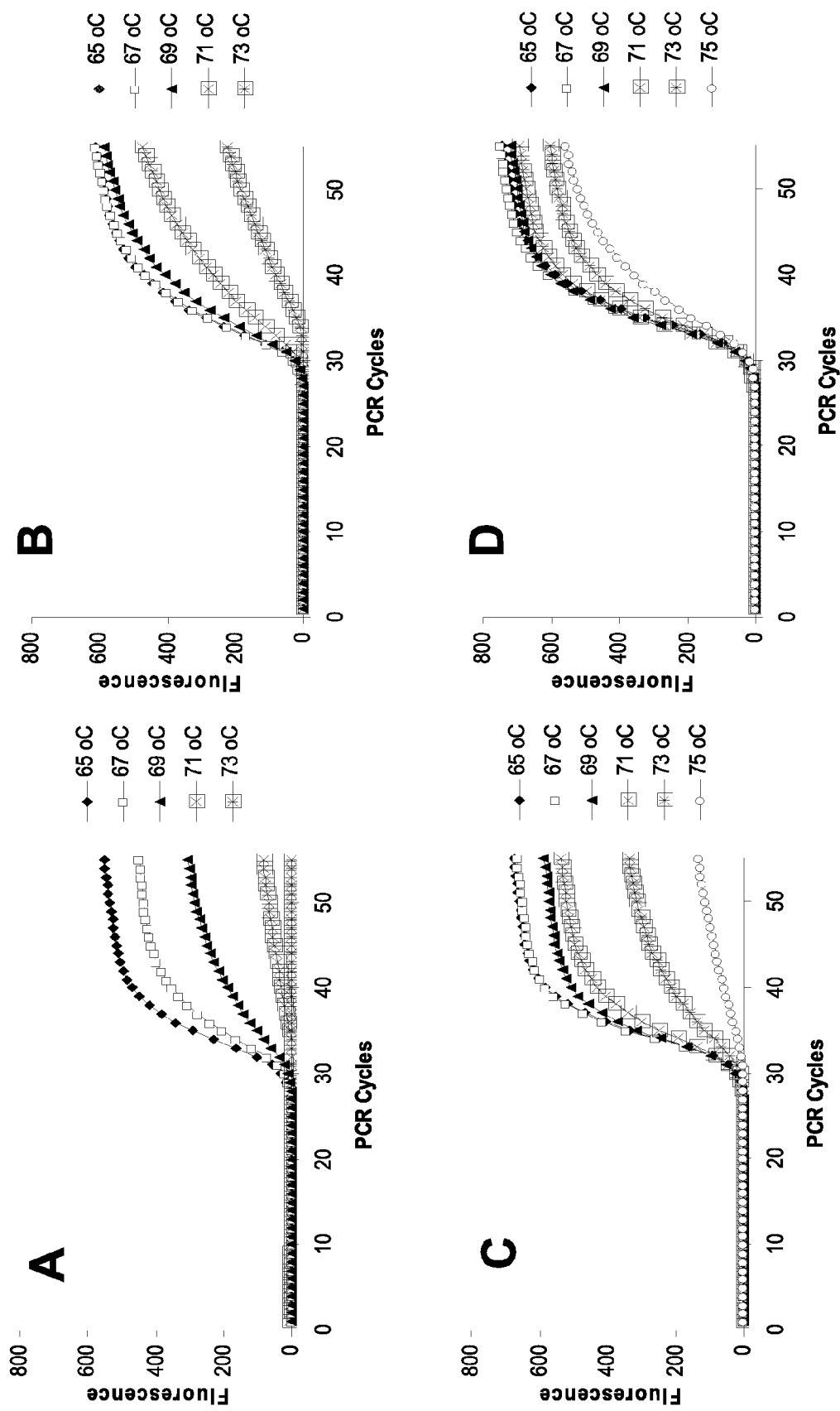
Figure 6:
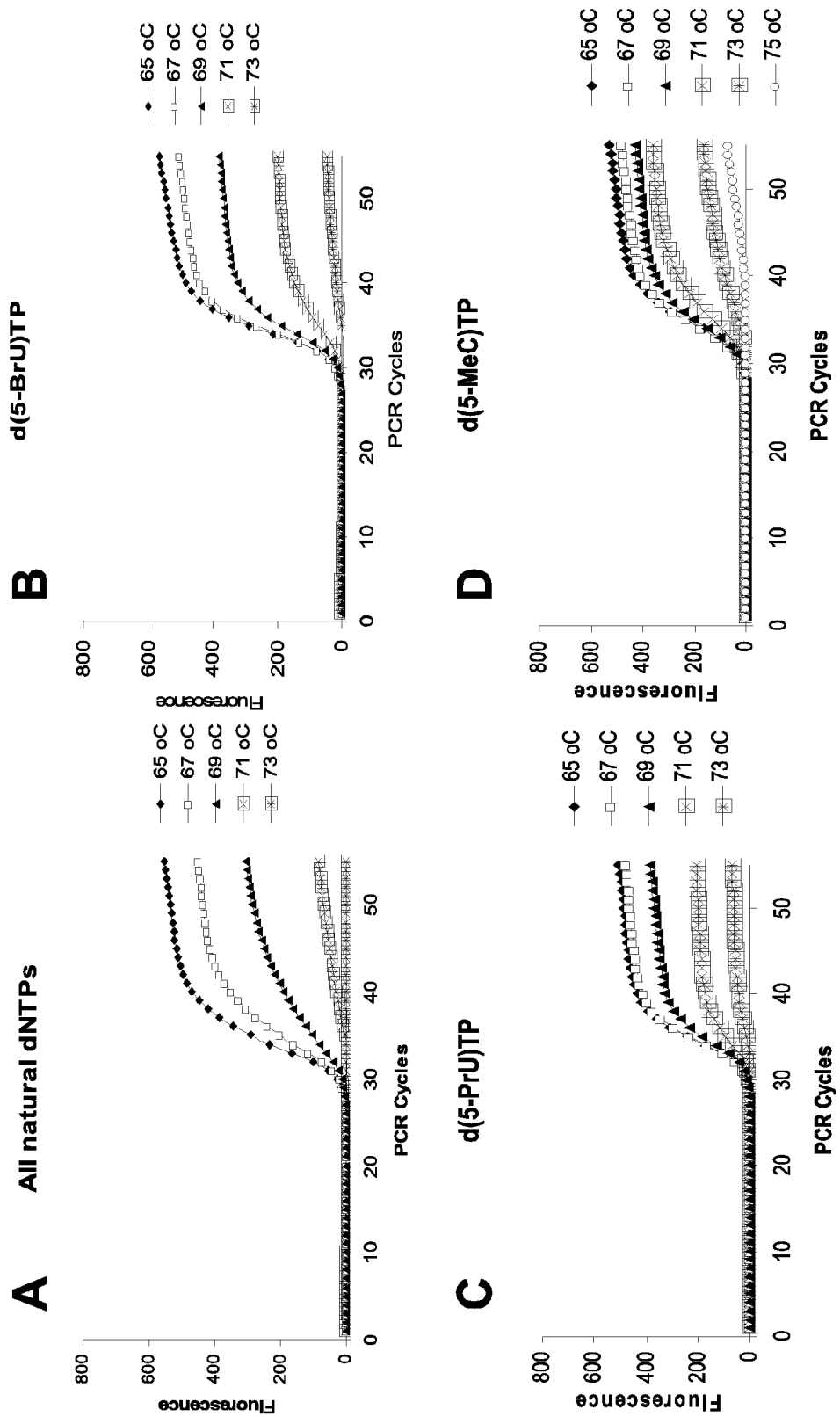
Figure 7:
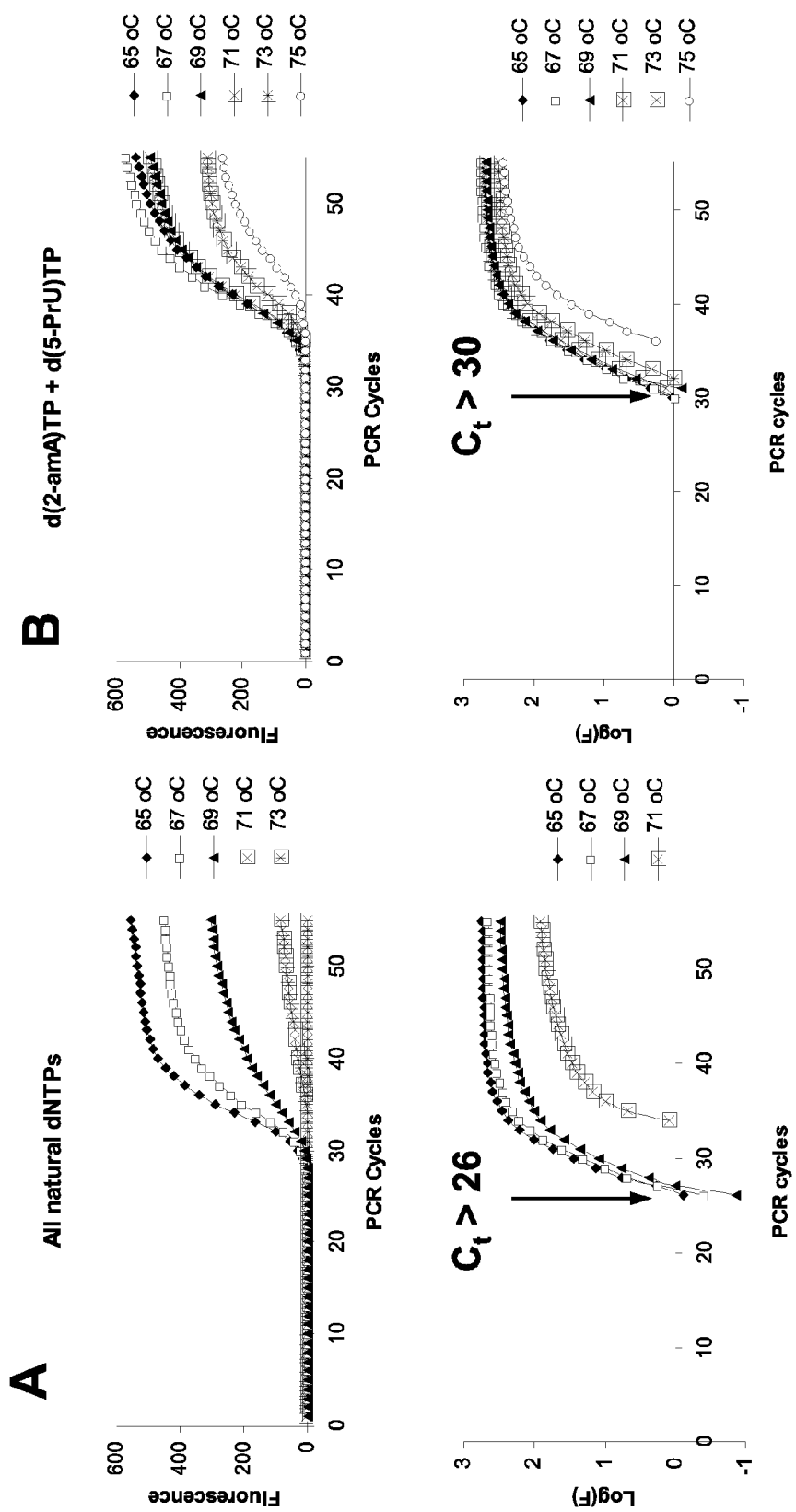
Figure 9:
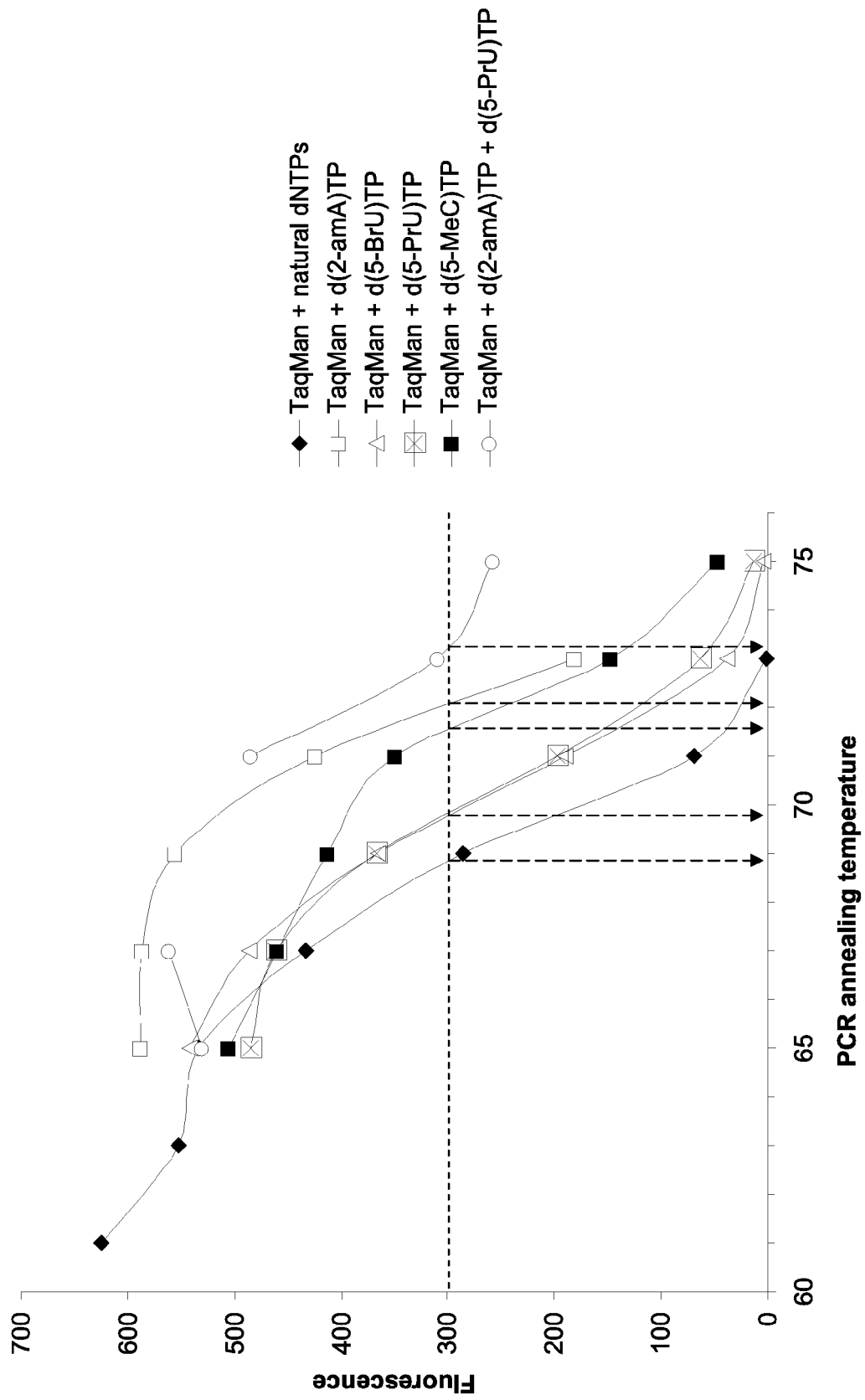

FIG. 9 shows signal performance of the TaqMan® assays shown in exemplary FIGS. 5, 6 and 7 versus annealing temperature of PCR. Fluorescence of every individual reaction at PCR cycle 50 was plotted against the annealing temperature used in that reaction. In cases where two natural dNTPs were substituted with d(2-amA)TP and d(5-PrU)TP, the fluorescence data were taken at cycle 54, because of the 4-cycle "delay" in C$_t$ value observed in that assay (FIG. 7). Arrows point to the annealing temperatures at which approximately half of the assay signal (300 fluorescence units) has been reached.

Figure 4:
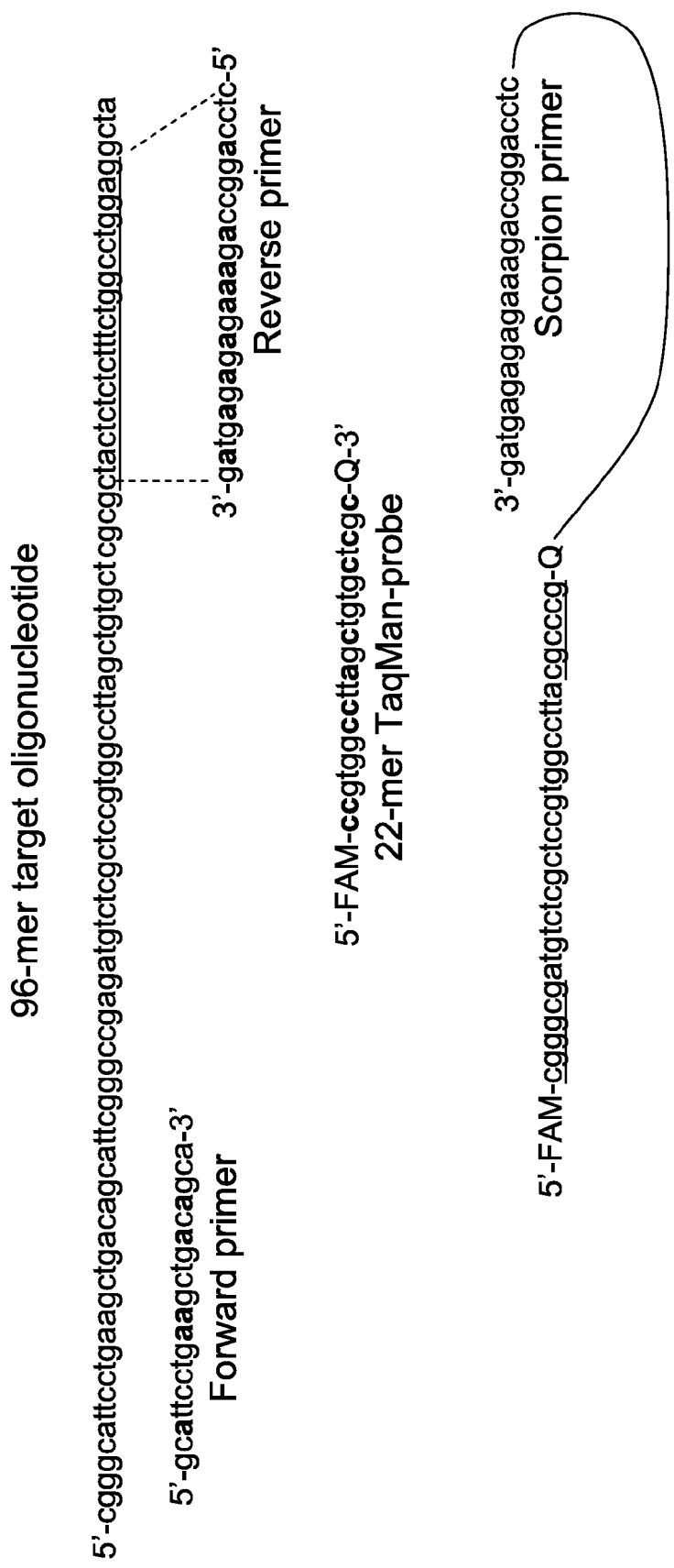
FIG. 4 shows sequences of a 96-mer target oligodeoxyribonucleotide (SEQ ID NO:24), forward (SEQ ID NO:25) and reverse (SEQ ID NO:26) PCR primers and a 22-mer fluorescent probe (SEQ ID NO:27) used in TaqMan® assays in exemplary aspects of the present invention. Scorpion assays were performed using the reverse primer (SEQ ID NO:26)

FIGS. 10A-10C show results of fluorescence monitoring obtained for scorpion detection assays. Structures of the target oligonucleotide, forward and scorpion PCR primers used are as shown in FIG. 4. Final concentrations of components in the reaction mixtures (25 µl) at the start of PCR: forward and scorpion PCR primers—200 nM; target oligonucleotide—10,000 copies per reaction; dNTPs—200 µM each; JUMP STAR™ DNA polymerase (Sigma)—0.04 U/µl in 50 mM KCl, 2 mM MgCl$_2$, 20 mM Tris-HCl (pH 8.0). Background fluorescence was subtracted. PCR profile (95°2')→(95°10"→X°45")$_{55}$ was used with the annealing temperature X varying from 61 to 75° C.

FIG. 10A shows a set of exemplary experiments where a scorpion detection system was employed with all natural dNTPs. FIG. 10B shows experimental results that are analogous to FIG. 10A, but natural dATP was completely substituted with a d(2-amA)TP base-modified analog. FIG. 10C shows a set of experiments that are also analogous to FIG. 10A, but in this case, two of natural dNTPs, in particular, dATP and dTTP were completely substituted with respective base-modified analogs d(2-amA)TP and d(5-PrU)TP. To insure stability of the C$_t$ values, a slightly different PCR profile of (95°2')→(97°15"→X°45")$_{55}$ was used in the FIG. 10C set of experiments.

Figure 10:
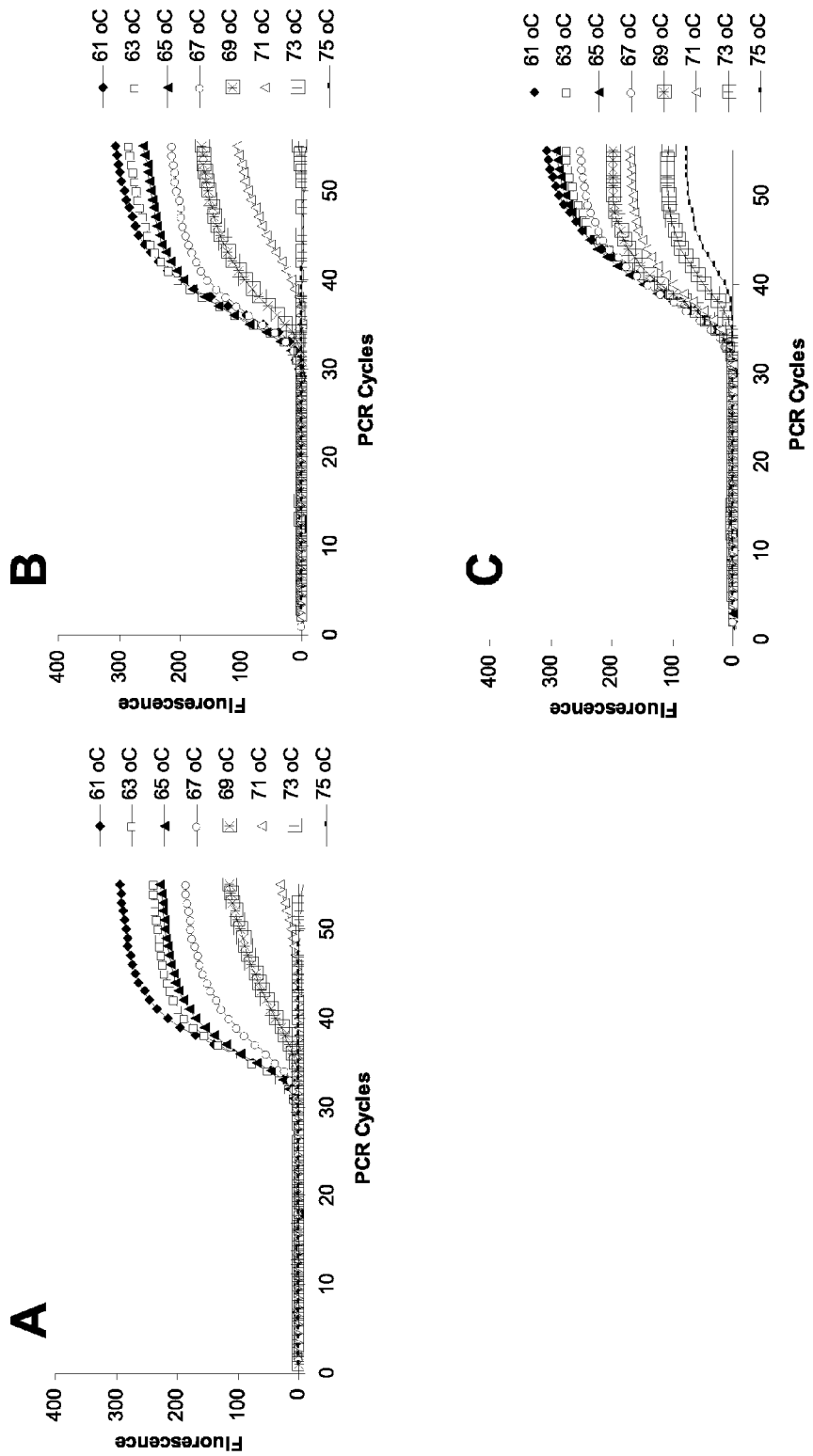
Figure 11:
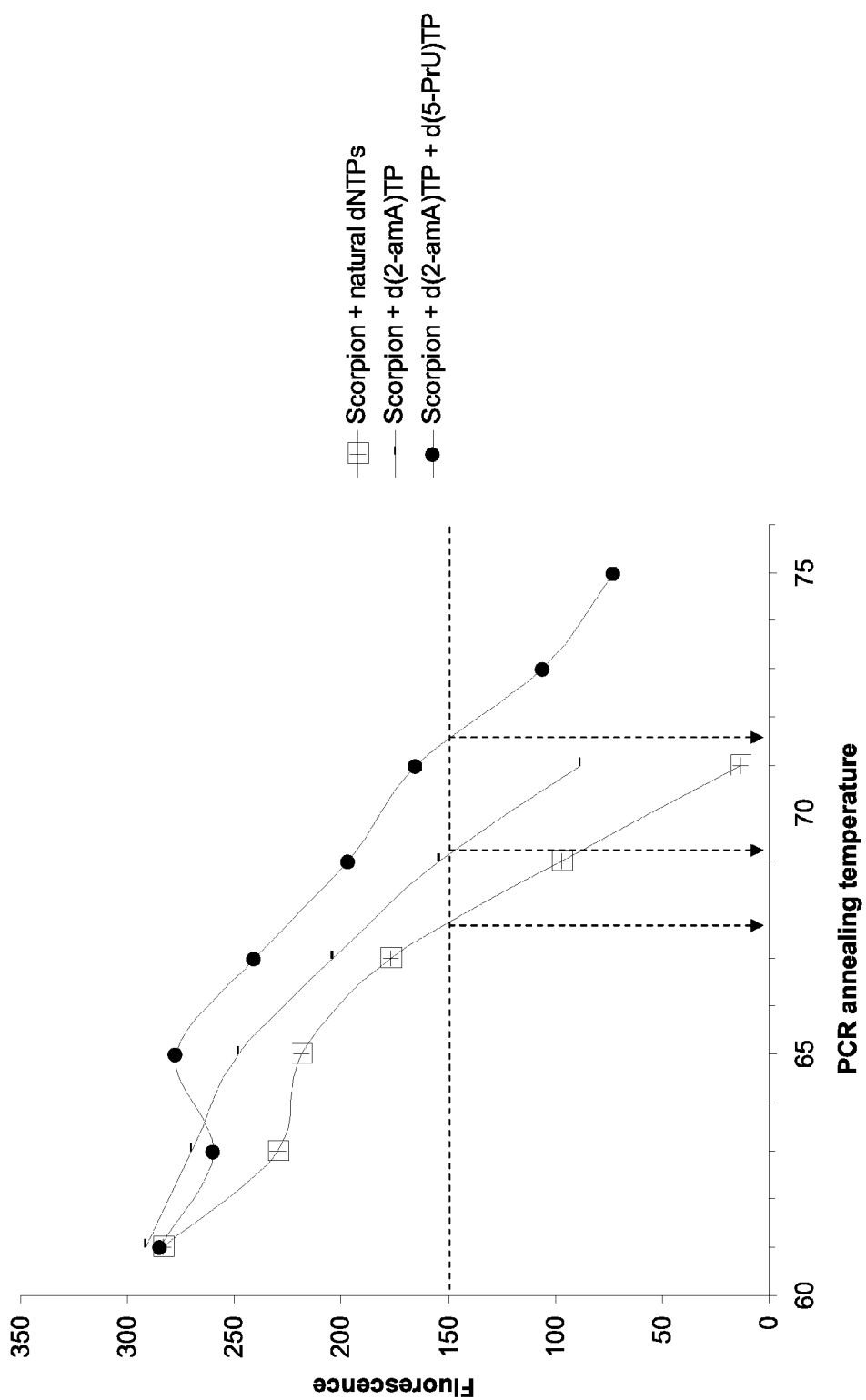

FIG. 11 shows signal performance of the scorpion assays from FIG. 10 versus annealing temperature of PCR. Fluorescence of every individual reaction at PCR cycle 50 was plotted against the annealing temperature used in that reaction. Arrows point to the annealing temperatures at which approximately half of the assay signal (150 fluorescence units) has been reached.

SUMMARY OF ASPECTS OF THE INVENTION

Aspects of the present invention provide novel methods for the detection of nucleic acids, comprising nucleic acid amplification using base-modified deoxynucleoside 5'-triphosphates (dNTPs) as disclosed herein to provide for more stable amplification products.

Particular aspects provide a method for the detection of a target nucleic acid in a sample, comprising: amplification and detection reactions, wherein hybridization properties of oligonucleotide components used in said amplification and/or detection reaction are improved by amplifying modified DNA with enhanced hybridization properties in a reaction mixture comprising DNA polymerase and at least one base-modified duplex-stabilizing dNTP.

Additional aspects provide a method for the detection of a target nucleic acid in a sample, comprising: providing a reaction mixture comprising a target nucleic acid, at least one oligonucleotide primer, a DNA polymerase, and a mixture of deoxynucleoside 5'-triphosphates containing at least one base-modified duplex-stabilizing dNTP; amplifying the target nucleic acid, wherein the at least one base-modified duplex-stabilizing dNTP incorporates into amplicons providing copies of a modified DNA with enhanced hybridization properties, and wherein said modified DNA serves as a template for the at least one oligonucleotide primer at any stage of the amplification; and detecting the modified DNA, wherein the presence of the modified DNA is indicative as to the presence of the target nucleic acid in said sample.

Further aspects provide a method for the detection of a target nucleic acid in a sample, comprising: providing a reaction mixture comprising a target nucleic acid, at least one oligonucleotide primer, a DNA polymerase, and a mixture of deoxynucleoside 5'-triphosphates containing at least one base-modified duplex-stabilizing dNTP; amplifying the target nucleic acid wherein the at least one base-modified duplex-stabilizing dNTP incorporates into amplicons providing copies of a modified DNA with enhanced hybridization properties; providing at least one oligonucleotide probe; hybridizing the at least one oligonucleotide probe to the modified DNA to form a complex; and detecting the complex wherein presence of the complex is indicative of the presence of the target nucleic acid in the sample.

Yet additional aspects provide a method for the detection of a target nucleic acid in a sample, comprising: amplifying the target nucleic acid using detection PCR in a reaction mixture comprising: a target nucleic acid, at least two oligonucleotide primers sufficient to provide for exponential amplification of the target nucleic acid, a DNA polymerase, and a mixture of deoxynucleoside 5'-triphosphates containing at least one base-modified duplex-stabilizing dNTP, wherein the at least one base-modified duplex-stabilizing dNTP incorporates into amplicons providing copies of a modified DNA with enhanced hybridization properties; and detecting said modified DNA using at least one oligonucleotide probe that hybridizes to said modified DNA to form a complex, and detecting the complex, wherein presence of the complex is indicative of the presence of the target nucleic acid in the sample.

In particular aspects of the various embodiments, the target nucleic acid is DNA. In other aspects, the target nucleic acid is RNA. In certain aspects, the target nucleic acid is RNA and amplifying of the target nucleic acid includes a stage wherein at least one DNA copy of said RNA is synthesized using a reverse transcriptase. In some aspects, more than one oligonucleotide primer is used to amplify the target nucleic acid, and wherein the modified DNA serves as a template for at least one of said oligonucleotide primers at any stage of the amplification. In additional aspects, more than one target nucleic acid are amplified and detected. In certain embodiments, at least one oligonucleotide primer is provided for every target nucleic acid amplified and detected. In particular embodiments, more than one of the oligonucleotide primers is provided for every said target nucleic acid amplified and detected and wherein at least one of the modified DNAs serves as a template for at least one of said oligonucleotide primer at any stage of the amplification. In certain aspects, detection of the target nucleic acid is performed after the amplification. In other aspects, detection of the target nucleic acid is performed in real time. In certain embodiments, the base-modified duplex-stabilizing dNTP completely replaces the respective natural dNTP. In other embodiments, the base-modified duplex-stabilizing dNTP represents a fraction of the respective natural dNTP. In certain aspects, the reaction mixture comprises more than one of the base-modified duplex-stabilizing dNTP, in each case either replacing or representing a fraction of the respective natural dNTP. In certain aspects, the base-modified duplex-stabilizing dNTP is of Formula I:

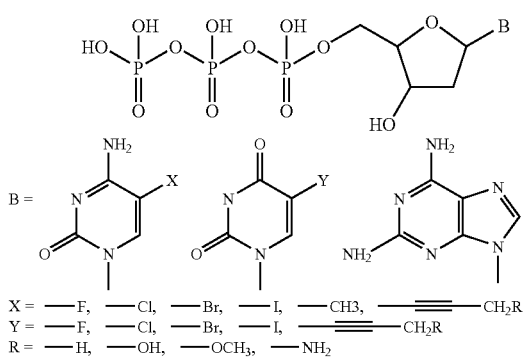

In certain embodiments, amplifying and detecting of the target nucleic acid is performed to measure the amount of said target nucleic acid in said sample. In particular implementations, amplifying of the target nucleic acid comprises use of isothermal amplification. In other aspects, amplifying of the target nucleic acid comprises use of detection PCR. In certain embodiments, at least one of the oligonucleotide primer, oligonucleotide probe, and/or modified DNA contains a label and wherein this label affords detecting of the modified DNA. In certain aspects, the label is a fluorescent label. In some embodiments, the label comprises a fluorescence-polarization label. In other aspects, the at least one oligonucleotide primer or the at least one oligonucleotide probe or both of them contain one or more structural modifications. In some embodiments, the structural modifications comprise duplex-stabilizing modifications. In certain aspects, the duplex-stabilizing modifications comprise modified nucleotides. In additional aspects, the duplex-stabilizing modification comprises a tail conjugated to 5'-end of said oligonucleotide primer. In certain embodiments, the tail comprises an intercalator. In other embodiments, the tail comprises a minor groove binder. In particular embodiments, detecting the modified DNA comprises use of a detecting agent, wherein the detecting agent interacts with the modified DNA providing a detection signal, and wherein detection of the signal is indicative of the presence of the modified DNA in the reaction mixture. In some aspects, the detecting agent comprises a fluorescent agent. In certain embodiments, the fluorescent agent changes its fluorescence properties upon interaction with said modified DNA thereby providing the detection signal. In certain aspects, the fluorescent agent comprises a SYBR Green dye.

In certain aspects, the at least one oligonucleotide primer and the at least one oligonucleotide probe are portions or fragments of the same molecule. In particular embodiments, the oligonucleotide probe is a FRET probe, wherein the FRET probe changes its fluorescent properties upon forming the complex with the modified DNA, and wherein the changes are indicative of the presence of the complex. In some aspects, the FRET probe comprises a hybridization-triggered FRET probe. In other aspects, the hybridization-triggered FRET probe is a Scorpion primer. In certain embodiments, the hybridization-triggered FRET probe comprises a Beacon probe. In other embodiments, the FRET probe comprises a cleavable FRET probe. In certain aspects, the cleavable FRET probe comprises a TaqMan™ probe.

In some aspects, the at least one of the oligonucleotide primer, oligonucleotide probe and/or modified DNA is immobilized on a solid support at the amplifying or detecting stages, or at both stages.

Further embodiments provide a kit to perform the methods of any one of disclosed methods, wherein said kit comprises (i) at least one base-modified duplex-stabilizing dNTP and (ii) at least of one of the components: oligonucleotide primer; DNA polymerase; and detecting agent. In certain aspects, the kit comprises: at least one base-modified duplex-stabilizing dNTP; and at least of one of the components selected from oligonucleotide primer, oligonucleotide probe, and DNA polymerase. Additional kit embodiments comprise: at least one base-modified duplex-stabilizing dNTP; and at least of one of the components selected from: two oligonucleotide primers, wherein said oligonucleotide primers are designed to provide exponential amplification of said target nucleic acid; at least one oligonucleotide probe; and a DNA polymerase.

DETAILED DESCRIPTION OF THE INVENTION

Aspects of the present invention provide novel methods for the detection of nucleic acids, comprising nucleic acid amplification using base-modified deoxynucleoside 5'-triphosphates (dNTPs) as disclosed herein (e.g., including those of exemplary FIGS. 2-11).

Definitions

As used herein, terms and symbols of biochemistry, nucleic acid chemistry, molecular biology and molecular genetics follow those of standard treaties and texts in the field, for example, Sambrook et al, Molecular Cloning: A Laboratory Manual, $2^{nd}$ Edition (Cold Spring Harbor Laboratory, 1989); Kornberg and Baker, DNA Replication, Second Edition (W. H. Freeman, New York, 1992); Gaits, ed., Oligonucleotide Synthesis: A Practical Approach (IRL Press, Oxford, 1984); Lehninger, Biochemistry, Second Edition (Worth Publishers, New York, 1975); Eckstein, ed., Oligonucleotides and Analogs: A Practical Approach (Oxford University Press, New York, 1991); and the like. Additionally, to facilitate understanding of the invention, a number of terms are defined herein.

The term, "sample" as used herein refers to any substance containing or presumed to contain a nucleic acid of interest, and thus includes a sample of nucleic acid, cells, organisms, tissue, fluids (e.g., spinal fluid or lymph fluids), and sample including but not limited to plasma, serum, urine, tears, stool, respiratory and genitourinary tracts, saliva, fragments of different organs, tissue, blood cells, samples of in vitro cell cultures, isolates natural from natural sources such as drinking water, microbial specimens, and objects or specimens that have been suspected to contain nucleic acid molecules.

The terms, "target nucleic acid" or "nucleic acid of interest" refers to a nucleic acid or a fragment of nucleic acid that is to be amplified and detected using one or more methods of the present invention. Two or more target nucleic acids can be, for example, fragments of the same nucleic acid molecule or of different nucleic acid molecules. As used herein, target nucleic acids are different if they do not match in nucleotide sequence by at least one nucleotide. In this aspect, aspects of the invention may be used to detect polymorphic variations wherein, for example, two nucleic acids of interest have a significant degree of identity in the sequence but differ by few nucleotides (e.g. insertions, deletions) or by a single nucleotide (SNP). The target nucleic acids of the present inventive aspects may be derived from any organism or other source, including but not limited to prokaryotes, eukaryotes, plants, animals, and viruses, as well as synthetic nucleic acids. The target nucleic acids may contain DNA, RNA, and/or variants or derivatives thereof. Target nucleic acids can be single-stranded or double-stranded, and when a nucleic acid of interest is, or presumed to be double-stranded, the term "target nucleic acid" refers to a specific sequence in either strand of the double-stranded nucleic acid. Therefore, a full complement to any single-stranded nucleic acid of interest is treated for particular embodiments herein as the same target nucleic acid. In certain embodiments, the "target nucleic acid" resides between two primer sequences used for amplification and detection. In particular aspects, the nucleic acid of interest is isolated and purified from a sample source before applying methods of the present invention. Preferably, the target nucleic acids are sufficiently free of proteins and/or any other substances that interfere with the inventive amplification and detection reactions. Many art recognized methods are available for the isolation and purification of target nucleic acids, including commercial kits and specialty instruments. For example, nucleic acids can be isolated using organic extraction with a phenol/chloroform organic reagent followed by ethanol precipitation (Ausubel et al., eds., Current Protocols in Molecular Biology Vol. 1, Chapter 2, Section I, John Wiley & Sons, New York (1993). Solid phase adsorption method (Walsh et al. (1991) *Biotechniques,* 10:506-513, Boom et al., U.S. Pat. No. 5,234,809) and salt-induced DNA precipitation (Miller et al (1988) Nucleic Acids Res., 16:1215) are yet other known approaches to purify nucleic acids. Typically, amounts of nucleic acids of interest present in samples are limited, and the target nucleic acid needs, therefore, to be amplified using a suitable amplification procedure to facilitate detection using the inventive methods.

The terms "amplification" and "amplifying" a target nucleic acid as used herein refers to a procedure wherein multiple copies of the nucleic acid of interest are generated, for example, in the form of DNA copies. Many methods and protocols are known in the art to amplify target nucleic acids.

The term "Amplicon" refers to a product or products of a polynucleotide amplification reaction, and may refer to a population of polynucleotides, single or double-stranded, that are replicated from one or more nucleic acids of interest. Amplicons may be produced by a variety of amplification reactions whose products are multiple replicates comprising one or more target nucleic acids.

Amplification can be "isothermal," as used herein wherein the temperature of the amplification reaction does not significantly change or fluctuate. Examples of these techniques include, but are not limited to: strand displacement amplification (SDA) (Walker G. T. et al, U.S. Pat. No. 5,270,184; Dattagupta N. et al, U.S. Pat. No. 6,214,587; Walker G. T. et al (1996) *Nucleic Acids Res.,* 24, 384-353); rolling circle amplification (RCA) (Lizardi P., U.S. Pat. No. 5,854,033); linear target isothermal multimerization and amplification (LIMA) (Hafner G. J. et al (2001) *BioTechniques,* 30:852-867); loop-mediated amplification (LMA) (Notomi T. and Hase T., U.S. Pat. No. 6,410,278; Notomi T. et al (2000) *Nucleic Acids Res.,* 28, e63); isothermal amplification using chimeric or composite RNA/DNA primers (Cleuziat P. and Mandrand B., U.S. Pat. No. 5,824,517; Kurn N. (2001) U.S. Pat. No. 6,251,639); and other methods. Amplification technologies may include synthesis and amplification of RNA molecules along with amplification of DNA sequences, for example, Nucleic Acid Sequence-Based Amplification (NASBA) (Oehlenschlager F. et al (1996) *Proc. Natl. Acad. Sci. USA,* 93: 12811-12816; Davey C. and Malek L. T., U.S. Pat. No. 6,063,603). It will be appreciated that art-recognized amplification technologies vary in aspects of the design, complexity, efficiency, specificity, accuracy and other parameters relevant and important in nucleic acids detection. For example, amplification may be linear or exponential as a function of time (and/or cycles in PCR).

In preferred embodiments, amplification of the target nucleic acids is accomplished using the "polymerase chain reaction" ("PCR") (Mullis K. B. et al, U.S. Pat. No. 4,683,195; Mullis K. B., U.S. Pat. No. 4,683,202). The most commonly used PCR profile employs two oligonucleotide primers, one for each strand, which are designed so that the extension of one primer provides a template for the other primer in the next PCR cycle. Generally, a PCR consists of repetition (or cycles) of (i) a denaturation step that separates the strands of a double-stranded nucleic acid comprising a target sequence, followed by (ii) an annealing step that allows primers to anneal to positions flanking the target sequence; and (iii) an extension step that extends the primers in a 5' to 3' direction, thereby forming an 'amplicon' nucleic acid having sequences complementary to the target sequence. Each of the above three steps may be conducted at a different temperature using an automated thermocycler. The PCR cycles can be repeated as many times as desired, resulting, at least in theory, in an exponential accumulation of a target DNA fragment whose termini are defined by the 5' ends of the primers used. Particular temperatures, incubation times at each step, and rates of change between steps depend on many factors well-known to those of ordinary skill in the relevant art, and relevant examples can be found in numerous published protocols; for example, McPherson M. J. et al. (1991 and 1995) and the like. Although conditions of PCR can vary over a broad range, in a conventional PCR, a double-stranded target nucleic acid is denatured at temperature>90° C., primers are annealed at a temperature in the range 50-75° C., and the extension is preferably performed in the range 72-78° C. As for PCR used in nucleic acid detection, amplification specificity and time are important factors. Therefore, in preferred embodiments, nucleic acids are amplified and detected using "detection PCR."

The term "detection PCR" as used herein refers to PCR which is performed to amplify and to detect one or more target nucleic acids, and which preferably meets two requirements (1) the cycle time of the detection PCR is at least 10 minutes or less (preferably it is less than 5 minutes, and even more preferably less than 2 minutes); and (2) the lowest temperature within the detection PCR cycles (usually annealing temperature) must be at least 50° C. or greater (preferably this temperature is above 55° C., more preferably above 60° C., and even more preferably above 65° C.). As shown in the examples herein, aspects of the present invention substantially improve hybridization properties of oligonucleotide components used in nucleic acid amplification and detection. This, in turn, allows for increasing of the annealing temperature of PCR to the temperature values that are optimal for primer extension (e.g., 72-75° C.) by thermostable DNA polymerases, thereby enabling "merging" of the annealing and extension stages. Thus, in a preferred embodiment, PCR is performed in two stages, (i) a strand denaturation stage, and (ii) a combined annealing/extension stage. The number of the PCR cycles necessary to provide a detectable target nucleic acid concentration depends on the initial target nucleic acid load (amount), which is typically unknown, and amplification yield at the respective PCR cycles. The term "detection PCR" encompasses derivative forms of the reaction, including but not limited to, "RT-PCR," "real time PCR," "nested PCR," "quantitative PCR," "multiplexed PCR," and the like.

In particular embodiments, PCR amplification and detection of target nucleic acid is accomplished using one oligonucleotide primer. This approach provides linear amplification of a target nucleic acid and it requires substantially more of the initial target load or alternatively substantially more PCR cycles to reach amplification levels comparable to exponential PCR design.

When the nucleic acid of interest is RNA, it can be converted by known methods to DNA/RNA heteroduplexes or to duplex cDNA prior to PCR; for example, as described in Simpson D. et al (1988) *Biochem. Biophys. Res. Commun.,* 151:487-492 and Belyaysky A. et al (1989) *Nucleic Acids Res.,* 17: 2919-2932 and the like. These methods employ a "reverse transcriptase" enzymatic activity that can extend an oligonucleotide primer hybridized to a RNA template, providing for synthesis of complementary DNA (cDNA) in presence of deoxynucleoside 5'-triphosphates (dNTPs); namely, "reverse transcription PCR" or "RT-PCR" as described in U.S. Pat. No. 5,168,038 to Tecott L. et al (1992), which is incorporated herein by reference in its entirety.

In certain preferred aspects, detection of the target nucleic acids can be performed in "real time." Real time detection is possible when all detection components are available during the target amplification, and the reaction conditions (e.g., temperature, buffering agents, salts, co-factors, scavengers, and the like) support both stages of the reaction—amplification and detection, thereby permitting a target nucleic acid to be measured as the amplification reaction progresses decreasing the number of subsequent handling steps required for the detection of amplified material. Therefore, the term "Real-time PCR" as used herein refers to PCR in which the amount of reaction product, e.g., amplified target nucleic acid, is monitored as the reaction proceeds. Real-time PCR differs primarily in the detecting chemistries for monitoring the target nucleic amplification in the reaction, for example: Gelfand et al, U.S. Pat. No. 5,210,015 describe use of 5'-nuclease cleavable FRET probes ("TaqMan"); Tyagi et al, U.S. Pat. No. 5,925,517 use hybridization-triggered FRET probes ("Beacons"), both of which are incorporated herein by reference. Reviews of the detection chemistries for real time PCR can be also found in Didenko V. V. (2001) *BioTechniques,* 31: 1106-1121; Mackay I. M. et al (2002) *Nucleic Acids Res.,* 30 1292-1305, and Mackay J., Landt O. (2007) *Methods Mol. Biol.,* 353 237-262, which are also incorporated herein by reference.

The term "nested PCR" as used herein refers to a two-stage PCR wherein the amplification product of a first PCR becomes the sample for a second PCR using a new set of primers, at least one of which binds to an interior location of the amplification product of first PCR.

The term "multiplexed PCR" as used herein refers to a PCR wherein multiple target nucleic acids are simultaneously amplified and detected. Usually, this PCR employs sets of target-specific primers for each sequence being amplified.

The term "quantitative PCR" as used herein means a PCR designed to measure the abundance of one or more specific target sequences in a sample. Quantitative measurements are made using one or more reference nucleic acid sequences which may be assayed separately or together with a target nucleic acid. Techniques for quantitative PCR are well-known in the art and they are exemplified in the following manuscripts that are incorporated herein by reference: Gu Z. et al (2003) *J. Clin. Microbiol.*, 41:4636-4641; Becker-Andre M. and Hahlbrock K. (1989) *Nucleic Acids Res.*, 17:9437-9446; Freeman W. M. et al (1999) *Biotechniques*, 26:112-122, 124-125; Lutfalla G. and Uze G. (2006) *Methods Enzymol.*, 410:386-400; Clementi M. et al (1993) *PCR Methods Appl.* 2:191-196; Diviacco S. et al (1992) *Gene*, 122:313-320.

The term "detecting agent" as used herein refers in particular aspects to any molecule or particle which associates with nucleic acids in a specific fashion and wherein this association complex may be detected by any physical, chemical or biological means. The most commonly used detecting agents are intercalating dyes and fluorescent agents. For example, amplification products in PCR can be detected using intercalating dyes as described by Wittwer C. T. et al in U.S. Pat. Nos. 6,174,670 and 6,569,627.

The term "fluorescent agent" means a detecting agent that provides a fluorescence signal. The preferred fluorescent agents are those molecules that change fluorescence properties upon the interaction with nucleic acids providing detectable signal. SYBR Green I and II from Invitrogen are examples of commonly used fluorescent agents as described in Schneeberger C. et al (1995) *PCR Methods Appl.*, 4:234-238 and Mackay J., Landt O. (2007) *Methods Mol. Biol.*, 353:237-262.

The term "polynucleotide" and "oligonucleotide" are used interchangeably herein, and each means a linear polymer of nucleotide monomers. Polynucleotides typically range in size from a few monomeric units, e.g. 5-40, when they are usually referred to as "oligonucleotides," to several thousand monomeric units. The exact size will depend on many factors, which in turn depends on the ultimate function or use of the oligonucleotide. The oligonucleotide may be generated in any manner, including chemical synthesis, DNA replication, reverse transcription, or a combination thereof. Whenever a polynucleotide or oligonucleotide is represented by a sequence of letters, for example, "CCGTATG," it is understood herein, unless otherwise specified in the text, that the nucleotides are in 5'→3' order from left to right and that "A" denotes deoxyadenosine, "C" denotes deoxycytidine, "G" denotes deoxyguanosine, and "T" denotes deoxythymidine, unless otherwise indicated or obvious from context. Usually DNA polynucleotides comprise these four deoxyribonucleosides linked by phosphodiester linkage whereas RNA comprise four their ribose counterparts with uridine ("U") in place of "T".

The term "natural nucleosides" as used herein refers to four deoxynucleosides which may be commonly found in DNAs isolated from natural sources. Natural nucleosides are deoxyadenosine, deoxycytidine, deoxyguanosine, and deoxythymidine. The term also encompasses their ribose counterparts, with uridine in place of thymidine.

As used herein, the term "unnatural nucleosides" refers to nucleoside analogs that by any way are different in their structure from those natural nucleosides for DNA and RNA polymers. Some of the naturally occurring nucleic acids of interest may contain nucleosides that are structurally different from the natural nucleosides defined above, for example, DNAs of eukaryotes may incorporate 5-methyl-cytosine and tRNAs are notorious for harboring some of the nucleoside analogs. However, as used herein in particular aspects, the term "unnatural nucleosides" nonetheless encompasses these nucleoside modifications even though they can be found in natural sources. For example, ribothymidine is treated herein as an unnatural nucleoside.

The term "natural dNTP" refers to a deoxynucleoside 5'-triphoshate representing one of the four natural nucleosides as defined above.

Figure 3:
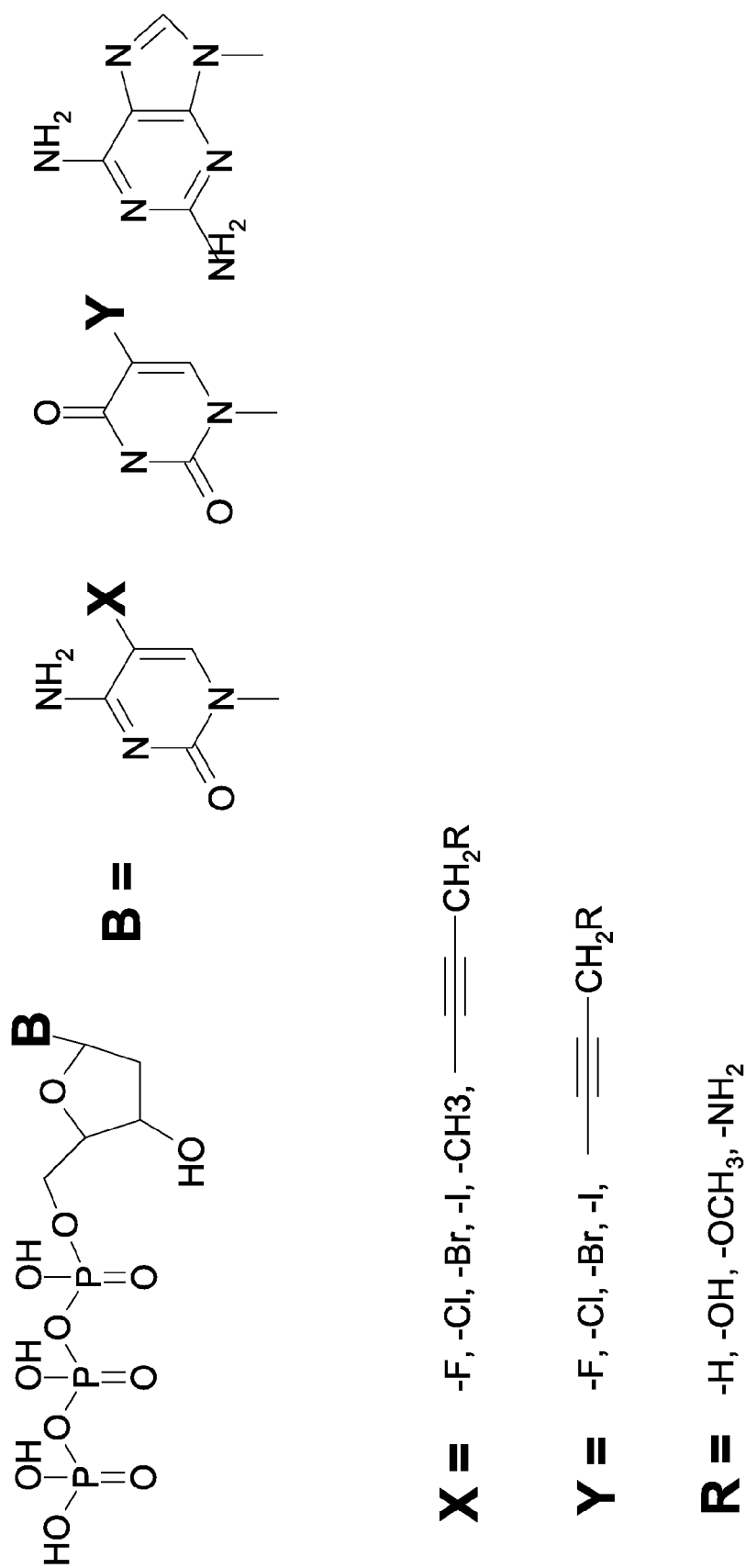
FIG. 3 shows structures of base-modified 2'-deoxynucleoside 5'-triphosphates used in exemplary aspects of the present invention. "B" refers to modified bases, and "X" and "Y" are 5-position substitution moieties.

The term "base-modified duplex-stabilizing dNTP" as used herein refers to a deoxynucleoside 5'-triphoshate which contains an unnatural base (base-modified) and which, when incorporated into a polymer with other dNTPs in presence of DNA polymerase, provides a modified DNA with enhanced hybridization properties (duplex-stabilizing). Examples of base-modified duplex-stabilizing dNTPs, according to exemplary aspects, are shown in FIG. 3. As used herein, a base-modified duplex-stabilizing dNTP is an analog of the respective natural dNTP, e.g. d(5-MeC)TP (5-methyl cytosine) is an analog of dCTP (cytosine), d(2-amA)TP (2-amino adenosine, also referred to as 2,6-diamino purine) is an analog of dATP (adenosine), etc. In certain embodiments, a base-modified duplex-stabilizing dNTP completely replaces the respective natural dNTP. This means, for example, that, if d(5-MeC)TP is used in the amplification reaction, the reaction does not contain dCTP. In other embodiments, a base-modified duplex-stabilizing dNTP represents a fraction of the respective natural dNTP. This means that both natural dNTP and its analog are present in the reaction mixture, and typically wherein the base-modified duplex-stabilizing dNTP represents, at least, 1/20 fraction (5%) of molar amount of the respective natural dNTP.

The term "oligonucleotide component" refers to any molecule of the polynucleotide nature that is required or helpful in conducting either amplification or detection reactions of the invention or both. Oligonucleotide components include but not limited to oligonucleotide primers, probes, hybridization and cleavage enhancers, effectors, etc. Oligonucleotide components can be labeled or have structural modifications including those used in oligonucleotide primer and probe designs.

The term "oligonucleotide primer" as used herein refers to a single-stranded DNA or RNA molecule that hybridizes to a target nucleic acid and primes enzymatic synthesis of a second nucleic acid strand in presence of a DNA polymerase. In this case, as used herein, the target nucleic acid "serves as a template" for the oligonucleotide primer. An "oligonucleotide primer" may occur naturally, as in a purified restriction digest or may be produced synthetically. In particular aspects, a primer is selected to have on its 3' end a region that is substantially complementary to a strand of specific sequence of the template. A primer must be sufficiently complementary to hybridize with a template strand for primer elongation to occur. An oligonucleotide primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed within the primer, provided that the primer sequence has sufficient complementarity with the sequence of the template to hybridize and thereby form a template-primer complex for synthesis of the extension product of the oligonucleotide primer.

As used herein, the term an "oligonucleotide probe" refers to an oligomer or polymer used in detecting a target nucleic acid that forms a duplex structure or other complex with the target nucleic acid, based on complementarity of at least one sequence in the probe with a sequence in the target nucleic acid. Oligonucleotide primers and probes of the present invention can be "modified" or contain "structural modifications."

The term "structural modifications" refers to any chemical substances such as atoms, moieties, residues, polymers, linkers or nucleotide analogs which are usually of a synthetic nature and which are not commonly present in natural nucleic acids. As used herein, the term "structural modifications" also include nucleoside or nucleotide analogs which are rarely present in natural nucleic acids, and include but are not limited to inosine (hypoxanthine), 5-bromouracil, 5-methylcytosine, 5-iodouracil, 2-aminoadenosine, 6-methyladenosine, preudouridine and the like.

"Duplex-stabilizing modifications" refer to structural modifications, which when present in double-stranded nucleic acids provide duplex-stabilizing effects when compared in terms of thermal stability, usually measured as Tm, with the respective nucleic acid complexes that have no structural modification, e.g. comprising of natural nucleotides. Duplex-stabilizing modifications are structural modifications that are most commonly applied to the synthesis of oligonucleotide probes and primers. Those of ordinary skill in the art will appreciate that there are certain rules and limits to use of the structural modifications in oligonucleotide primers. The 3' end of the primers must not be blocked to allow for initiation of DNA synthesis. For example, when minor groove binders (MGB) are conjugated to enhance the primer hybridization properties, the MGB moiety is usually coupled to the 5' end (Afonina I. et al (1997) *Nucleic Acids Res.*, 25:2657-2660). Certain nucleotide analogs can be incorporated into the oligonucleotide primers, although the number of these modifications is limited. Examples of such nucleotide analogs include but not limited to "universal" bases (Burgner D. et al (2004) *Nucleosides Nucleotides Nucleic Acids*, 23:755-765) and "locked nucleic acids" ("LNA") (Latorra D. et al (2003) *Mol. Cell. Probes*, 17:253-259; Latorra D. et al (2003) *Hum. Mutat.*, 22:79-85; Di Giusto D. A. and King G. C. (2004) *Nucleic Acids Res.*, 32:e32), in accordance with teachings of the cited references which are incorporated herein by reference. Certain base-modified nucleotide analogs are well tolerated by DNA polymerases and these analogs can be used in primer design without any limits. Examples of such base-modified nucleotide analogs include but not limited to 5-methyl cytosine and diamino purine (Lebedev Y. et al (1996) *Genet. Anal.*, 13: 15-21). Unlike the oligonucleotide primers, oligonucleotide probes may have no limits in use of the structural modifications. For example, according to Ortiz E. et al (1998) *Mol. Cell. Probes*, 12:219-226, the oligonucleotide probes can be completely made of unnatural "peptide nucleic acid" ("PNA") monomers; as these probes have no natural nucleotides in their structures. Application of other base-modified (Lebedev Y. et al (1996) *Genet. Anal.*, 13: 15-21) or sugar-modified nucleotide analogs like LNA (Johnson M. P. et al (2004) *Nucleic Acids Res.*, 32: e55; Simeonov A. and Nikiforov T. T. (2002) *Nucleic Acids Res.*, 30:e91) is also widely applicable to probes. Oligonucleotide probes can carry an MGB moiety conjugated at either end. For example, 5'-MGB-conjugated FRET probes are not cleaved in detection PCR and these probes provide a signal due to a hybridization-triggered mechanism of action as described in Vermeulen N. et al (2002) *J. Clin. Ligand Assay*, 25:268-275. By contrast, 3'-MGB-conjugated FRET probes are not blocked from 5'-nuclease degradation and these probes generate fluorescent signals due to cleavage by Taq polymerase as exemplified in Kutyavin I. V. et al (2000) *Nucleic Acids Res.*, 28: 655-661.

"Hybridizing," "hybridization" or "annealing" as used herein refers to a process of interaction between two or more polynucleotides forming a complementary complex through base pairing which is most commonly a duplex or double-stranded complex as originally described in Marmur J., Lane D. (1960) *Proc. Natl. Acad. Sci. USA*, 46:453-461 and Doty P. et al (1960) *Proc. Natl. Acad. Sci. USA*, 46:461-476. The stability of a nucleic acid duplex is measured by the melting temperature, or "$T_m$." The $T_m$ of a particular nucleic acid duplex under specified conditions is the temperature at which, on average, half of the base pairs have disassociated.

"Hybridization properties" of a polynucleotide refers to the ability of this polynucleotide or a fragment thereof to form a sequence-specific complex with another complementary polynucleotide or its fragment. "Hybridization properties" also generally refers herein to the complementary complex stability. In this aspect, "hybridization properties" is used in a similar fashion to "melting temperature" or "Tm."

"Improved" or "enhanced hybridization properties" of a polynucleotide, as used herein, refers to an increase in stability of a complex of this polynucleotide with its complementary sequence because of any factor, including but not limited to a change in reaction conditions such as pH, salt concentration and composition (e.g., an increase in magnesium ion concentration, presence of complex stabilizing agents such as intercalators or minor groove binders, etc.). The hybridization properties of a polynucleotide or oligonucleotide can be also altered by an increase or decrease in polynucleotide or oligonucleotide length. The cause or basis of the hybridization property enhancement is usually found in context herein. The hybridization properties of a polynucleotide can also be enhanced by a structural modification of the polynucleotide. For example, use of base-modified duplex-stabilizing dNTPs in assays of the present invention leads to amplification of a modified DNA wherein this modified DNA is said to have enhanced hybridization properties. This is the most common use of the term "enhanced hybridization properties" as used herein. This means that the thermal stability or Tm of a complementary complex of this modified DNA with, for example, oligonucleotide probes or primers, is greater than that of a DNA comprising respective natural bases.

"Melting temperature" or "Tm" refers to the temperature at which a complementary complex of nucleic acids, usually double-stranded, becomes half dissociated into single strands. These terms are also used in describing stabilities of polynucleotide secondary structures wherein two or more fragments of the same polynucleotide interact in a complementary fashion with each other forming complexes, e.g., hairpin-like structures, etc. A simple estimate of the Tm value may be calculated using the equation Tm=81.5+0.41(% G+C), when a nucleic acid is in aqueous solution at 1 M NaCl. More accurate calculations can be made using the base pair thermodynamics of a "nearest-neighbors" approach (Breslauer K. J. et al (1986) *Proc. Natl. Acad. Sci. USA*, 83:3746-3750; SantaLucia J. Jr. (1998) *Proc. Natl. Acad. Sci. USA*, 95:1460-1465).

The term "label" refers to any atom or molecule that can be used to provide a detectable signal and that can be attached to a nucleic acid or oligonucleotide. Labels include but are not limited to isotopes, radiolabels such as $^{32}P$; binding moieties such as biotin; haptens such as dioxygenin; luminogenic, mass tags; phosphorescent or fluorescent moieties, fluorescent dyes alone or in combination with other dyes or moieties that can suppress or shift emission spectra by FRET effect.

Labels may provide signals detectable by fluorescence, radioactivity, colorimetry, gravimetry, X-ray diffraction or absorption, magnetism, enzymatic activity, mass spectrometry, binding affinity and the like. A label may be a charged moiety or alternatively, may be charge neutral. Labels can include or consist of nucleic acid or protein sequence, so long as the sequence comprising the label is detectable.

"Fluorescent label" refers to a label that provides a fluorescent signal. Fluorescent labels are commonly fluorescent dyes, but may comprise any molecule including but not limited to a macromolecule like protein or a particle made from inorganic material like quantum dots as described in Robelek R. et al (2004) *Anal. Chem.,* 76: 6160-6165.

"FRET" is an abbreviation of Förster Resonance Energy Transfer effect. FRET is a distance-dependent interaction occurring between two dye molecules in which excitation is transferred from a donor to an acceptor fluorophore through dipole-dipole interaction without the emission of a photon. As a result, the donor molecule fluorescence is quenched, and the acceptor molecule becomes excited. The efficiency of FRET depends on spectral properties, relative orientation and distance between the donor and acceptor chromophores (Förster T. (1965) Delocalized excitation and excitation transfer. In Sinanoglu, O. (ed.), *Modern Quantum Chemistry, Istanbul Lectures, part III.* Academic Press, New York: 93-137). In the case of random dipole orientation, and with a good overlap between emission spectrum of the donor and absorption spectrum of the acceptor, the efficiency of FRET is dependent on the inverse sixth power of the intermolecular separation (Clegg R. M. (1992) *Methods Enzymol.,* 211:353-388; Clegg R. M. (1995) *Curr. Opin. Biotech.,* 6:103-110; Selvin P. R. (1995) Methods Enzymol., 246:300-334). This makes FRET useful over distances comparable to the dimensions of biological macromolecules (Stryer L. and Haugland R. P. (1967) *Proc. Natl. Acad. Sci. USA,* 58:719-726) and this effect is widely used in biomedical research and particularly in probe designs for nucleic acid detection (Didenko V. V. (2001) *BioTechniques,* 31: 1106-1121).

As used herein, the term "FRET probe" refers to a fluorescent oligonucleotide which is used for detection of a nucleic acid of interest wherein detection is based on FRET effect. The FRET probe commonly contains two chromophores. The acceptor chromophore is usually a non-fluorescent dye chosen to quench fluorescence of the reporting fluorophore (Eftink M. R. (1991) In Lakowicz J. R. (ed.), *Topics in Fluorescence Spectroscopy.* Plenum Press, New York, V. 2:53-126). Formation of sequence specific hybrids between target nucleic acid and probes leads to a change in fluorescent properties of the probe providing detection of the nucleic acid target. Many detection designs exploring the FRET effect have been reported to date. The most common FRET probes that can be used to practice the present invention are: TaqMan™ (Lie Y. S. and Petropoulos C. J. (1998) *Curr. Opin. Biotech.,* 9:43-48; Livak K. J. et al (1995) *PCR Methods and Applications,* 4:357-362); Beacon (Tyagi S. and Kramer F. R. (1996) *Nat. Biotechnol.,* 14:303-308; Bonnet G. et al (1999) *Proc. Natl. Acad. Sci. USA,* 96: 6171-6176; Tyagi S. et al (2000) *Nat. Biotechnol.,* 18:1191-1196; Marras S. A. E. et al (2002) *Nucleic Acids Res.,* 30:e122; Piatek A. S. et al (1998) *Nat. Biotechnol.,* 16 359-363; Lewin S. R. et al (1999) *J. Virol.,* 73:6099-6103); Eclipse (Afonina I. A. et al (2002) *BioTechniques,* 32:940-949); Scorpion primers (Whitcombe D. et al (1999) *Nature Biotech.,* 17:804-807; Thelwell N. et al (2000) *Nucleic Acids Res.,* 28:3752-3761); self-quenching (Livak K. J. et al, U.S. Pat. No. 5,723,591) probes, and the cited manuscripts and patents are incorporated herein by reference. The FRET probe may comprise a single oligonucleotide molecule or more than one oligonucleotide; for example, Adjacent Hybridization probes (Heller M. J. and Morrison L. E. (1985) In Kingsbury, D. T. and Falkow, S. (eds.), *Rapid Detection and Identification of Infectious Agents.* Academic Press, New York, 245-256; Cardullo R. A. et al (1988) *Proc. Natl. Acad. Sci. USA,* 85:8790-8794; Gundry C. N. et al (1999) *Genet. Test.,* 3:365-370). A detailed review on various designs and applications of FRET oligonucleotide probes can be found in Didenko V. V. (2001) *BioTechniques,* 31: 1106-1121.

As used herein, "modified DNAs" refers to DNA incorporating at least one and preferably more than one base-modified duplex-stabilizing nucleotide. Amplification of modified DNAs is key component of the present invention. In preferred embodiments, target nucleic acids are detected by amplifying modified target DNAs using an oligonucleotide primers and DNA polymerase in presence of deoxynucleoside 5'-triphosphates (dNTPs) containing at least one base-modified duplex-stabilizing dNTP. However, as used herein "modified DNAs" may additionally contain any structural nucleotide modifications other than base-modified and duplex-stabilizing, if their presence is required by the choice of a specific amplification or detection reaction or providing DNAs with specific properties other than enhanced hybridization. For example, SDA amplification described in Walker G. T. et al (1993) U.S. Pat. No. 5,270,184 requires use of a α-thio dATP analog to promote nicking of one strand of double-stranded DNAs. Modified DNAs may additionally incorporate, for example, deoxyuridine (dU) monomer. Although this base modification is known to destabilize DNA duplexes, use of such modified DNAs is still within the scope of the present invention because the purpose of the dU application is usually in preventing contamination carryovers from sample to sample as described in Gelfand D. H. et al (1995) U.S. Pat. No. 5,418, 149.

A "reaction mixture" generally refers to a solution containing all the necessary reactants for performing an amplification or detection reaction or both, which in addition to main components such as target nucleic acids, DNA polymerases, oligonucleotide primers, probes or other oligonucleotide components, may include (but not limited to the inclusion of) detecting agents, specialty enzymes, nucleoside 5'-triphosphates including the modified ones, buffering agents to maintain pH at a selected level during a reaction, salts, co-factors and additives, for example, 1-methyl-2-pyrrolidinone, glycerol, poly(ethylene glycol), dimethyl sulfoxide or formamide and the like.

As used herein, the term "kit" refers to any system for delivering materials. In the context of reaction assays, such delivery systems include elements allowing the storage, transport, or delivery of reaction components such as oligonucleotides, buffering components, additives, reaction enhancers, enzymes and the like in the appropriate containers from one location to another commonly provided with written instructions for performing the assay. Kits may include one or more enclosures or boxes containing the relevant reaction reagents and supporting materials. The kit may comprise two or more separate containers wherein each of those containers includes a portion of the total kit components. The containers may be delivered to the intended recipient together or separately.

The term "solid support" refers to any material that provides a solid structure with which another material can be attached. Such materials may include but not limited to silicon, plastic, metal, glass, ceramic surfaces, and the like. Solid support may be of a rigid or non-rigid nature like gels, rubbers, polymers, etc. and it may be any type of shape including spherical shapes like beads. Certain embodiments of the present invention have at least on of the reaction components such as oligonucleotide primers, oligonucleotide probes or modified DNAs immobilized on solid support at amplifying or detecting stages or both. A biological material is "immobilized" to a solid support when it is associated with the solid support through a non-random chemical or physical interaction. The immobilization or attachment may be through a covalent bond using specialty spacer molecule or linker group. However, the immobilization need not be covalent or permanent.

As used herein, "detection assay" or "assay" refers a reaction or chain of reactions that are performed to detect nucleic acids of interest. The assay may comprise of multiple stages including amplification and detection reactions performed consequently or in real time, nucleic acid isolation and intermediate purification stages, immobilization, labeling, etc.

DETAILED DESCRIPTION OF EXEMPLARY ASPECTS

Particular aspects of the invention relate to improved methods for detecting nucleic acids, comprising amplifying and detecting modified nucleic acids (e.g. DNAs) with enhanced hybridization properties. In preferred aspects, the modified nucleic acids (e.g. DNAs) are produced and amplified by means of oligonucleotide primer extension in presence of a DNA polymerase and base-modified duplex-stabilizing dNTPs. The present inventive aspects benefit either amplification or detection stages or both, by stabilizing the complexes of oligonucleotide primers and probes with the modified DNAs.

In certain aspects, PCR is a preferred DNA amplification technology. In one aspect, the invention helps reduce the difference in stability between A/T and G/C base pairs, providing selective stabilization of A/T-rich duplexes, thus enabling assay designs that encompass detection of nucleic acid sequences which have been undetectable in conventional approaches.

In certain aspects, the invention allows for increasing the PCR reaction temperature to optimal conditions and accelerating the nucleic acids detection assays.

Additional aspects, allow for reducing the oligonucleotide primer and/or probe length wherein the length reduction is beneficial.

In a preferred embodiment, the invention relates to an improved real time PCR assay, wherein nucleic acids of interest are detected as the reaction proceeds using FRET probes.

In yet another preferred embodiment, the invention relates to an improved real time PCR assay that is performed to determine the amount of a target nucleic acid in a sample.

In particular embodiments, the invention provides improved methods for the amplification and detection of more than one nucleic acid of interest, e.g. multiplex PCR.

In general, the inventive aspects disclosed herein benefit virtually any nucleic acid detection assay that is based on synthesis, amplification and detection DNA molecules, provided that at least one oligonucleotide component (e.g., oligonucleotide primer(s) and probe(s)) hybridizes to the amplified DNAs during either the amplification or detection stages, or during both stages. According to aspects of the present invention, when an oligonucleotide component hybridizes to a modified DNA, it forms a complex (e.g. complementary duplex, extension complex for primers) and this complex is more stable by virtue of the modified DNA of the invention having enhanced the hybridization properties compared to conventional approaches wherein the DNA is not modified with duplex-stabilizing base analogs.

Those of ordinary skill in the art will appreciate that the present invention may benefit nucleic acid detection assays in a variety of ways, including but not limited to (i) expending and simplifying the design of oligonucleotide components for amplification or detection stages or both, (ii) implicating into design target nucleic acid sequences which were unapproachable (not assayable) using conventional approaches (e.g. due to an elevated A/T content), (iii) increasing the reaction temperature of either amplification or detection stages or both whenever it is possible (e.g. not restricted by thermal liability of key enzymes), (iv) accelerating either amplification or detection stages or both (e.g. assay time reduction), (v) allowing the use of shorter oligonucleotide components, thus reducing the cost of the oligonucleotide component manufacturing, etc.

In particular aspects, the methods reflect a number of factors determined by the choice of either DNA amplification or detection reactions, or combinations thereof. Numerous technologies have been reported to date for DNA amplification and detection, and the guidance to use the present invention is provided and exemplified herein as reference to the most recognized and commonly used techniques. Generally, the positive contribution (advantage) of the invention is anticipated to grow with increasing assay reaction temperatures, providing maximum benefit to those systems which are performed at temperatures exceeding 40° C., preferably 50° C., preferably 55° C., more preferably 60° C., more preferably 65° C. and even more preferably 70° C.

Application of the invention greatly benefits PCR-based detection assays. For example, the inventive aspects enable an increase in PCR temperature (annealing temperature) thereby speeding up the assays and moderating or essentially eliminating art-recognized PCR problems associated with misamplification (e.g. primer-dimer formation), and additionally improve the multiplexing capabilities of PCR.

The inventive aspects disclosed herein are easily practiced, and are cost effective compared with prior art technologies for enhancing hybridization properties of oligonucleotide primers and probes in nucleic acid detection assays (see "BACKGROUND" herein). Moreover, the present inventive aspects may be optionally and effectively combined with these conventional approaches as demonstrated in certain examples herein.

I. Amplification of Modified DNA with Enhanced Hybridization Properties

In certain embodiments, the modified DNAs with enhanced hybridization properties are amplified using an "isothermal amplification reaction." Isothermal DNA amplification reactions are normally performed at a steady or constant temperature. Examples of isothermal amplification reactions that can be useful in practicing the invention include but not limited to *Strand Displacement Amplification (SDA)* (Walker G. T. et al, U.S. Pat. No. 5,270,184; Dattagupta N. et al, U.S. Pat. No. 6,214,587; Walker G. T. et al (1996) *Nucleic Acids Res.*, 24:384-353; Walker G. T. et al (1992) *Proc. Natl. Acad. Sci. USA*, 89:392-396; Spargo C. A. et al (1996) *Molecular and Cellular Probes*, 10 247-256), *Rolling Circle amplification (RCA)* (Lizardi P., U.S. Pat. No. 5,854,033; Baner J. et al (1998) *Nucleic Acids Res.*, 26:5073-5078), *Linear Target Isothermal Multimerization and Amplification (LIMA)* (Hafner G. J. et al (2001) *BioTechniques*, 30:852-867), *Loop-Mediated Amplification (LMA)* (Notomi T. and Hase T., U.S. Pat. No. 6,410,278; Notomi T. et al (2000)

Nucleic Acids Res., 28, e63), isothermal amplification using chimeric or composite RNA/DNA primers (Cleuziat P. and Mandrand B., U.S. Pat. No. 5,824,517; Kurn N. (2001) U.S. Pat. No. 6,251,639), Nucleic Acid Sequence-Based Amplification (NASBA) (Oehlenschlager F. et al (1996) Proc. Natl. Acad. Sci. USA, 93:12811-12816; Davey C. and Malek L. T., U.S. Pat. No. 6,063,603), Helicase-Dependent Amplification (HAD) (Vincent M., Xu Y. and Kong H. (2004) EMBO reports, 5:795-800; An L., Tang W., Ranalli T. A., Kim H.-J., Wytiaz J., and Kong H. (2005) JBC, 280:28952-28958), all incorporated herein by reference, and many other methods. A review of the most commonly used isothermal amplification reactions can be found in Andras S. C. et al (2001) Mol. Biotechnol., 19:29-44, and detailed guidance to carry out the DNA amplification reaction regarding any particular amplification scheme of the choice can be found in the above cited references, which in turn contain references to other publications of the same subject nature and that can be also found useful for performing any particular amplification reaction.

In particular aspects, the modified DNAs with enhanced hybridization properties can be prepared using the isothermal technologies referenced above providing that at least one or preferably more than one of the natural dNTPs in those reactions are completely or partially substituted by the respective base-modified duplex-stabilizing dNTPs which are exemplified in FIG. 3.

In certain aspects, a modified DNA interacts with at least one and preferably more than one oligonucleotide primer in a sequence-specific fashion forming an extension complex (e.g. complementary duplex) and this complex is more stable by virtue of the modified DNA of the invention having enhanced hybridization properties compared to those conventional approaches wherein the DNA is not modified with duplex-stabilizing base analogs. These benefits the amplification stage in the ways discussed above. Those of ordinary skill in the Art will appreciate that certain adjustments or variations of the methods may apply to the use of the base-modified duplex-stabilizing dNTPs, depending on the nature of a particular amplification reaction, particularly those comprising enzymes other than DNA polymerase (restriction endonucleases, RNA polymerases, etc.). Applications of the base-modified duplex-stabilizing dNTPs will preferably not interfere with such other enzymatic activities where they are key components of the reaction or DNA synthesis. This may dictate the choice of the base-modified duplex-stabilizing dNTPs to be used in a particular amplification schemes and the choice may be made based on the properties of these enzymes, which are well known in the Art. For example, SDA amplification requires use of a α-thio dNTP analog to promote nicking only of one strand of double-stranded DNAs. Thus use of a respective base-modified duplex-stabilizing dNTP will preferably be avoided for such particular applications. Depending on the nature of the restriction endonucleases used in SDA; these enzymes may be sensitive, for example, to methylation of cytosine, and the use of 5-methyl-cytosine in preparation of modified DNA will preferably be limited or avoided. Guidance to properties of restriction endonucleases may be found in Ausubel F. M et al, eds., (1994) Current Protocols in Molecular Biology, Vol. 1, 9.1.1-9.1.3. Application of certain base-modified duplex-stabilizing dNTPs, for instance, 2,6-diaminopurine analog, may be limited in NASBA reactions because the use of such analogs may alter properties of the RNA polymerase promoter region required in the design of primers for this particular amplification. When desired, dTTP is replaced by a dUTP analog providing the respective modified DNA. This is a well known approach in preventing contamination carryovers from sample to sample as described in Gelfand D. H. et al (1995) U.S. Pat. No. 5,418,149. Application of such anti-carryover methods may reduce or limit the use of particular 5-substituted deoxyuridine dNTP analogs which are exemplified in FIG. 3.

Detection PCR is a preferred method for amplifying the modified DNAs of the present invention. In one embodiment, detection PCR may be performed using on oligonucleotide primer providing a linear amplification of the target modified DNAs. In a preferred embodiment, the detection PCR is conducted using two oligonucleotide primers which are designed to provide an exponential amplification.

An example of the PCR primer design is shown in FIG. 4. FIG. 4 shows sequences of a 96-mer target oligodeoxyribonucleotide (SEQ ID NO:24), forward (SEQ ID NO:25) and reverse (SEQ ID NO:26) PCR primers and a 22-mer fluorescent probe (SEQ ID NO:27) used in TaqMan® assays in exemplary aspects of the present invention. Scorpion assays were performed using the reverse primer (SEQ ID NO:26) and scorpion primer (SEQ ID NO:28) structure also shown. In the Scorpion primer (SEQ ID NO:28), a hairpin forming FRET probe (complementary end sequences are underlined) is connected to the 5'-end of the forward primer via a long and flexible C18-linker (Glen Research). The primers and probe used were made from all natural nucleosides, or alternatively incorporated modified bases. When base-modified oligonucleotides were used, the positions shown in bold-faced font were substituted with 2,6-diamino-purine or 5-methyl cytosine respectively. Underlined in the sequence of SEQ ID NO:24 is the binding site of the reverse primer (shown in reverse, 3'→5' orientation). "FAM" refers to 6-fluorescein and "Q" refers to BLACK HOLE QUENCHER™ (BHQ1) from Biosearch Technologies.

An example of reaction mixtures for detection PCR can be found in FIG. 5. FIGS. 5A-5D show exemplary results of fluorescence monitoring obtained for TaqMan® detection assays during real-time PCR on a SmartCycler™ (Cepheid). Structures of the target oligonucleotide (SEQ ID NO:24), forward (SEQ ID NO:25) and reverse (SEQ ID NO:26 PCR primers and TaqMan® probe (SEQ ID NO:27) used are as in FIG. 4. Final concentrations of components in the reaction mixtures (25 µl) at the start of PCR were: forward and reverse PCR primers—200 nM; TaqMan® probe—200 nM; target oligonucleotide—10,000 copies per reaction; dNTPs—200 µM each; JUMP START™ DNA polymerase (Sigma)—0.04 U/µl in 50 mM KCl, 2 mM $MgCl_2$, 20 mM Tris-HCl (pH 8.0). Background fluorescence was subtracted. The PCR cycling profile $(95°2') \to (95°10'' \to X°45'')_{55}$ was used with the annealing temperature "X" varying from 65 to 75° C.

FIG. 5A shows an exemplary set of experiments where unmodified primers and TaqMan® probe were employed with all natural dNTPs.

FIG. 5B shows results of exemplary experiments that are analogous to those of FIG. 5A, but wherein natural 2'-deoxyriboadenosine-5'-triphosphate (dATP) was completely substituted with 2'-deoxyribo-2,6-diaminopurine nucleoside-5'-triphosphate (d(2-amA)TP).

In FIG. 5C shows base-modified primers and probes used in the set of exemplary experiments, but wherein all nucleoside triphosphates (dNTPs) were natural.

FIG. 5D represents real-time TaqMan® assays where both system modifications of FIG. 5B and FIG. 5C were combined and employed at the same time; that is, base-modified primers and probe were used with complete d(2-amA)TP substitution of dATP.

A typical inventive detection PCR reaction to amplify modified DNAs comprises a target nucleic acid, a pair of oligonucleotide primers, a suitable DNA polymerase, and a mixture of deoxynucleoside 5'-triphosphates containing at least one base-modified duplex-stabilizing dNTP. Magnesium ion is preferably present in the reaction mixture because it enables the catalytic activity of many DNA polymerases. The reaction components are mixed using appropriate stock solution to provide, for example, the following concentrations in a 25 µl reaction mixtures: PCR primers—200 nM each; JumpStart DNA polymerase (Sigma)—0.04 U/µl in 50 mM KCl, 2 mM MgCl$_2$, 20 mM Tris-HCl (pH 8.0) and dNTPs—200 µM each; wherein one or more of the four natural dNTPs (e.g. dTTP, dCTP, dGTP or dATP) is completely or partially substituted with base-modified duplex-stabilizing dNTPs, some example of which are shown in FIG. 3. In addition to the components listed above, a detection PCR reaction mixture may include, but is not limited to the inclusion of detecting agents, specialty enzymes other than DNA polymerase, salts other than KCL and MgCl$_2$, co-factors and additives, for example, 1-methyl-2-pyrrolidinone, glycerol, poly(ethylene glycol), dimethyl sulfoxide or formamide and the like.

The target nucleic acid concentration in detection PCR is typically unknown, and it can be as low as 1 copy (molecule) per reaction. The target nucleic acids for use with the invention may be derived from any organism or other source, including but not limited to prokaryotes, eukaryotes, plants, animals, and viruses, as well as synthetic nucleic acids. The target nucleic acids may contain DNA, RNA, and/or variants thereof. Target nucleic acid can be single-stranded or double-stranded. When the nucleic acid of interest is a double-stranded DNA it is usually denatured before conducting the PCR temperature cycling by incubating the reaction mixture, for example, at 95° C. for 2 minutes. When an antibody-blocked DNA polymerase (e.g., JumpStart DNA polymerase (Sigma)) is used in the detection PCR, the initial heat incubation (95° C. for 2 minutes) is also activating the polymerase. Nucleic acids of interest can be isolated and purified from the sample sources before applying methods of the present invention. Preferably, the target nucleic acids are sufficiently free of proteins and any other substances interfering with amplification and detection reactions. Many methods are available for the isolation and purification of target nucleic acids including commercial kits and specialty instruments. For example, nucleic acids can be isolated using organic extraction with a phenol/chloroform organic reagent followed by ethanol precipitation (Ausubel et al., eds., Current Protocols in Molecular Biology Vol. 1, Chapter 2, Section I, John Wiley & Sons, New York (1993). Solid phase adsorption method (Walsh et al. (1991) *Biotechniques,* 10:506-513, Boom et al., U.S. Pat. No. 5,234,809) and salt-induced DNA precipitation (Miller et al (1988) Nucleic Acids Res., 16:1215) are yet other known approaches to purify nucleic acids. When the nucleic acid of interest is RNA, it can be converted to DNA/RNA heteroduplexes or to duplex cDNA prior to PCR by known methods; for example, described in Simpson D. et al (1988) *Biochem. Biophys. Res. Commun.,* 151: 487-492 and Belyaysky A. et al (1989) *Nucleic Acids Res.,* 17: 2919-2932 and the like. These methods employ reverse transcriptases which can extend an oligonucleotide primer hybridized to a RNA template, providing synthesis of complementary DNA (cDNA) in the presence of deoxynucleoside 5'-triphosphates (dNTPs); that is, "reverse transcription PCR" or "RT-PCR", and as described in a U.S. Pat. No. 5,168,038 of Tecott L. et al (1992), which patent is incorporated herein by reference. Certain amplification reactions like, for example NASBA, do not require synthesis of first cDNA copy and these techniques may be useful in detection of viral RNAs.

A typical PCR reaction consists of repetition of (i) a denaturation step which separates the strands of a double stranded nucleic acid, followed by (ii) an annealing step, which allows primers to anneal to positions flanking a target sequence; and then (iii) an extension step which extends the primers in a 5' to 3' direction thereby forming an DNA strand complementary to the target sequence. Each of the above steps may be conducted at a different temperature using an automated thermocycler. The PCR cycles can be repeated as often as desired resulting in an exponential accumulation of a target DNA fragment whose termini are defined by the 5' ends of the primers used. Particular temperatures, incubation times at each step and rates of change between steps depend on many factors well-known to those of ordinary skill in the art, and examples can be found in numerous published protocols, for example, McPherson M. J. et al. (1991 and 1995) and the like. Although PCR conditions can vary over a significant range, in a conventional PCR, a double-stranded target nucleic acid is usually denatured at a temperature>90° C., primers are annealed at a temperature in the range of 50-75° C., and extension is preferably performed at a temperature in the range of 72-78° C. Amplification specificity and time of the assay are important factors in detection PCR.

Two-Step PCR Embodiments:

As exemplified in FIGS. 5-11, and in particular FIGS. 5, 6, 9, 10 and 11, the present invention substantially improves hybridization properties of oligonucleotide components used in nucleic acid detection, and this in turn allows increasing the annealing temperature of PCR up to a temperature in the range of 72-75° C., which is optimal for performance of thermostable DNA polymerases like Taq. In preferred aspects, therefore, this leads to "merging" of the annealing and extension stages.

FIGS. 5A-5D (discussed in detail herein above) show exemplary results of fluorescence monitoring using the inventive methods in the context of TaqMan® detection assays during real-time PCR on a SmartCycler™ (Cepheid). Structures of the target oligonucleotide (SEQ ID NO:24), forward (SEQ ID NO:25) and reverse (SEQ ID NO:26 PCR primers and TaqMan® probe (SEQ ID NO:27) used are as in FIG. 4. FIG. 5A shows an exemplary set of experiments where unmodified primers and TaqMan® probe were employed with all natural dNTPs. FIG. 5B shows results of exemplary experiments that are analogous to those of FIG. 5A, but wherein natural 2'-deoxyriboadenosine-5'-triphosphate (dATP) was completely substituted with 2'-deoxyribo-2,6-diaminopurine nucleoside-5'-triphosphate (d(2-amA) TP). In FIG. 5C, base-modified primers and probes were used in the set of exemplary experiments, but wherein all nucleoside triphosphates (dNTPs) were natural. FIG. 5D represents real-time TaqMan® assays where both system modifications of FIG. 5B and FIG. 5C were combined and employed at the same time; that is, base-modified primers and probe were used with complete d(2-amA)TP substitution of dATP.

FIGS. 6A-6D show results of real-time TaqMan® assays when one of the natural dNTPs (used in FIG. 6A) was completely substituted with: 5-bromo-2'-deoxyribouridine-5'-triphosphate (d(5-BrU)TP, FIG. 6B); 5-propynyl-2'-deoxyribouridine-5'-triphosphate (d(5-PrU)TP, FIG. 6C) and 5-methyl-2'-deoxyribo-cytidine-5'-triphosphate (d(5-MeC) TP, FIG. 6D), respectively. FIG. 6A is identical to FIG. 5A, and it is shown here to facilitate direct comparison. PCR primers and TaqMan® probe were unmodified. Other PCR reaction compositions, component concentrations and temperature/time profiles were the same as described in the exemplary experiments shown in FIG. 5.

FIGS. 7A-7D show results of real-time fluorescence monitoring in exemplary TaqMan® assays at variable annealing temperatures (shown in ° C. for every curve). FIG. 7B shows fluorescent curves in the PCR reaction when two natural dNTPs (dATP and dTTP) were completely substituted with their respective base-modified analogs d(2-amA)TP and d(5-PrU)TP. Results in FIG. 7A are identical to those shown in FIG. 5A. PCR primers and TaqMan® probe were unmodified. Other PCR reaction compositions, component concentrations and temperature/time profiles were the same as described or the exemplary experiments of FIG. 5. The panel diagrams FIGS. 7C and 7D that are shown below FIGS. 7A and 7B, respectively, are the same results as shown in FIGS. 7A and 7B, but are plotted in logarithm scale. Fluorescent curve thresholds ("$C_t$") are shown by arrows, and were determined as cycle numbers at which the logarithm curves (i) point to, or (ii) intercept the X axis.

FIGS. 8A and 8B show real-time fluorescence curves. FIG. 8A shows the combined real-time fluorescence curves obtained for the same TaqMan® assay and reaction composition used in the FIG. 7B experiments, however the PCR profile was different; namely, $(95°2')\rightarrow(9X°YY"\rightarrow67° 45")_{55}$. In this case, the annealing temperature was constant (67° C.), and the denaturation conditions were varied in temperature (X=95-97° C.) and time (YY=10 or 15 seconds) as indicated for every curve. PCR primers and TaqMan® probe were unmodified. Other PCR reaction compositions and component concentrations were the same as described in FIG. 5. FIG. 8B (right) shows the same experiments as in FIG. 8A, but fluorescence is plotted in logarithm scale. Fluorescent curve thresholds ("$C_t$") are shown by arrows for the 95°10" and 97°15" curves.

FIG. 9 shows signal performance of the TaqMan® assays shown in exemplary FIGS. 5, 6 and 7, versus annealing temperature of PCR. Fluorescence of every individual reaction at PCR cycle 50 was plotted against the annealing temperature used in that reaction. In cases where two natural dNTPs were substituted with d(2-amA)TP and d(5-PrU)TP, the fluorescence data were taken at cycle 54, because of the 4-cycle "delay" in $C_t$ value observed in that assay (FIG. 7). Arrows point to the annealing temperatures at which approximately half of the assay signal (300 fluorescence units) has been reached.

FIGS. 10A-10C show results of fluorescence monitoring obtained for scorpion detection assays. Structures of the target oligonucleotide, forward and scorpion PCR primers used are as shown in FIG. 4. Final concentrations of components in the reaction mixtures (25 μl) at the start of PCR: forward and scorpion PCR primers—200 nM; target oligonucleotide ~10, 000 copies per reaction; dNTPs—200 μM each; JUMP START™ DNA polymerase (Sigma)—0.04 U/μl in 50 mM KCl, 2 mM $MgCl_2$, 20 mM Tris-HCl (pH 8.0). Background fluorescence was subtracted. PCR profile $(95°2')\rightarrow(95°10"\rightarrow X°45")_{55}$ was used with the annealing temperature X varying from 61 to 75° C.

FIG. 10A shows a set of exemplary experiments where a scorpion detection system was employed with all natural dNTPs. FIG. 10B shows experimental results that are analogous to FIG. 10A, but natural dATP was completely substituted with a d(2-amA)TP base-modified analog. FIG. 10C shows a set of experiments that are also analogous to FIG. 10A, but in this case, two of natural dNTPs, in particular, dATP and dTTP were completely substituted with respective base-modified analogs d(2-amA)TP and d(5-PrU)TP. To insure stability of the $C_t$ values, a slightly different PCR profile of $(95°2')\rightarrow(97°15"\rightarrow X°45")_{55}$ was used in the FIG. 10C set of experiments.

FIG. 11 shows signal performance of the scorpion assays from FIG. 10 versus annealing temperature of PCR. Fluorescence of every individual reaction at PCR cycle 50 was plotted against the annealing temperature used in that reaction. Arrows point to the annealing temperatures at which approximately half of the assay signal (150 fluorescence units) has been reached.

Therefore, in preferred embodiments, the detection PCR is performed in two stages, (i) strand denaturation and (ii) annealing/extension stage (combined). The number of the PCR cycles necessary to provide a detectable target nucleic acid concentration depends on the initial target nucleic acid load which is commonly unknown. As used herein, the PCR time/temperature profile may be recorded herein, for example, as $(95°2')\rightarrow(95°10"\rightarrow X°45")_{55}$. This means that prior to PCR regular cycles the reaction mixture was incubated at 95° fir 2 minutes (polymerase activation) and then 55 cycles were conducted wherein a DNA amplicon was denatured at 95° for 10 seconds followed by incubation at X° for 45 seconds (two-step PCR). X is a combined annealing/extension temperature that is usually above 50° C., preferably above 55° C., preferably above 60° C., more preferably above 65° C. and even more preferably above 70° C.

Additionally guidance for performing the PCR reactions can be found, for example, in Clementi M. et al (1993) *PCR Methods Appl.*, 2: 191-196; Clegg R. M. (1992) *Methods Enzymol.*, 211:353-388; Clementi M. et al (1993) *PCR Methods Appl.*, 2: 191-196; Lie Y. S. and Petropoulos C. J. (1998) *Curr. Opin. Biotech.*, 9: 43-48; Livak K. J. et al (1995) *PCR Methods and Applications*, 4: 357-362; McPherson M. J. et al, eds (1991) *PCR: A Practical Approach*. IRL Press, Oxford; McPherson M. J. et al, eds (1995) *PCR2: A Practical Approach*. IRL Press, Oxford, and many other manuscripts referred herein.

II. Detection of Nucleic Acids of Interest

DNA detection technologies. Modified DNA of the invention can be detected by any physical, chemical or biological means including but not limited to electrical force (e.g. electrophoresis), gravity (e.g. sedimentation), spectroscopy (e.g. radio spectroscopy, UV, mass spectroscopy, fluorescence, chemiluminescence, chemifluorescence, etc.), absorption, magnetism, chromatography (HPLC, reverse-phase, ion-exchange, volume exclusion, etc.), reactions with proteins (restrictases, endonucleases, polymerases, kinases and other enzymatic activities), binding affinity and the like. In certain embodiments, the modified DNA is labeled during or shortly after the amplification stage and the label is used in detecting the modified DNAs. The useful labels include but are not limited to isotopes, radiolabels such as $^{32}P$, binding moieties such as biotin, luminogenic and mass tags, phosphorescent or fluorescent moieties, fluorescent dyes alone or in combination with other dyes or moieties that can suppress or shift emission spectra by FRET effect. In other embodiments, modified DNAs of the invention may be detected using a detecting agent during the amplification reaction (real time) or after. The preferred detecting agents are intercalating dyes and fluorescent agents, e.g. ethidium bromide. For example, amplification products in PCR can be detected using intercalating dyes as described by Wittwer C. T. et al in U.S. Pat. Nos. 6,174,670 and 6,569,627 and in Higuchi R. et al (1992) *Biotechnology*, 10:413-417; Higuchi R. et al (1993) *Biotechnology*, 11:1026-1030. The preferred fluorescent agents are those molecules that change its fluorescence properties upon the interaction with nucleic acids providing detectable signal. SYBR Green I and II from Invitrogen are examples of the preferred fluorescent agents as described in Schneeberger C. et al (1995) *PCR Methods Appl.*, 4: 234-238 and Mackay J., Landt O. (2007) *Methods Mol. Biol.*, 353: 237-262 which are incorporated herein by reference.

Oligonucleotide probes. In one embodiment, a modified DNA of the invention is detected using an oligonucleotide probe. The oligonucleotide probe of the invention interacts with the modified DNA in a sequence-specific fashion forming a complex (e.g. complementary duplex) and this complex is more stable by virtue of the modified DNA of the invention having enhanced hybridization properties compared to those conventional approaches wherein the DNA is not modified with duplex-stabilizing base analogs. In general, stability of the complex determines the sensitivity of the detection. Stabilization of the complex between oligonucleotide probe and modified DNA may benefit the detection assay in a variety of ways as discussed herein above.

In another embodiment, the oligonucleotide probe incorporates a label wherein this label is used in detecting of modified DNA of the invention. In a preferred embodiment, this label is a fluorescent label and it is used in detecting the modified DNA by a fluorescence polarization technique. In even more preferred embodiment, the oligonucleotide probe is a FRET probe. Application of FRET probes in detection of modified DNAs provides critical advantages in performing the detection assay in real time and measuring amount of target nucleic acid in the sample. When the amplification reaction is PCR, this type of the assay is termed "quantitative PCR." The FRET probe commonly contains two chromophores. The 'acceptor' chromophore may be a non-fluorescent dye chosen to quench fluorescence of the 'reporting' fluorophore (Eftink M. R. (1991) In Lakowicz J. R. (ed.), *Topics in Fluorescence Spectroscopy*. Plenum Press, New York, V. 2:53-126). Formation of sequence-specific hybrids between target nucleic acid and probes leads to a change in fluorescent properties of the probe providing detection of the nucleic acid target. The real time FRET based assays are well suited, in particular, for clinical diagnostics. An important factor to note here is that, unlike the case of intercalating dyes and fluorescent agents (e.g. ethidium bromide, SYBR Green) that are discussed above, the detection is sequence-specific, virtually eliminating fault positive results. Many detection designs exploring the FRET effect have been reported to date.

A first FRET strategy is a hybridization-triggered FRET probe approach, which is based on distance change between the donor and acceptor dyes as result of a sequence-specific complex formation between a target nucleic acid and a fluorescent oligonucleotide probe. For example, the Adjacent Hybridization Probe method utilizes two oligonucleotide probes hybridizing to adjacent target DNA sequences as described in e.g. Eftink M. R. (1991) In Lakowicz J. R. (ed.), *Topics in Fluorescence Spectroscopy*. Plenum Press, New York, V. 2:53-126; Heller M. J. and Morrison L. E. (1985) In Kingsbury, D. T. and Falkow, S. (eds.), *Rapid Detection and Identification of Infectious Agents*. Academic Press, New York, 245-256; Cardullo R. A. et al (1988) *Proc. Natl. Acad. Sci. USA*, 85:8790-8794. Each of the probes is labeled by one of FRET-pair dyes at appropriate probe ends so that when both probes are hybridized to a target DNA the donor and acceptor fluorophores are brought in sufficient spatial proximity providing for detectable FRET.

An alternative approach is Self-Quenching Fluorescence probes as described in Livak K. J. et al, U.S. Pat. No. 5,723,591. These probes include fluorescent reporter and quencher moieties conjugated to opposite ends of the same probe. Due to random oligonucleotide coiling, the quencher moiety is sufficiently close to the reporter dye to quench its fluorescence. Once the probe is hybridized to a complementary polynucleotide target, the quencher and reporter moieties are separated, thus enabling the reporter dye to fluoresce. The Self-Quenching Fluorescence probe approach has limited application due to a profoundly inefficient FRET effect in the unhybridized probe, which in turn leads to an elevated fluorescence background. The background problem can be resolved by synthesizing the oligonucleotide with a flexible PNA backbone, e.g. Ortiz E. et al (1998) *Mol. Cell. Probes*, 12: 219-226.

Alternatively, efficient FRET is achieved using Molecular Beacons, hairpin-shaped oligonucleotide probes in which the FRET dyes are brought in close proximity by intramolecular stem formation, e.g. Tyagi S. and Kramer F. R. (1996) *Nat. Biotechnol.*, 14: 303-308; Bonnet G. et al (1999) *Proc. Natl. Acad. Sci. USA*, 96: 6171-6176; Tyagi S. et al (2000) *Nat. Biotechnol.*, 18: 1191-1196; Marras S. A. E. et al (2002) *Nucleic Acids Res.*, 30: e122. Molecular Beacon methods are preferred technologies in practicing present invention due to their remarkably low fluorescence background. These probes are well adapted for use in real-time PCR as described in, e.g. Piatek A. S. et al (1998) *Nat. Biotechnol.*, 16:359-363; Lewin S. R. et al (1999) *J. Virol.*, 73: 6099-6103. Molecular Beacons have improved polymorphism discriminating capabilities.

Covalent linking of a molecular beacon probe to one of the PCR primers is a unique property of Scorpion primers, e.g. Whitcombe D. et al (1999) *Nature Biotech.*, 17: 804-807; Thelwell N. et al (2000) *Nucleic Acids Res.*, 28: 3752-3761. In 'Scorpions,' the 5'-end of a PCR primer is conjugated to the 3'-end of a molecular beacon through a long, flexible linker. The linker is not a template for DNA polymerase, thus precluding extension over the beacon sequence. The genomic part of the molecular beacon is designed to bind to a targeted extension product of the primer to which the probe is covalently linked. Unlike Molecular Beacons, the DNA detection stage in Scorpions becomes an intra-molecular reaction. This helps to overcome yet another problem of the Beacon technology associated with the slow kinetics of hybridization.

Eclipse probes are yet another example of hybridization-based FRET probes that have low fluorescence background (Afonina I. A. et al (2002) *BioTechniques*, 32: 940-949). The Eclipse probe design includes a minor groove binding (MGB) moiety at the 5'-end in addition to two FRET dyes, one of which is a non-fluorescent or dark quencher. Due to the strong, DNA-duplex stabilizing effect of the MGB-moiety as discussed in Kutyavin I. V. et al (1997) *Nucleic Acids Res.*, 25: 3718-3723, the probes can be designed to be as short as 12-20-mers and yet maintaining the hybridization properties required for real-time PCR detection. Placing the MGB-tail at the 5'-end of the probes completely blocks 5'-nuclease cleavage and the fluorescent signal is generated solely due to the hybridization-triggered dye separation. The fluorescence background is low and Eclipse probes readily discriminate SNPs.

The mechanism of FRET disruption by distancing of FRET dyes possesses certain limits. It is difficult, for example, to completely abolish the FRET effect, and the probes have to be at least 20-24-mers. In short 8-12 bp probe-target duplexes, "residual" quenching can reach as much as 20-50% (Cardullo R. A. et al (1988) *Proc. Natl. Acad. Sci. USA*, 85: 8790-8794). Furthermore, the reporter dye can be partially quenched by neighboring bases, in particular, by guanines regardless of little spectral overlap. This effect is well known and has been used in a DNA detection technology known by the name of Self-Quenched Fluorogenic primers or also LUX primers (abbreviation of Light Upon eXtension), e.g. Nazarenko I. et al (2002) *Nucleic Acids Res.*, 30: e37; Nazarenko I. et al (2002) *Nucleic Acids Res.*, 30: 2089-2195. The technology performs best with "green" dyes like fluorescein (FAM). However, LUX primers are not sequence-specific. Any product of a LUX primer extension, including primer-dimers, will generate a fluorescent signal.

Cleavable FRET probes. The best strategy to abolish FRET is based on cleavage of the oligonucleotide probes upon their binding to target nucleic acids. TaqMan™ technology was developed as a real-time nucleic acid detection method and utilizes the 5'-3' exonuclease activity of *Thermus aquaticus* (Taq) polymerase, e.g. Lie Y. S. and Petropoulos C. J. (1998) *Curr. Opin. Biotech.*, 9:43-48. A dual-labeled FRET probe is designed to anneal to a target sequence located between two PCR primer binding sites. During strand elongation, Taq polymerase cleaves the probe that is hybridized down stream from a primer site releasing the reporter dye from the quencher thus permanently and irreversibly disrupting FRET, e.g. Livak K. J. et al (1995) *PCR Methods and Applications*, 4: 357-362. TaqMan™ probe based methods are some of the most preferred technologies for practicing aspects of the present invention. TaqMan™ probe cleavage is irreversible and signal generated at a given PCR cycle is a sum of signals generated at that particular cycle plus all previous ones. However, elevated fluorescence background of the "classical" TaqMan™ probes overshadows this advantage. Conjugation with an MGB-moiety at the 3'-end leads to significant improvement of this parameter (Kutyavin I. V. et al (2000) *Nucleic Acids Res.*, 28:655-661). Relatively short 12-18-mer MGB-TaqMan™ probes have improved SNP discriminating properties. However, TaqMan™ technology is still tightly bound to PCR performance whereas Cycling Probe Technologies (CPT) are relatively independent.

Cycling Probe Technologies (CPT). Cycling Probe Technologies (CPT) are also preferred detection systems for practicing methods of the invention. These reactions are based on continuous cleavage of oligonucleotide probes which bind to a target nucleic acid in a sequence-specific fashion. An appropriate endonuclease recognizes the complex and cleaves the probe while leaving the target strand intact recycling it for the next round of cleavage. If the hybridized probe is cleaved internally, the cleavage products form weaker hybrids than the original probe and these probe fragments dissociate from the target strand leaving it available for additional rounds of the cleavage reaction. Target recycling means that more than one probe can be cleaved per target molecule. Unlike all other technologies referred above, including TaqMan™, in CPT reactions the signal is a function of two main variables, target concentration and time. When the target concentration is fixed, the signal grows linearly in time. Reflecting the reaction progress, cleavage slows down and eventually stops when essentially all CPT probes get cleaved. Several system designs have been reported. The first approach is based on use of chimeric DNA-RNA probes that are cleaved by RNAse H upon the binding to target DNA, as described in Fong W. et al (2000) *J. Clin. Microbiol.*, 38: 2525-2529; Modruzan Z. et al (2000) *Diagn. Microbiol. Infect. Dis.*, 37: 45-50. These DNA probes are designed to have at least 4-5 ribonucleotides in the middle of the oligonucleotide chain. RNAse H cleaves only the RNA portion of the hybridized probe and the target polynucleotide is recycled to hybridize to another uncleaved probe molecule. Under appropriate conditions, this leads to a cycling of the probe cleavage reaction. Recent discovery and isolation of thermo-stable analogs of RNAse H have allowed combining this DNA detection technology with PCR as demonstrated in e.g. Harvey J. J. et al (2004) *Anal. Biochem.*, 333: 246-255. The respective FRET probes may be obtained from Takara Bio.

The second CPT approach is based on the substrate specificity of Endonuclease IV from *E. coli*, an AP endonuclease that initiates repair of abasic sites and other related lesions in DNA. A FRET probe and enhancer can collectively form a substrate for the AP endonuclease that simulates a partially degraded abasic site. The enzyme recognizes this artificial substrate and "clips" the 3'-tail of the probe thereby releasing the reporter dye and disrupting FRET. This reaction can be performed in a cycling mode where a high yield of cleaved probe is achieved at nanomolar or even sub-nanomolar target DNA concentrations as described in Kutyavin I. V. et al (2004) US Patent Application #20040101893.

Third, and perhaps, the most advanced cycling probe technology on the market is the INVADER™ detection assay. It utilizes the flap or 5'-endonuclease activity of certain polymerases to cleave two partially overlapping oligonucleotides upon their binding to target DNA. The INVADER™ assay typically consists of two consecutive cycling cleavage reactions. The enzyme used to provide the cleavage reaction is CLEAVASE, a DNA polymerase with substantially reduced or completely eliminated synthetic capabilities, e.g. Dahlberg J. E. et al (1997) U.S. Pat. No. 5,691,142; Dahlberg J. E. et al (1998) U.S. Pat. No. 5,837,450; Brow M. A. D. et al (1998) U.S. Pat. No. 5,846,717; Prudent J. R. et al (1999) U.S. Pat. No. 5,985,557; Hall J. G. et al (1999) U.S. Pat. No. 5,994,069; Brow M. A. D. et al (1999) U.S. Pat. No. 6,001,567; Prudent J. R. et al (2000) U.S. Pat. No. 6,090,543; Prudent J. R. et al (2002) U.S. Pat. No. 6,348,314; Prudent J. R. et al (2005) U.S. Pat. No. 6,875,572; Aizenstein B. D. et al (2005) U.S. Pat. No. 6,913,881; Schweitzer B. and Kingsmore S. (2001) *Curr. Opin. Biotech.*, 12: 21-27. The detection system is a very efficient signal amplification assay which may not require any prior target DNA amplification. However, prior amplification of nucleic acids is a preferred approach in applying the INVADER assay. The primary concern is background fluorescence that increases linearly with time. It is generated by non-specific cleavage of the cassette probe. Furthermore the assay requires substantial target DNA load, e.g. Schweitzer B. and Kingsmore S. (2001) *Curr. Opin. Biotech.*, 12: 21-27, when the amplification is not applied. Combinations of CPT with nucleic acid amplification techniques provide critical advantages as described for the oligonucleotide probes with secondary structures in Sorge J. A. (2001) U.S. Pat. No. 6,589,743.

The cited and above-described nucleic acid detection technologies represent an exemplary fraction of innovations and methods in this field of art. There are many other techniques that are based on use of oligonucleotide probes and, in particular, FRET probes. All of the technologies that are based on hybridization of an oligonucleotide probe with a target nucleic acid would benefit from use the present invention. Detailed guidance in performing a particular detection reaction including the rules for oligonucleotide primer and probe designs, preferred composition of the reaction mixtures, reaction conditions, characteristics of the assays and its applicability and limitations, and other important information to carry out the detection reactions can be found in cited above manuscripts and patents which are incorporated herein by reference.

III. Detection Assay Components

DNA polymerases. DNA polymerases are key components in practicing nucleic acid assays of the present invention.

DNA polymerases useful according to the invention include both native polymerases as well as polymerase mutants, which lack 5' to 3' and/or 3' to 5' exonuclease activity. Nucleic acid polymerases can possess different degrees of thermostability. The choice of DNA polymerase is determined by many factors that usually relate to the choice of the amplification and detection reactions applied in the invention. In certain embodiments, a DNA polymerase preferably exhibits strand displacement activity at the temperature at which it can extend an oligonucleotide primer. In many cases of isothermal amplification wherein DNA amplification is based on displacement of one of the DNA strand, for example, in SDA and Rolling Circle amplifications, a DNA polymerase preferably lacks 5' to 3' exonuclease activity. DNA polymerases of the invention can be isolated from various natural sources including bacteriophage, archaeal, eubacterial and eukaryotic enzymes.

Commercially-available enzymes that lack both 5' to 3' and 3' to 5' exonuclease activities include Sequenase (exo-T7; USB), Pfu exo-(Stratagene), exo-Vent (New England BioLabs), exo-DeepVent (New England BioLabs), exo-Klenow fragment (Stratagene), Bst (Bio-Rad), Isotherm (Epicentre), Stoffel fragment (Perkin-Elmer), ThermoSequenase (USB), and TaqFS (Hoffman-LaRoche). Examples of thermostable DNA polymerases which are useful for detection PCR assays include but not limited to Pfu, Taq, Vent, Deep Vent and UITma DNA polymerases and other polymerase from Thermus species or from *Thermotoga maritima*. The thermostable polymerases for the detection PCR preferably mountain activity at temperature>90° C. and more preferably at >100° C. Certain detection reactions, for example, TaqMan assays, require use of DNA polymerase that express 5' to 3' exonuclease activity. JumpStart DNA polymerase from Sigma was used in Examples provided herein.

Base-modified duplex-stabilizing deoxynucleoside 5'-triphosphates (dNTPs). Modified DNAs with enhanced hybridization properties of the present invention are amplified in a reaction of template-dependant oligonucleotide primer extension in presence of a DNA polymerase in a mixture of dNTPs which comprises at least one and preferably more than one base-modified duplex-stabilizing deoxynucleoside 5'-triphosphate. Examples of the dNTP analogs useful in practicing present invention include but not limited to those shown in FIG. 3. The amplification reaction of the invention typically includes all four dNTPs (dTTP, dCTP, dATP and dGTP) wherein one or more of the natural dNTPs is partially or completely substituted with a respective base-modified duplex-stabilizing dNTP. The base-modified duplex-stabilizing deoxynucleosides of the present invention contain 2-deoxy-D-ribose wherein nucleotide base is modified. These nucleoside analogs can be synthesized applying well known techniques of organic chemistry which are exemplified in e.g. Townsend L. B., ed. (1988) Chemistry of Nucleosides and Nucleotides, Plenum Press, NY. Respective 5'-triphosphates can be obtained using protocols described in e.g. Vaghefi M., ed. (2005) Nucleoside Triphosphates and their Analogs: Chemistry, Biochemistry, and Biological Applications, Taylor & Francis. The base-modified duplex-stabilizing deoxynucleosides of the present invention, including many of those shown in FIG. 3, can be obtained from commercial sources, for example, Trilink (California, USA).

As required by certain amplification schemes, the reaction mixture of the invention may also incorporate dNTP analogs other than the base-modified and duplex-stabilizing ones. For example, SDA amplification described in Walker G. T. et al (1993) U.S. Pat. No. 5,270,184 requires use of a α-thio dNTP analog to promote nicking of one strand of double-stranded DNAs. Deoxyuridine 5'-triphosphate (dUTP) is yet another example. Although this base modification is known to destabilize DNA duplexes, use of such modified DNAs is still within the scope of the present invention. The main purpose of the dUTP application is in preventing contamination carryovers from sample to sample as described in Gelfand D. H. et al (1995) U.S. Pat. No. 5,418,149 which is incorporated herein by reference.

Depending on the choice of the DNA amplification reaction, the reaction components of the invention may vary. In addition to the main components, the reaction mixtures of the invention may include, but not be limited to, detecting agents, specialty enzymes (e.g. reverse transcriptases, nucleases, FEN endonucleases, restriction endonucleases, RNAses, including RNAse H, RNA polymerases, helicases, etc.), buffering agents to maintain pH at a selected level during a reaction, salts, co-factors and additives, for example, 1-methyl-2-pyrrolidinone, glycerol, poly(ethylene glycol), dimethyl sulfoxide (DMSO) or formamide and the like.

Oligonucleotide primers and probes. Oligonucleotide primers initiate synthesis and amplification of modified DNAs in all amplification reactions of the present invention. The oligonucleotide primers may occur naturally, as in a purified restriction digest or may be produced synthetically. Oligonucleotide primers of the invention must be sufficiently complementary to hybridize with a template strand for primer elongation to occur in presence of a DNA polymerase. The sequence of the oligonucleotide primers need not reflect the exact sequence of the target nucleic acids they are design to hybridize. For example, a non-complementary nucleotide fragment may be attached to the 5' end of the primer, with the remainder of the primer sequence being substantially complementary to the strand. Non-complementary bases or longer sequences can be interspersed within the primer, provided that the primer sequence has sufficient complementarity with the sequence of the template to hybridize and thereby form a template-primer complex for synthesis of the extension product of the oligonucleotide primer. The primer design is guided by a particular amplification reaction. For example, the primers designed for SDA amplification incorporates a sequence of a restriction endonuclease which supports the amplification reaction, e.g. Walker G. T. et al, U.S. Pat. No. 5,270,184; Dattagupta N. et al, U.S. Pat. No. 6,214,587; Walker G. T. et al (1996) *Nucleic Acids Res.*, 24:384-353; Walker G. T. et al (1992) *Proc. Natl. Acad. Sci. USA*, 89:392-396; Spargo C. A. et al (1996) *Molecular and Cellular Probes*, 10:247-256.

Synthetic oligonucleotide primers useful for the invention may contain structural modifications such as atoms, moieties, residues, polymers, linkers which are usually of a synthetic nature and which are not commonly present in natural nucleic acids. The oligonucleotide primers may incorporate a detectable label, for example, isotopes, radiolabels such as $^{32}P$, binding moieties such as biotin, haptens such as dioxygenin, luminogenic, mass tags, phosphorescent or fluorescent moieties, fluorescent dyes and the like. Since primers are usually incorporated during the DNA amplification, the label may be used to detect the modified DNAs in the present invention. Oligonucleotide primers also may incorporate nucleoside or nucleotide analogs which rarely present in natural nucleic acid including but not limited to inosine (hypoxanthine), 5-bromouracil, 5-methylcytosine, 5-iodouracil, 2-aminoadenosine, 6-methyladenosine, preudouridine and the like. In preferred embodiments, oligonucleotide primers incorporate structural modifications which provide duplex-stabilizing effect. However, in all aspects of the invention, 3' end of the primers must not be blocked to initiate the DNA synthesis.

The examples of preferred structural modifications that may be used in design of the oligonucleotide primers include but not limited to minor groove binders (MGB) (Afonina I. et al (1997) *Nucleic Acids Res.*, 25: 2657-2660) which are usually coupled to the 5' end and certain nucleotide analogs, although the number of these modifications may be limited. Examples of the nucleotide analogs include "universal" bases (Burgner D. et al (2004) *Nucleosides Nucleotides Nucleic Acids*, 23: 755-765) and "locked nucleic acids" ("LNA") (Latorra D. et al (2003) *Mol. Cell. Probes*, 17: 253-259; Latorra D. et al (2003) *Hum. Mutat.*, 22:79-85; Di Giusto D. A. and King G. C. (2004) *Nucleic Acids Res.*, 32: e32). A number of the base-modified nucleotide analogs are well tolerated by DNA polymerases and these analogs can be used in primer design. Examples of such base-modified nucleotide analogs include but not limited to 5-methyl cytosine and 2,6-diaminopurine (Lebedev Y. et al (1996) *Genet. Anal.*, 13, 15-21).

Oligonucleotide primers according to the invention can be labeled and they can be used to amplify a labeled modified DNA. The label is used in nucleic acid detection stage. A preferred label is a fluorescent label. In one aspect, an oligonucleotide primer may be coupled with an oligonucleotide probe, e.g. Scorpion primer (Whitcombe D. et al (1999) *Nature Biotech.*, 17:804-807; Thelwell N. et al (2000) *Nucleic Acids Res.*, 28:3752-3761).

Probes. Oligonucleotide probes according to the invention are oligomers or polymers capable of forming duplex structures or other complexes with products of amplification of the invention, the modified DNAs, due to complementarity of at least one sequence in the probes with respective sequences in modified DNAs. Oligonucleotide probes of the present invention can be modified or contain structural modifications. Certain modifications are commonly present in the oligonucleotide probes and they usually relate to labels used in detecting of modified DNAs of the invention. Fluorescently labeled oligonucleotide and, in particular, FRET probes are preferred detecting components of the invention. When oligonucleotide probes and primers hybridizes to a modified DNA of the invention, they form stabilized complementary complexes because of the modified DNAs of the invention express enhanced hybridization properties compare to those conventional approaches wherein the DNA is not modified with duplex-stabilizing base analogs. Unlike the oligonucleotide primers, oligonucleotide probes have few limits for use of the structural modifications. This is especially true for the hybridization-triggered FRET probe technologies. For example, as used herein, the oligonucleotide probes can be completely made of unnatural PNA monomers, e.g. Ortiz E. et al (1998) *Mol. Cell. Probes*, 12:219-226. Use of the other base-modified or sugar-modified nucleotide analogs in probe designs like LNA is also broadly applicable (Johnson M. P. et al (2004) *Nucleic Acids Res.*, 32:e55; Simeonov A. and Nikiforov T. T. (2002) *Nucleic Acids Res.*, 30:e91). Oligonucleotide probes can carry an MGB moiety conjugated to either end. For example, 5'-MGB-conjugated FRET probes are not cleaved in detection PCR and these probes provide signal due to a hybridization-triggered mechanism of action as described in Vermeulen N. et al (2002) *J. Clin. Ligand Assay*, 25: 268-275. 3'-MGB-conjugated FRET probes are not blocked from 5'-nuclease degradation and these probes generate fluorescent signal due to the cleavage by Taq polymerase as exemplified in Kutyavin I. V. et al (2000) *Nucleic Acids Res.*, 28:655-661. In those cases, when the probe cleavage approach is used, the limits on use of the structural modifications may apply, in particular, within the sequence of the cleavage sites.

The oligonucleotide primers and probes may be synthesized using techniques that are well known in the Art. Although the primers can be prepared by, for example, cloning and restriction digest analysis of appropriate sequences, direct chemical synthesis is a preferred approach. Oligonucleotides can be prepared by a suitable chemical synthesis method, including, for example, the phosphodiester method disclosed in Brown E. L. et al (1979) *Methods Enzymol.*, 68: 109-151, the phosphotriester method described in Narang S. A. et al (1979) *Methods Enzymol.*, 68: 90-98. The preferred approach is the diethylphosphoramidate method disclosed in Beaucage S. L., Caruthers M. H. (1981) *Tetrahedron Lett.*, 22: 1859-1862, in combination with the solid support method disclosed in Caruthers M. H., Matteucci M. D. (1984) U.S. Pat. No. 4,458,066 and performed using one of commercial automated oligonucleotide synthesizer.

When oligonucleotide primers and probes of the invention need to be labeled with a fluorescent dye, a wide range of fluorophores may be applied in probe and primer designs and synthesis. Available fluorophores include but not limited to coumarin, fluorescein (FAM, usually 6-fluorescein or 6-FAM), tetrachlorofluorescein (TET), hexachlorofluorescein (HEX), rhodamine, tetramethylrhodamine, BODIPY, Cy3, Cy5, Cy7, Texas red and ROX. Fluorophores may be chosen to absorb and emit in the visible spectrum or outside the visible spectrum, such as in the ultraviolet or infrared ranges. FRET probes of the invention commonly incorporate a pair of fluorophores, one of which may be a none-fluorescent chromophore (commonly referred as a "dark quencher"). Suitable dark quenchers described in the art include particularly Dabcyl and its derivatives like Methyl Red. Commercial none-fluorescent quenchers, e.g. Eclipse (Glen Research) and BHQ1, BHQ2, BHQ3 (Biosearch Technologies), may be also used for synthesis of FRET probes of the invention. Preferred quenchers are either dark quenchers or fluorophores that do not fluoresce in the chosen detection range of an assay.

The donor and acceptor fluorophores for manufacturing of the labeled oligonucleotide components of the invention may be selected from suitable fluorescent groups, e.g. 6-FAM (6-carboxyfluorescein); 6-hexachloro-fluorescein ([4,7,2',4', 5',7'-hexachloro-(3',6'-dipivaloylfluoresceinyl)-5-carboxylic acid]); 6-tetrachloro-fluorescein ([4,7,2',7'-tetrachloro-(3',6'-dipivaloylfluoresceinyl)-6-carboxylic acid]); 6-TAMRA (6-carboxytetramethylrhodamine; Dabcyl (4-((4-(dimethylamino)phenyl) azo)benzoic acid); Cy5 (Indodicarbocyanine-5); Cy3 (Indo-dicarbocyanine-3); and the like.

Oligonucleotide primers and probes for practicing the invention are designed according to rules and specifications of a particular amplification or detection technology known in the art, including those techniques discussed and cited above. There are certain common requirements to the oligonucleotide components, for example, the hybridization properties of the oligonucleotide need to address the temperature of a particular reaction, usually referred as melting temperature (Tm). Tm defines a temperature at which a complementary complex of an oligonucleotide component with target nucleic acid becomes half dissociated into single strands. A simple estimate of the Tm value may be calculated using the equation Tm=81.5+0.41(% G+C), when a nucleic acid is in aqueous solution at 1 M NaCl. More accurate calculations can be made using the base pair thermodynamics of a "nearest-neighbors" approach (Breslauer K. J. et al (1986) *Proc. Natl. Acad. Sci. USA*, 83: 3746-3750; SantaLucia J. Jr. (1998) *Proc. Natl. Acad. Sci. USA*, 95: 1460-1465). Commercial programs, including Oligo™, Primer Design and programs available on the internet, including Primer3 and Oligo Calculator can be also used to calculate a Tm of a nucleic acid sequence useful according to the invention. Commercial programs, e.g. Visual OMP (DNA software), Beacon designer 7.00 (Premier Biosoft International), may be helpful in design of real time assays with SYBR Green, TaqMan and molecular Beacons detection system for PCR-based and NASBA amplification reactions. In general, Tm values of the oligonucleotide probes are 5-7° C. higher than the Tm of the corresponding amplification primers.

The nearest-neighbors thermodynamic parameters have been determined only for natural bases (see Breslauer K. J. et al (1986) *Proc. Natl. Acad. Sci. USA*, 83: 3746-3750). Analogous values for modified nucleotide analogs are not available making impossible accurate prediction of Tm values for the base modified oligonucleotide primers and probe of the invention. However, estimates may be made providing that substitution of one deoxyadenosine by d(2-amA) (2,6-diaminopurine) and one thymidine by 5-propynyl uridine increase Tm value of a randomly taken 20-mer oligonucleotide by 0.8-1° C. The same estimates can be used when these modified nucleotide are incorporated into the modified DNA strand, although this may be even less accurate due to increased propensity of long polynucleotides in forming secondary structures ("coiling" effect). Tm values for MGB-conjugated oligonucleotide primers and probes may be assessed according to guidance of Kutyavin I. V. et al (1997) *Nucleic Acids Res.*, 25 3718-3723. Melting temperatures of 3'-MGB TaqMan probes can be predicted using commercial software provided by the manufacturer (ABI, California, USA).

IV. Performing the Detection Assay of the Invention

Preparation of Nucleic Acids for Amplification and Detection. Particular Aspects of the invention relate to methods for the detection of target nucleic acids in test sample. The sample can be cell, tissue, fluid, plasma, serum, urine, tears, stool, saliva, fragments of different organs, tissue, blood cells and the like, containing materials, usually of biological nature, other than nucleic acids to be detected. Before conducting the amplification and detection stages, nucleic acids of interest commonly need to be purified and isolated from the samples. Preferably, the target nucleic acids are sufficiently free of proteins and any other substances interfering with amplification and detection reactions. Many methods are available for the isolation and purification of target nucleic acids including commercial kits and specialty instruments. For example, nucleic acids can be isolated using organic extraction with a phenol/chloroform organic reagent followed by ethanol precipitation, solid phase adsorption method and salt-induced DNA precipitation. Guidance in performing the nucleic acid isolation techniques may be found in, e.g. Ausubel et al., eds., (1993) Current Protocols in Molecular Biology Vol. 1, Chapter 2, Section I, John Wiley & Sons, New York; Walsh et al. (1991) *Biotechniques*, 10: 506-513; Boom et al., U.S. Pat. No. 5,234,809; Miller et al (1988) Nucleic Acids Res., 16: 1215. Amounts of nucleic acids of interest isolated from different sources are commonly limited to enable direct detection. Therefore, the target nucleic acids need to be amplified using a suitable amplification procedure.

Amplification and detection of modified DNAs. The purified nucleic acids of interest may be amplified and detected by a combination of the amplification and detection techniques including those cited and discussed herein with a provision that, in addition to all reagents required for any specific amplification of choice, the amplification reaction comprises at least one base-modified duplex-stabilizing dNTP to produce multiple copies of modified DNAs of the present invention. In one embodiment, the detection of target nucleic acid is performed after the amplification. In certain aspects, these two stages may be completely separated in "time and space" so as the components of the detection reaction are not present in the reaction mixture during the amplification. This includes the case when the detection reaction is performed in a separate reaction vessel or tube. In such instances, modified DNA from the amplification reaction (whole amount or a fraction) may be transferred to a reaction vessel wherein the detection reaction will be performed. Alternatively, the detection components may be added to the reaction vessel after the amplification is completed. The modified DNA may be completely or partially purified from the amplification components before it is added to the detection reaction, for example, using alcohol precipitation or commercial kits. In another embodiment, all or some of the components of the detection reaction are present during the amplification reaction but the detection does not proceed, for example, because of the reaction temperature which does not support the detection stage. When the nucleic acid amplification is essentially completed, the detection reaction is triggered by the reaction temperature change. The reaction separation strategy allows to combine in one nucleic acid detection assay majority of the amplification and detection reactions including but not limited to those discussed and referenced herein. Exceptions may be the detection reactions like TaqMan™ which are designed for real time performance. However, this strategy complicates the quantitative nucleic acid measurements. The preferred nucleic acid detection assays to practice the invention are real time detection assays.

Those of ordinary skill in the art will appreciate that there are certain considerations in compiling the amplification and detection reactions in a real time assay. Generally, the amplification systems that are based on strand displacement like SDA and Rolling Circle may be less compatible with the detection reactions that require use of an exonuclease activity like TaqMan and Invader technologies. A real time assay may be conducted using a detecting agent like ethidium bromide or SYBR Green I. However, this approach essentially eliminates possibility of detecting multiple nucleic acids of interest (multiplex assay) and the detection reaction is not sequence specific providing no discrimination between products of interest and misamplification, e.g. primer-dimer. Examples where the sequence specific detection components (commonly FRET probes) do not interfere with the amplification reaction have been reported. For example, a fluorescent probe called a Molecular Zipper was effectively combined with Rolling Circle amplification (Yi J. et al (2006) *Nucleic Acids Res.*, 34:e81) and several detection technologies were combined with NASBA amplification (Niesters H. G. (2001) *Methods*, 25:419-429). PCR is a very compatible reaction and many real time assays have been developed to date based on this amplification system as this is reflected in numerous patents and manuscripts cited herein. The examples provided herein also illustrate real time detection PCR employing FRET probe detection reactions, TaqMan and Scorpion technologies.

In preferred embodiments, more than one target nucleic acid are amplified and detected in the same reaction mixture (multiplex assay). Preferably, the detection of multiple nucleic acids is done in real time. This may be accomplished when the detection components such as oligonucleotide probes are labeled with different moieties which can be independently detected. When FRET probes are used, this is achieved by a selection of the reporting fluorophores which emit light in different parts of the spectrum.

V. Examples

Those of ordinary skill in the art will be surprised by the inventive use of the base-modified duplex-stabilizing dNTPs in amplifying and detecting the modified DNAs according to the invention. In order to satisfy the requirements of nucleic acids detection assays, in particular, the challenging time and temperature restrictions of detection PCR, the substrate properties of the modified dNTPs have to be a close match with those of the natural dNTPs. It is well established in the art that structural changes in dNTPs are usually followed by negative changes in their substrate properties regarding the interaction with DNA polymerase (see "BACKGROUND" herein). For example, modified dNTPs can be incorporated less efficiently and this can slow down the amplification to a degree that is unacceptable for nucleic acid detection assays. Moreover DNA polymerase, particularly in PCR, faces modified bases in two mutually different occasions (i) when it incorporates modified dNTPs into growing DNA strand and (ii) when it incorporates their Watson-Creek counter parts using base-modified template produced in previous cycles. According to the study made by Sawai H. Et al (2002) *Bioconjug. Chem.*, 13: 309-316, response of a DNA polymerase on base modifications in these two occasions can be different. Preferential stabilization of the secondary structure elements within the modified DNA is yet another reason for the concern. Virtually any, randomly taken polynucleotide, including the 96-mer target oligodeoxyribonucleotide which was used as a target nucleic acid in the Examples of the invention, forms elements of secondary structure, e.g. bulge loops, internal loops, hairpins, Y-structures, heterologous loops, and the like due to an "accidental" complementarity of one sequence within the polynucleotide to yet another sequence of the same polynucleotide. In the modified DNA of the invention, both duplex strands incorporate the duplex-stabilizing modification in contrast to the complex formed between an oligonucleotide component (primer or probe) and the modified DNA wherein only one strand is modified (in instances when the oligonucleotide is not modified). It has been shown that the progression of several types of DNA polymerases, from prokaryotes, phages and eukaryotes, is impeded at certain DNA sequences, which were predicted to fold into secondary structures, e.g. LaDuca R. J. et al (1983) *Biochemistry*, 22: 5177-5188; Bedinger P. et al (1989) *J. Biol. Chem.*, 264: 16880-16886; Bierne H. and Michel B. (1994) *Mol. Microbiol.*, 13: 17-23. Stabilization of the secondary structures in nucleic acids was blamed for negative results of certain duplex-stabilizing base modifications observed in RNA detection (Nguyen A. et al (2002) *BMC Biotechnology*, 2: 14; Hacia J. G. et al (1998) *Nucleic Acids Res.*, 26: 4975-4982). Thus, those skilled in the art will appreciate the unpredictability, until the present invention, of the effects of any modified dNTP or combination thereof on nucleic acid detection assays and, in particular, on the detection PCR, given these art-recognized complexities of amplification and detection reactions.

Surprisingly, however, the base-modified dNTPs of the present invention performed remarkably well in detection PCR. The experiments shown on FIGS. 5, 6 and 10 (discussed in detail herein) prove that the base-modified dNTPs used in these examples can completely substitute their respective natural nucleoside 5'-triphosphate without any damage to the detection PCR assay. The detection assays where one of the natural dNTPs was replaced with d(2-amA)TP, d(5-MeC), d(5-BrU)TP or d(5-PrU)TP showed essentially the same fluorescent signal and identical $C_t$ values. Stability of the threshold point ($C_t$) is particularly important. Any negative effect of base-modified dNTP on the amplification process would lead to reduction of the PCR yield as this would be adequately reflected in increase of the threshold. An example of this effect can be found in FIG. 7B.

All tested base-modified dNTPs apparently provided modified DNA amplicons with enhanced hybridization properties as the respective dNTP substitution allowed increasing of PCR temperatures without any losses in the assay performance. FIGS. 9 and 11 (discussed in detail herein) show a summary of the experiments conducted in FIGS. 5, 6 and 10 (discussed in detail herein), providing a better representation of the system stabilization effect. The scale of the effect varies between and among the dNTP analogs, increasing according to the following order: d(5-BrU)TP=d(5-PrU)TP<d(5-MeC) TP<d(2-amA)TP<d(5-PrU)TP+d(2-amA)TP. However, this order may not necessarily reflect the absolute tendency or ratio between thermodynamic contributions of the individual base-modified dNTPs per se, and could vary depending on the particular base composition of oligonucleotide components used in the assay. The present inventive methods benefit both of the studied detection reactions, cleavable FRET probe (TaqMan, FIGS. 5, 6 and 9) and hybridization-triggered (Scorpion, FIGS. 10 and 11).

The examples of the assays in FIG. 5 show that the present invention can be effectively combined with other conventional technologies developed for duplex stabilization, in particular, with modified primers and probes described in Lebedev Y. et al (1996) *Genet. Anal.*, 13 15-21 and Prosnyak M. I. et al (1994) *Genomics*, 21:490-494. Similar system stabilization was observed whether the base modification was incorporated into the target DNA (FIG. 5B) or into the primers and probe structures (FIG. 5C). Combination of the both approaches (FIG. 5D) led to an unprecedented accumulative effect wherein a stable system performance was observed at a temperature as high as 75° C.; a very significant achievement. The JumpStart DNA polymerase (Sigma) used herein is an antibody-blocked version of the native Taq polymerase. The polymerase is thermostable and it survives the elevated temperatures of the PCR denaturation stage expressing maximum activity and incorporating more than 60 nucleotides per second, at approximately 75° C. (Takagi M. et al (1997) *Appl. Environ. Microbiol*, 63: 4504-4510; Innis M. A. et al (1988) *Proc. Natl. Acad. Sci. USA*, 85: 9436-9440). Without being bound by any particular theory, it is speculated that the anticipated rapid reduction in the oligonucleotide hybridization properties with the PCR temperature exceeding 70° C. may be adequately compensated by an increase in the Taq polymerase activity entering into a temperature range of its optimal performance. This may explain why there is essentially no difference between the real time curves in a broad range of the temperatures from 65 to 75° C. Actually, running PCR at such elevated temperatures can be very beneficial in many ways. For example, it saves time on the temperature ramping and the time savings can be significant for some real-time instruments like the ABI 7700 or 7900 and the Bio-Rad iCycler. PCR at elevated temperatures is also more sequence specific. Although the benefits of conducting PCR at optimal temperatures are obvious, published reports of using annealing temperatures above 70° C. are exceptionally rare. Relative inefficiency of PCR at low temperatures is well known in the art and an additional extension stage (>72° C.) is commonly introduced to resolve the issue. However, even short exposure of the reaction to low temperature can trigger "mispriming" and primer-dimer formation. The main reason for using low temperatures in PCR is the DNA itself and, in particular, its structural and thermodynamic diversity. A/T-rich duplexes are significantly less stable than duplexes with elevated G/C content. Any of the exemplary duplex-stabilizing dNTPs shown in FIG. 3 can be used in practicing the present invention in nucleic acid detection assays. However, the use of the base-modified analogs of dATP and dTTP is preferred. Incorporation of these base-modified nucleotides into the amplification products stabilizes A-T base pairs. Relative instability of the natural A-T base pair versus G-C has always been an issue, rendering some of the A/T-rich targets problematic or even non-amplifiable and thus undetectable. The present invention provides an effective solution to this problem. Moreover effectiveness of the present invention is in a direct ratio to the base composition of detected nucleic acids. The greater the A/T content of the target sequences, the greater the benefit that can be achieved applying the present invention in the nucleic acid detection assays.

Incorporation of duplex-stabilizing nucleosides into DNA can stabilize a PCR amplicon to a degree where strand separation of the amplicon strands at PCR melting stage would become problematic. Such an effect was observed in the experiments shown in FIG. 7. Complete replacement of dATP and dTTP with their modified analogs d(2-amA)TP and d(5-PrU)TP led to increase of 4 cycles in $C_t$ value. It is estimated that stability of a d(2-amA)TP-d(5-PrU)TP base pair is closely approaching stability of natural G-C. G/C-rich duplexes are extremely thermostable and they are notorious for problems associated with strand separation in PCR. It was hypothesized that the application of two modified dNTPs (FIG. 7) over-stabilized the amplicon duplex. Indeed, the experiments shown in FIG. 8 proved that this was correct. A slight increase in temperature and/or time of the denaturation stage turned the $C_t$ value back to normal (cycle 26).

Figure 8:
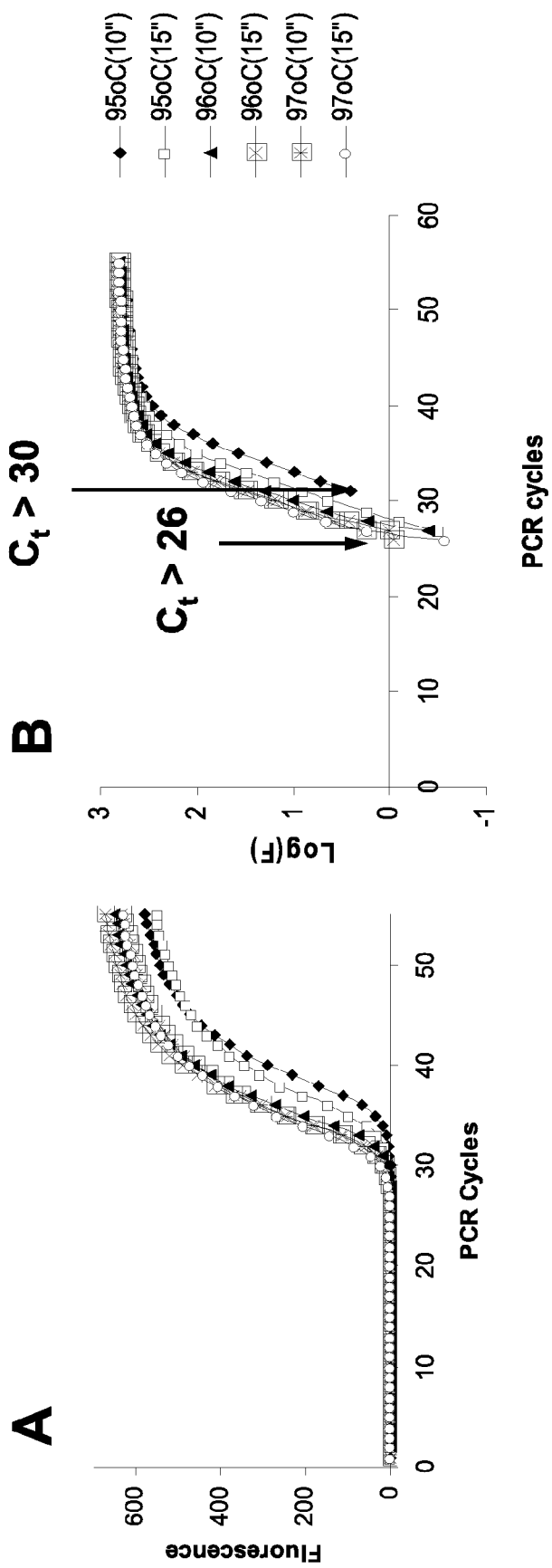

The experiments in FIG. 7 illustrate potentially limiting aspects in applicability of the present invention in detection PCR. Significantly, however, there are two ways to resolve the potential over-stabilization issue. The first approach is shown in FIG. 8. Complete strand separation in the over-stabilized amplicons can be achieved by increasing the temperature or time of PCR denaturation stage. This approach is somewhat limited by relative instability of Taq polymerase at and above 100° C. However, certain DNA polymerases isolated from thermophiles are more thermostable than Taq. For example, Pfu is a highly thermostable DNA polymerase from the hyperthermophilic archaeum Pyrococcus furiosus (Sambrook J., Russell D. W. (2001) Molecular Cloning: A Laboratory Manual, the third edition, Cold Spring Harbor Laboratory Press, Cold Spring Harbor, N.Y.). The Pfu DNA polymerase also exhibits 3' to 5' exonuclease (proofreading) activity that enables the polymerase to correct nucleotide incorporation errors. However, it has no 5' to 3' exonuclease activity and its application may be limited to the hybridization-triggered detection systems like Scorpion primer, Beacon or Eclipse probes. In a second approach, incomplete or fractional substitution of respective dNTPs can be applied. According to particular aspects, a balanced composition of dNTPs containing natural and/or duplex-stabilizing analogs can be found for every given target DNA sequence. This composition will not interfere with PCR while providing the assay stabilization. In such a composition, certain dNTPs can be completely natural while all other or some of other can be can be completely or partially substituted with the respective duplex-stabilizing analogues. Fractional or complete substitution of individual dNTP can be a mixture of two or more duplex-stabilizing analogs of the present invention. For example, dCTP can be completely or partially substituted with a mixture of d(5-MeC)TP and d(5-BrC)TP. Two mutually different approaches described herein can be applied individually or in combination thereof while practicing the present invention but avoiding the amplicon over-stabilization in PCR.

The TaqMan and Scorpion assays (see designs on FIG. 4) have been pre-developed as conventional detection systems. Application of the duplex-stabilizing dNTPs of the present invention (FIGS. 5-7 and 10) enables elevation of the PCR annealing temperatures (FIGS. 9 and 11) without any change in signal and threshold performance. The stabilization effect for every base analog used in the present invention can be determined and these data can be used in design of newly developed systems. This, in turn, provides for a successful design. The length of PCR oligonucleotides can be reduced or, alternatively, the PCR temperature can be elevated. The greater the reaction temperature, the faster all stages of the amplification reaction.

The present invention implicitly but indirectly improves hybridization properties of oligonucleotide primers and probes. Stabilization of the PCR primers is particularly important because of limited number of the duplex-stabilizing technologies that support oligonucleotide priming in PCR.

RELEVANT REFERENCES CITED

Afonina I., Zivarts M., Kutyavin I., Lukhtanov E., Gamper H. and Meyer R. B. (1997) Efficient Priming of PCR with Short Oligonucleotides Conjugated to a Minor Groove Binder. *Nucleic Acids Res.*, 25: 2657-2660.

Afonina I. A., Reed M. W., Lusby E., Shishkina I. G. and Belousov Y. S. (2002) Minor groove binder-conjugated DNA probes for Quantitative DNA detection by hybridization-triggered fluorescence. *BioTechniques*, 32: 940-949

Aizenstein B. D., Rasmussen E. B., Hall J. G., Agarwal P., Arco D., Atiles M. W., Burris D. E., Indig M. A., Law S. M., Mast A. L., Marshall D. J., Miller C. W., Oldenberg M. C., Prudent J. R., Schneiders J. M., Brow M. A. D., Lyamichev V. (2005) Methods and compositions for detecting target sequences. U.S. Pat. No. 6,913,881.

An L., Tang W., Ranalli T. A., Kim H.-J., Wytiaz J., and Kong H. (2005) Characterization of a Thermostable UvrD Helicase and its Participation in Helicase Dependent Amplification, *JBC*, 280: 28952-28958.

Andras S. C., Power J. B., Cocking E. C., Davey M. R. (2001) Strategies for signal amplification in nucleic acid detection, *Mol. Biotechnol.*, 19: 29-44.

Auer T., Sninsky J. J., Gelfand D. H. and Myers T. W. (1996) Selective amplification of RNA utilizing the nucleotide analog dITP and *Thermus thermophilus* DNA polymerase. *Nucleic Acids Res.*, 24: 5021-5026.

Ausubel F. M, Brent R., Kingston R. E., Moore D. D., Seidman J. G., and Struhl K., eds., (1993) *Current Protocols in Molecular Biology*, Vol. 1, Chapter 2, Section I, John Wiley & Sons, New York.

Ausubel F. M, Brent R., Kingston R. E., Moore D. D., Seidman J. G., Smith, J. A., and Struhl K., eds., (1994) *Current Protocols in Molecular Biology*, Vol. 1, 9.1.1-9.1.3.

Bailly C. and Waring M. J. (1995) Transferring the purine 2-amino group from guanines to adenines in DNA changes the sequence-specific binding of antibiotics, *Nucleic Acids Res.*, 23: 885-892.

Bailly C., Suh D., Waring M. J. and Chaires J. B. (1998) Binding of daunomycin to diaminopurine- and/or inosine-substituted DNA. *Biochemistry*, 37: 1033-1045.

Bailly C. and Waring M. J. (1998) The use of diaminopurine to investigate structural properties of nucleic acids and molecular recognition between ligands and DNA. *Nucleic Acids Res.,* 26: 4309-4314.

Baner J., Nilsson M., Mendel-Hartvig M., Landegren U. (1998) Signal amplification of padlock probes by rolling circle replication, *Nucleic Acids Res.,* 26: 5073-5078.

Beaucage S. L., Caruthers M. H. (1981) Deoxynucleoside phosphoramidites—A new class of key intermediates for deoxypolynucleotide synthesis, *Tetrahedron Lett.,* 22: 1859-1862.

Becker-Andre M. and Hahlbrock K. (1989) Absolute mRNA quantification using the polymerase chain reaction (PCR). A novel approach by a PCR aided transcript titration assay (PATTY), *Nucleic Acids Res.,* 17: 9437-9446.

Bedinger P., Munn M. and Alberts B. M. (1989) Sequence-specific pausing during in vitro DNA replication on double-stranded DNA templates, *J. Biol. Chem.,* 264: 16880-16886.

Belyaysky A., Vinogradova T., Rajewsky K. (1989) PCR-based cDNA library construction: general cDNA libraries at the level of a few cells. *Nucleic Acids Res.,* 17: 2919-2932.

Bierne H. and Michel B. (1994) When replication forks stop, *Mol. Microbiol.,* 13: 17-23.

Bonnet G., Tyagi S., Libchaber A. and Kramer, F. R. (1999) Thermodynamic basis of the enhanced specificity of structured DNA probes. *Proc. Natl. Acad. Sci. USA,* 96: 6171-6176.

Boom W. R., Henriette M. A., Kievits T., Lens P. F. (1993) Process for isolating nucleic acid, U.S. Pat. No. 5,234,809.

Breslauer K. J., Frank R., Blocker H., Marky L. A. (1986) Predicting DNA duplex stability from the base sequence, *Proc. Natl. Acad. Sci. USA,* 83: 3746-3750.

Brow M. A. D., Hall J. S. G., Lyamichev V., Olive D. M., Prudent J. R. (1998) Detection of nucleic acid sequences by invader-directed cleavage. U.S. Pat. No. 5,846,717.

Brow M. A. D., Hall J. S. G., Lyamichev V., Olive D. M., Prudent J. R. (1999) Detection of nucleic acid sequences by invader-directed cleavage. U.S. Pat. No. 6,001,567.

Brown E. L., Belagaje R., Ryan M. J., Khorana H. G. (1979) Chemical synthesis and cloning of a tyrosine tRNA gene, *Methods Enzymol.,* 68: 109-151.

Burgner D., D'Amato M., Kwiatkowski D. P., Loakes D. (2004) Improved allelic differentiation using sequence-specific oligonucleotide hybridization incorporating an additional base-analogue mismatch, *Nucleosides Nucleotides Nucleic Acids,* 23: 755-765.

Butkus V., Klimasauskas S., Petrauskiene L., Maneliene Z., Janulaitis A., Minchenkova L. E. and Schyolkina A. K. (1987) Synthesis and physical characterization of DNA fragments containing N4-methylcytosine and 5-methylcytosine. *Nucleic Acids Res.,* 15: 8467-8478.

Cardullo R. A., Agrawal S., Flores C., Zamecnik P. C. and Wolf D. E. (1988) Nucleic acid hybridization by nonradioactive fluorescence resonance energy transfer. *Proc. Natl. Acad. Sci. USA,* 85: 8790-8794.

Caruthers M. H., Matteucci M. D. (1984) Process for preparing polynucleotides, U.S. Pat. No. 4,458,066.

Clegg R. M. (1992) Fluorescence resonance energy transfer and nucleic acids. *Methods Enzymol.,* 211: 353-388.

Clegg R. M. (1995) Fluorescence energy transfer. *Curr. Opin. Biotech.,* 6: 103-110.

Clementi M., Menzo S., Bagnarelli P., Manzin A., Valenza A., Varaldo P. E. (1993) Quantitative PCR and RT-PCR in virology. *PCR Methods Appl.* 2:191-196.

Cleuziat P. and Mandrand B. (1998) Method for amplifying nucleic acid sequences by strand displacement using DNA/RNA chimeric primers, U.S. Pat. No. 5,824,517.

Dahlberg J. E., Lyamichev V. I., Brow M. A. D. (1997) Detection of target nucleic acid molecules using synthesis-deficient thermostable DNA polymerase. U.S. Pat. No. 5,691,142.

Dahlberg J. E., Lyamichev V. I., Brow M. A. D. (1998) Detection of target nucleic acid molecules using thermostable 5' nuclease. U.S. Pat. No. 5,837,450.

Dattagupta N., Stull P. D., Spingola M., and Kacian D. L. (2001) Isothermal strand displacement nucleic acid amplification, U.S. Pat. No. 6,214,587.

Davey C. and Malek L. T. (2000) Nucleic acid amplification process, U.S. Pat. No. 6,063,603.

Demple B., Johnson A. and Fung D. (1986) Exonuclease III and endonuclease IV remove 3' blocks from DNA synthesis primers in $H_2O_2$-damaged *Escherichia coli. Proc. Natl. Acad. Sci. USA,* 83: 7731-7735.

Didenko V. V. (2001) DNA probes using fluorescence resonance energy transfer (FRET): design and application, *BioTechniques,* 31, 1106-1121.

Dierick H., Stul M., De Kelver W., Marynen P. and Cassiman J.-J. (1993) Incorporation of dITP or 7-deaza dGTP during PCR improves sequencing of the product. *Nucleic Acids Res.,* 21: 4427-4428.

Di Giusto D. A. and King G. C. (2004) Strong positional preference in the interaction of LNA oligonucleotides with DNA polymerase and proofreading exonuclease activities: implications for genotyping assays. *Nucleic Acids Res.,* 32: e32.

Diviacco S., Norio P., Zentilin L., Menzo S., Clementi M., Biamonti G., Riva S., Falaschi A., Giacca M. (1992) A novel procedure for quantitative polymerase chain reaction by coamplification of competitive templates, *Gene,* 122: 313-320.

Dobrikov M. I., Sergueeva Z. A., Shaw B. R. (2003) Incorporation of (alpha-P-borano)-2',3'-dideoxycytidine 5'-triphosphate into DNA by drug-resistant MMLV reverse transcriptase and Taq polymerase. *Nucleosides Nucleotides Nucleic Acids,* 22(5-8): 1651-1655.

Doty P., Marmur J., Eigner J., Schildkraut C. (1960) Strand separation and specific recombination in deoxyribonucleic acids: physical chemical studies, *Proc. Natl. Acad. Sci. USA,* 46: 461-476.

Eckstein F., ed., (1991) *Oligonucleotides and Analogs: A Practical Approach.* Oxford University Press, New York.

Eftink M. R. (1991) Fluorescence quenching: theory and applications. In Lakowicz J. R. (ed.), *Topics in Fluorescence Spectroscopy.* Plenum Press, New York, V. 2: 53-126.

Fong W., Modrusan Z., McNevin J., Marostenmarki J., Zin B. and Bekkaoui F. (2000) Rapid solid-phase immunoassay for detection of methicillin-resistant *Staphylococcus aureus* using cycling probe technology. *J. Clin. Microbiol.,* 38: 2525-2529.

Förster T. (1965) Delocalized excitation and excitation transfer. In Sinanoglu, O. (ed.), *Modern Quantum Chemistry, Istanbul Lectures, part III.* Academic Press, New York: 93-137.

Freeman W. M., Walker S. J., Vrana K. E. (1999) Quantitative RT-PCR: pitfalls and potential, *Biotechniques,* 26: 112-122, 124-125.

Gaffney B. L., Marky L. A. and Jones R. A. (1984) The influence of the purine 2-amino group on DNA conformation and stability. II. Synthesis and physical characterization of d[CGT(2-NH$_2$)ACG], d[CCU(2-NH$_2$)ACG], and d[CGT(2-NH$_2$)AT(2-NH$_2$)ACG]. *Tetrahedron*, 40: 3-13.

Gait M. J., ed., (1984) *Oligonucleotide Synthesis: A Practical Approach*, IRL Practical Approach Series, IRL Press, Oxford.

Gelfand D. H., Holland P. M., Saiki R. K., Watson R. M. (1993) Homogeneous assay system using the nuclease activity of a nucleic acid polymerase, U.S. Pat. No. 5,210,015.

Gelfand D. H., Kwok S. Y., Sninsky J. J. (1995) Reduction of non-specific amplification glycosylase using DUTP and DNA uracil. U.S. Pat. No. 5,418,149.

Goldenberg O., Landt O., Schumann R. R., Gobel U. B., Hamann L. (2005) Use of locked nucleic acid oligonucleotides as hybridization/FRET probes for quantification of 16S rDNA by real-time PCR. *Biotechniques*, 38: 29-32.

Gourlain T., Sidorov A., Mignet N., Thorpe S. J., Lee S. E., Grasby J. A. and Williams D. M. (2001) Enhancing the catalytic repertoire of nucleic acids: a systematic study of linker length and rigidity. *Nucleic Acids Res.*, 29: 1898-1905.

Gu Z., Belzer S. W., Gibson C. S., Bankowski M. J., Hayden R. T. (2003) Multiplexed real-time PCR for quantitative detection of human adenovirus. *J. Clin. Microbiol.*, 41: 4636-4641.

Gundry C. N., Bernard P. S., Hermann M. G., Reed G. H. and Wittwer C. T. (1999) Rapid F508del and F508C assay using fluorescent hybridization probes. *Genet. Test.*, 3: 365-370.

Hacia J. G., Woski S. A., Fidanza J., Edgemon K., Hunt N., McGall G., Fodor S. P. A. and Collins F. S. (1998) Enhanced high density oligonucleotide array-based sequence analysis using modified nucleoside triphosphates. *Nucleic Acids Res.*, 26: 4975-4982.

Hafner G. J., Yang I. C., Wolter L. C., Stafford M. R., and Giffard P. M. (2001) Isothermal amplification and multimerization of DNA by Bst DNA polymerase. *BioTechniques*, 30, 852-867

Hall J. G., Lyamichev V. I., Mast A. L., Brow M. A. D. (1999) Detection of nucleic acids by multiple invasive cleavages. U.S. Pat. No. 5,994,069.

Harvey J. J., Lee S. P., Chan K., Kim J. H., Hwang E.-S., Cha C.-Y., Knutson J. R. and Han M. K. (2004) Characterization and application of CataCleave probe in real-time detection assays, *Anal. Biochem.*, 333: 246-255.

Held H. A. and Benner S. A (2002) Challenging artificial genetic systems: thymidine analogs with 5-position sulfur functionality. *Nucleic Acids Res.*, 30: 3857-3869.

Heller M. J. and Morrison L. E. (1985) Chemiluminescent and fluorescent probes for DNA hybridization. In Kingsbury, D. T. and Falkow, S. (eds.), *Rapid Detection and Identification of Infectious Agents*. Academic Press, New York, 245-256.

Higuchi R., Dollinger G., Walsh P. S., and Griffith R. (1992) Simultaneous amplification and detection of specific DNA sequences. *Biotechnology*, 10: 413-417.

Higuchi R., Fockler C., Dollinger G., and Watson R. (1993) Kinetic PCR: Real time monitoring of DNA amplification reactions. *Biotechnology*, 11: 1026-1030.

Howard F. B., Frazier J. and Miles H. T. (1966) A new polynucleotide complex stabilized by three interbase hydrogen bonds, poly-2-aminoadenylic acid+polyuridylic acid. *J. Biol. Chem.*, 241: 4293-4295.

Howard F. B., Frazier J. and Miles H. T. (1976) Poly(2-aminoadenylic acid): Interaction with poly(uridylic acid). *Biochemistry*, 15: 3783-3795.

Howard F. B. and Miles H. T. (1984) 2NH$_2$A•T helices in the ribo- and deoxypolynucleotide series. Structural and energetic consequence of 2NH$_2$A substitution. *Biochemistry*, 23: 6723-6732.

Innis M. A., Myambo K. B., Gelfand D. H. and Brow M. A. D. (1988) DNA sequencing with *Thermus aquaticus* DNA polymerase and direct sequencing of polymerase chain reaction-amplified DNA. *Proc. Natl. Acad. Sci. USA*, 85: 9436-9440.

Jäger S. and Famulok M. (2004) Generation and enzymatic amplification of high-density functionalized DNA double strands. *Angew. Chem. Int. Ed.*, 43: 3337-3340.

Johnson M. P., Haupt L. M., Griffiths L. R. (2004) Locked nucleic acid (LNA) single nucleotide polymorphism (SNP) genotype analysis and validation using real-time PCR. *Nucleic Acids Res.*, 32: e55.

Kempeneers V., Renders M., Froeyen M. and Herdewijn P. (2005) Investigation of the DNA-dependant cyclohexenyl nucleic acid-dependant DNA polymerization. *Nucleic Acids Res.*, 33: 3828-3836.

Kornberg A., and Baker T. (1992) *DNA Replication*, Second Edition, W. H. Freeman and Company, New York.

Kurn N. (2001) Methods and compositions for linear isothermal amplification of polynucleotide sequences, using a RNA-DNA composite primer, U.S. Pat. No. 6,251,639.

Kutyavin I. V., Afonina I. A., Mills A., Gorn V. V., Lukhtanov E. A., Belousov E. S., Singer M. J., Walburger D. K., Lokhov S. G., Gall A. A., Dempcy R., Reed M. W., Meyer R. B. and Hedgpeth J. (2000) 3'-Minor groove binder-DNA probes increase sequence specificity at PCR extension temperatures. *Nucleic Acids Res.*, 28: 655-661.

Kutyavin I. V., Lukhtanov E. A., Gamper H. B. and Meyer R. B. (1997) Oligonucleotides with conjugated dihydropyrroloindole tripeptides: base composition and backbone effects on hybridization. *Nucleic Acids Res.*, 25: 3718-3723.

Kutyavin I. V., Milesi D., Hoekstra M. F. (2004) Abasic site endonuclease assay. US Patent Application #20040101893.

Kuwahara M., Hososhima S., Takahata Y., Kitagata R., Shoji A., Hanawa K., Ozaki A. N., Ozaki H., Sawai H. (2003) Simultaneous incorporation of three different modified nucleotides during PCR. *Nucleic Acids Res. Suppl.*, 3: 37-38.

LaDuca R. J., Fay P. J., Chuang C., McHenry C. S., Bambara R. A. (1983) Site-specific pausing of deoxyribonucleic acid synthesis catalyzed by four forms of *Escherichia coli* DNA polymerase III. *Biochemistry*, 22: 5177-5188.

Latorra D., Arar K., Hurley J. M. (2003) Design considerations and effects of LNA in PCR primers, *Mol. Cell. Probes*, 17: 253-259.

Latorra D., Campbell K., Wolter A., Hurley J. M. (2003) Enhanced allele-specific PCR discrimination in SNP genotyping using 3' locked nucleic acid (LNA) primers, *Hum. Mutat.*, 22: 79-85.

Lee S. E., Sidorov A., Gourlain T., Mignet N., Thorpe S. J., Brazier J. A., Dickman M. J., Hornby D. P., Grasby J. A. and Williams D. M. (2001) Enhancing the catalytic repertoire of nucleic acids: a systematic study of linker length and rigidity. *Nucleic Acids Res.*, 29: 1565-1573.

Lebedev Y., Akopyans N., Azhikina T., Shevchenko Y., Potapov V., Stecenko D., Berg D., Sverdlov E. (1996) Oligonucleotides containing 2-aminoadenine and 5-methylcytosine are more effective as primers for PCR amplification than their nonmodified counterparts, *Genet. Anal.*, 13, 15-21.

Lehninger A. L. (1975) *Biochemistry*, 2nd edition. New York, Worth Publishers, Inc.

Lewin S. R., Vesanen M, Kostrikis L., Hurley A., Duran M., Zhang L., Ho D. D., Markowitz M. (1999) Use of real-time PCR and molecular beacons to detect virus replication in human immunodeficiency virus type 1-infected individuals on prolonged effective antiretroviral therapy. *J. Virol.*, 73: 6099-6103.

Lie Y. S. and Petropoulos C. J. (1998) Advances in quantitative PCR technology: 5' nuclease assays. *Curr. Opin. Biotech.*, 9: 43-48.

Livak K. J., Flood S. J. A, Marmaro J., Giusti W., Deetz K. (1995) Oligonucleotide with fluorescent dyes at opposite ends provide a quenched probe system useful for detecting PCR product and nucleic acid hybridization. *PCR Methods and Applications*, 4: 357-362.

Livak K. J., Flood S. J. A., Marmaro J. and Mullah K. B. (1998) Self-quenching fluorescent probe. U.S. Pat. No. 5,723,591.

Lizardi P. (1998) Rolling circle replication reporter systems, U.S. Pat. No. 5,854,033.

Lutfalla G. and Uze G. (2006) Performing quantitative reverse-transcribed polymerase chain reaction experiments, *Methods Enzymol.*, 410: 386-400.

Mackay I. M., Arden K. E., Nitsche A. (2002) Real-time PCR in virology, *Nucleic Acids Res.*, 30: 1292-1305.

Mackay J., Landt O. (2007) Real-time PCR fluorescent chemistries, *Methods Mol. Biol.*, 353: 237-262.

Marras S. A. E., Kramer F. R. and Tyagi S. (2002) Efficiencies of fluorescence resonance energy transfer and contact-mediated quenching in oligonucleotide probes. *Nucleic Acids Res.*, 30: e122.

Matthes E., Reimer K., von Janta-Lipinski M., Meisel H. and Lehmann C. (1991) Comparative inhibition of hepatitis B virus DNA polymerase and cellular DNA polymerase by triphosphates of sugar-modified 5-methyldeoxycytidines and of other nucleoside analogs. *Antimicrob. Agents Chemother.*, 35: 1254-1257.

McPherson M. J., Quirke P., Taylor G. R., eds (1991) *PCR: A Practical Approach*. IRL Press, Oxford.

McPherson M. J., Quirke P., Taylor G. R., eds (1995) *PCR2: A Practical Approach*. IRL Press, Oxford.

Miller S. A., Dykes D. D. and Polesky H. F. (1988) A simple salting out procedure for extracting DNA from human nucleated cells. *Nucleic Acids Res.*, 16: 1215.

Modruzan Z., C., Wheeler D., Pirseyedi M. and Bryan R. (2000) CPT-EIA assays for the detection of vancomycin resistant vanA and vanB genes in enterococci. *Diagn. Microbiol. Infect. Dis.*, 37: 45-50.

Mullis K. B. (1987) Process for amplifying nucleic acid sequences, U.S. Pat. No. 4,683,202.

Mullis K. B., Erlich H. A., Arnheim N., Horn G. T., Saiki R. K., and Scharf S. J. (1987) Process for amplifying, detecting, and/or -cloning nucleic acid sequences, U.S. Pat. No. 4,683,195.

Marmur J., Lane D. (1960) Strand separation and specific recombination in deoxyribonucleic acids: biological studies, *Proc. Natl. Acad. Sci. USA*, 46: 453-461.

Narang S. A., Hsiung H. M., Brousseau R. (1979) Improved phosphotriester method for the synthesis of gene fragments, *Methods Enzymol.*, 68: 90-98.

Nazarenko I., Lowe B., Darfler M., Ikonomi P., Schuster D., Rashtchian A. (2002) Multiplex quantitative PCR using self-quenched primers labeled with a single fluorophore. *Nucleic Acids Res.*, 30: e37.

Nazarenko I., Pires R., Lowe B., Obaidy M., Rashtchian A. (2002) Effect of primary and secondary structure of oligodeoxyribonucleotides on the fluorescent properties of conjugated dyes. *Nucleic Acids Res.*, 30: 2089-2195.

Nguyen A., Zhao C., Donis D. and Mazumder A. (2002) Quantitative assessment of the use of modified nucleoside triphosphates in expression profiling: differential effects on signal intensities and impacts on expression ratios. *BMC Biotechnology*, 2: 14.

Niesters H. G. (2001) Quantitation of viral load using real-time amplification techniques, *Methods*, 25: 419-429.

Notomi T. and Hase T. (2002) Process for synthesizing nucleic acid, U.S. Pat. No. 6,410,278.

Notomi T., Okayama H., Masubuchi H., Yonekawa T., Watanabe K., Amino N., and Hase T. (2000) Loop-mediated isothermal amplification of DNA, *Nucleic Acids Res.*, 28, e63.

Oehlenschlager F., Schwille P. and Eigen M. (1996) Detection of HIV-1 RNA by nucleic acid sequence-based amplification combined with fluorescence correlation spectroscopy. *Proc. Natl. Acad. Sci. USA*, 93, 12811-12816.

Ono T., Scalf M. and Smith L. M. (1997) 2'-Fluoro modified nucleic acids: polymerase-directed synthesis, properties and stability to analysis by matrix-assisted laser desorption/ionization mass spectrometry. *Nucleic Acids Res.*, 25: 4581-4588.

Ono A. and Ueda T. (1987) Synthesis of decadeoxyribonucleotides containing $N^6$-methyladenine, $N^4$-methylcytosine and 5-methylcytosine: recognition and cleavage by restriction endonucleases (Nucleotides and Nucleosides Part 74). *Nucleic Acids Res.*, 15: 219-232.

Ortiz E., Estrada G. and Lizardi P. M. (1998) PNA molecular beacons for rapid detection of PCR amplicons. *Mol. Cell. Probes*, 12, 219-226.

Piatek A. S., Tyagi S., Pol A. C., Telenti A., Miller L. P., Kramer F. R., Alland D. (1998) Molecular beacon sequence analysis for detecting drug resistance in *Mycobacterium tuberculosis*. *Nat. Biotechnol.*, 16: 359-363.

Porter K. W., Briley J. D., Shaw B. R. (1997) Direct PCR sequencing with boronated nucleotides. *Nucleic Acids Res.*, 25: 1611-1617.

Prosnyak M. I., Veselovskaya S. I., Myasnikov V. A., Efremova E. J., Potapov V. K., Limborska S. A., Sverdlov E. D. (1994) Substitution of 2-aminoadenine and 5-methylcytosine for adenine and cytosine in hybridization probes increases the sensitivity of DNA fingerprinting. *Genomics*, 21: 490-494.

Prudent J. R., Hall J. G., Lyamichev V. I., Brow M. A. D., Dahlberg J. E. (1999) Invasive cleavage of nucleic acids. U.S. Pat. No. 5,985,557.

Prudent J. R., Hall J. G., Lyamichev V. I., Brow M. A. D. (2000) Cleavage of nucleic acids. U.S. Pat. No. 6,090,543.

Prudent J. R., Hall J. G., Lyamichev V. I., Brow M. A. D., Dahlberg J. E. (2002) Invasive cleavage of nucleic acids. U.S. Pat. No. 6,348,314.

Prudent J. R., Hall J. G., Lyamichev V. I., Brow M. A. D., Dahlberg J. E. (2005) Nucleic acid detection assays. U.S. Pat. No. 6,875,572

Reid R., Mar E.-C., Huang E.-S. and Topal M. D. (1988) Insertion and extension of acyclic, dideoxy, and Ara nucleotides by Herpesviridae, Human α and Human β polymerases. *J. Biol. Chem.*, 263: 3898-3904.

Robelek R., Niu L., Schmid E. L., Knoll W. (2004) Multiplexed hybridization detection of quantum dot-conjugated DNA sequences using surface plasmon enhanced fluorescence microscopy and spectrometry, *Anal. Chem.*, 76: 6160-6165.

Sambrook J., Fritsch E. F. and Maniatis T. (1989) *Molecular Cloning: A Laboratory Manual*, 2nd Edition. Cold Spring Harbor Lab. Cold Spring Harbor, N.Y.

Sambrook J., Russell D. W. (2001) Molecular Cloning: A Laboratory Manual, the third edition, Cold Spring Harbor Laboratory Press, Cold Spring Harbor, N.Y.

SantaLucia J. Jr. (1998) A unified view of polymer, dumbbell, and oligonucleotide DNA nearest-neighbor thermodynamics. *Proc. Natl. Acad. Sci. USA*, 95: 1460-1465.

Sawai H., Ozaki-Nakamura A., Mine M., Ozaki H. (2002) Synthesis of new modified DNAs by hyperthermophilic DNA polymerase: substrate and template specificity of functionalized thymidine analogues bearing a sp3-hybridized carbon at the C5 alpha-position for several DNA polymerases. *Bioconjug. Chem.*, 13: 309-316.

Scheit K. H. and Rackwitz H.-R. (1982) Synthesis and physicochemical properties of two analogs of poly(dA); poly(2-aminopurine-9-β-D-deoxyribonucleotide) and poly 2-amino-deoxyadenylic acid. *Nucleic Acids Res.*, 10: 4059-4069.

Schneeberger C., Speiser P., Kury F., Zeillinger R. (1995) Quantitative detection of reverse transcriptase-PCR products by means of a novel and sensitive DNA stain. *PCR Methods Appl.*, 4: 234-238.

Schweitzer B. and Kingsmore S. (2001) Combining nucleic acid amplification and detection. *Curr. Opin. Biotech.*, 12: 21-27.

Seela F. and Röling A. (1992) 7-Deazapurine containing DNA: efficiency of c7GdTP, c7AdTP and c7IdTP incorporation during PCR-amplification and protection from endodeoxyribonuclease hydrolysis. *Nucleic Acids Res.*, 20: 55-61.

Selvin P. R. (1995) Fluorescence resonance energy transfer. *Methods Enzymol.*, 246: 300-334.

Shaw B. R., Porter K. W., Sergueev D. (2004) Method of nucleic acid sequencing. U.S. Pat. No. 6,808,897.

Simeonov A. and Nikiforov T. T. (2002) Single nucleotide polymorphism genotyping using short, fluorescently labeled locked nucleic acid (LNA) probes and fluorescence polarization detection, *Nucleic Acids Res.*, 30: e91.

Simpson D., Crosby R. M., and Skopek T. R. (1988) A method for specific cloning and sequencing of human hprt cDNA for mutation analysis. *Biochem. Biophys. Res. Commun.*, 151: 487-492.

Sorge J. A. (2001) Methods for detection of a target nucleic acid using a probe comprising secondary structure, U.S. Pat. No. 6,589,743.

Spargo C. A., Fraiser M. S., Van Cleve M., Wright D. J., Nycz C. M., Spears P. A., Walker G. T. (1996) Detection of *M. tuberculosis* DNA using thermophilic strand displacement amplification, *Molecular and Cellular Probes*, 10: 247-256.

Strauss P. R., Beard W. A., Patterson T. A. and Wilson S. H. (1997) Substrate binding by human apurinic/apyrimidinic endonuclease indicates a Briggs-Haldane mechanism. *J. Biol. Chem.*, 272: 1302-1307.

Stryer L. and Haugland R. P. (1967) Energy transfer: a spectroscopic ruler. *Proc. Natl. Acad. Sci. USA*, 58: 719-726.

Summers J. S. and Shaw B. R. (2001) Boranophosphates as mimics of natural phosphodiesters in DNA. *Current Medicinal Chemistry*, 8: 1147-1155.

Szer W. (1965) Secondary structure of poly-5-methylcytidylic acid. *Biochem. Biophys. Res. Commun.*, 20: 182-186.

Szer W. and Shugar D. (1966) The structure of poly-5-methylcytidylic acid and its twin-stranded complex with poly-inosinic acid. *J. Mol. Biol.*, 17: 174-187.

Takagi M., Nishioka M., Kakihara H., Kitabayashi M., Inoue H., Kawakami B., Oka M. and Imanaka T. (1997) Characterization of DNA polymerase from *Pyrococcus* sp. strain KOD1 and its application to PCR. *Appl. Environ. Microbiol.*, 63: 4504-4510.

Tecott L., Barchas J. D., Eberwine J. (1992) In situ transcription in cells and tissues, U.S. Pat. No. 5,168,038.

Thelwell N., Millington S., Solinas A., Booth J. and Brown T. (2000) Mode of action and application of Scorpion primers to mutation detection. *Nucleic Acids Res.*, 28: 3752-3761.

Townsend L. B., ed. (1988) Chemistry of Nucleosides and Nucleotides, Plenum Press, NY.

Tyagi S. and Kramer F. R. (1996) Molecular beacons-probes that fluoresce upon hybridization. *Nat. Biotechnol.*, 14: 303-308.

Tyagi S., Kramer F. R., Lizardi P. M. (1999) Detectably labeled dual conformation oligonucleotide probes, assays and kits, U.S. Pat. No. 5,925,517.

Tyagi S., Marras S. A. E. and Kramer F. R. (2000) Wavelength-shifting molecular beacons. *Nat. Biotechnol.*, 18: 1191-1196.

Uesugi S., Miyashiro H., Tomita K.-I. and Ikehara M. (1986) Synthesis and properties of d(ATACGCGTAT) and its derivatives containing one and two 5-methylcytosine residues. Effect of the methylation on deoxyribonucleic acid conformation. *Chem. Pharm. Bull.*, 34: 51-60.

Vaghefi M., ed. (2005) Nucleoside Triphosphates and their Analogs: Chemistry, Biochemistry, and Biological Applications, Taylor & Francis.

Vermeulen N., Adams D., Afonina I., Ahmadian M., Belousov Y., Dempcy R., Gorn V., Kutyavin I., Metcalf, M., Milesi D., Mills A., Reed M. W., Sanders S., Scarr N., Shishkina I., Vorobiev A., Walburger D., Wald A., Yau E. (2002) Single nucleotide polymorphism detection with MGB Eclipse™ assays. *J. Clin. Ligand Assay*, 25: 268-275.

Vincent M., Xu Y. and Kong H. (2004) Helicase Dependent Isothermal DNA Amplification, *EMBO reports*, 5: 795-800.

Walker G. T., Linn C. P. and Nadeau J. G. (1996) DNA detection by strand displacement amplification and fluorescence polarization with signal enhancement using DNA binding protein. *Nucleic Acids Res.*, 24, 384-353.

Walker G. T., Little M. C., Nadeau J. G. and Shank D. D. (1992) Isothermal in vitro amplification of DNA by a restriction enzyme/DNA polymerase system. *Proc. Natl. Acad. Sci. USA*, 89: 392-396.

Walker G. T., Little M. C., and Nadeau J. G. (1993) Nucleic acid target generation. U.S. Pat. No. 5,270,184

Walsh P. S., Metzger D. A., and Higuchi R. (1991) Chelex 100 as a medium for simple extraction of DNA for PCR-based typing from forensic material. *Biotechniques*, 10: 506-513.

Wang J. X., Sergueev D. S. and Shaw B. R. (2005) The effect of a single boranophosphate substitution with defined configuration on the thermal stability and conformation of a DNA duplex. *Nucleosides Nucleotides Nucleic Acids*, 24(5-7): 951-955.

Ward B., Snyder L. M., Li C., Song K., Opper K. E., Uder S., Hernan R. (2005) Recombinant DNA processes using a dNTP mixture containing modified nucleotides. U.S. Pat. No. 6,902,914.

Whitcombe D., Theaker J., Guy S. P., Brown T., Little S. (1999) Detection of PCR products using self-probing amplicons and fluorescence. *Nature Biotech.*, 17: 804-807.

Wilson III D. M., Takeshita M. and Demple B. (1997) Abasic site binding by the human apurinic endonuclease, Ape, and determination of the DNA contact sites. *Nucleic Acids Res.*, 25: 933-939.

Wittwer C. T., Ririe K. M., Rasmussen R. P. (2001) Monitoring amplification of DNA during PCR, U.S. Pat. No. 6,174,670.

Wittwer C. T., Ririe K. M., Rasmussen R. P. (2003) Monitoring hybridization during PCR using SYBR™ Green I, U.S. Pat. No. 6,569,627.

Wong K. K. and McClelland, M. (1991) PCR with 5-methyl-dCTP replacing dCTP. *Nucleic Acids Res.*, 19: 1081-1085.

Yi J., Zhang W., Zhang D. Y. (2006) Molecular Zipper: a fluorescent probe for real-time isothermal DNA amplification, *Nucleic Acids Res.*, 34: e81.

You Y., Moreira B. G., Behlke M. A. and Owczarzy R. (2006) Design of LNA probes that improve mismatch discrimination. *Nucleic Acids Res.*, 34: e60.

The invention claimed is:

1. A method for the detection of a target nucleic acid in a sample, comprising:
providing a reaction mixture comprising a target nucleic acid, at least one oligonucleotide primer, a DNA polymerase, and a mixture of deoxynucleoside 5'-triphosphates containing at least one base-modified duplex-stabilizing dNTP;
amplifying the target nucleic acid, wherein the at least one base-modified duplex-stabilizing dNTP incorporates into amplicons providing copies of a modified DNA with enhanced hybridization properties;
providing at least one oligonucleotide probe and hybridizing the at least one oligonucleotide probe to the modified DNA to form a complex; and
detecting the complex, wherein presence of the complex is indicative of the presence of the target nucleic acid in the sample.

2. The method of claim 1, wherein the target nucleic acid comprises at least one of DNA and RNA.

3. The method of claim 1, wherein the target nucleic acid is RNA and amplifying of the target nucleic acid includes a stage wherein at least one DNA copy of said RNA is synthesized using a reverse transcriptase.

4. The method of claim 1, wherein more than one oligonucleotide primer is used to amplify the target nucleic acid, and wherein the modified DNA serves as a template for at least one of said oligonucleotide primers at any stage of the amplification.

5. The method of claim 1, wherein a plurality of target nucleic acids are amplified and detected.

6. The method of claim 5, wherein at least one oligonucleotide primer and at least one oligonucleotide probe is provided for every target nucleic acid amplified and detected.

7. The method of claim 5, wherein more than one of the oligonucleotide primers is provided for every said target nucleic acid amplified and detected and wherein at least one of the modified DNAs serves as a template for at least one of said oligonucleotide primer at any stage of the amplification.

8. The method of claim 1, wherein detection of the target nucleic acid is performed after the amplification.

9. The method of claim 1, wherein detection of the target nucleic acid is performed in real time.

10. The method of claim 1, wherein the base-modified duplex-stabilizing dNTP represents a fraction of the respective natural dNTP or completely replaces the respective natural dNTP.

11. The methods of claim 1, wherein said reaction mixture comprises more than one of said base-modified duplex-stabilizing dNTP, in each case either replacing or representing a fraction of the respective natural dNTP.

12. The method of claim 1, wherein said base-modified duplex-stabilizing dNTP is of Formula I:

-continued

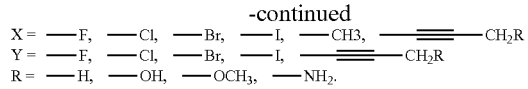
R= —H, —OH, —OCH₃, —NH₂.

13. The method of claim 1, wherein amplifying and detecting of the target nucleic acid is performed to measure the amount of said target nucleic acid in said sample.

14. The method of claim 1, wherein amplifying of the target nucleic acid comprises use of isothermal amplification.

15. The method of claim 1, wherein amplifying of the target nucleic acid comprises use of detection PCR.

16. The method of claim 1, wherein the at least one oligonucleotide primer contains a label and said label is used in detecting of said modified DNA.

17. The method of claim 16, wherein said label is a fluorescent label.

18. The method of claim 1, wherein the at least one oligonucleotide primer comprises a duplex-stabilizing modification comprising at least one of modified nucleotides and/or a tail conjugated to the 5'-end of said oligonucleotide primer.

19. The method of claim 18, wherein the tail comprises at least one of an intercalator and a minor groove binder.

20. The method of claim 1, wherein detecting of the modified DNA comprises use of a detecting agent, wherein said detecting agent interacts with the modified DNA providing a detection signal, and wherein detection of the signal is indicative of the presence of the modified DNA in the reaction mixture.

21. The method of claim 20, wherein the detecting agent comprises a fluorescent agent, and wherein the fluorescent agent changes its fluorescence properties upon interaction with said modified DNA thereby providing the detection signal.

22. The method of claim 21, wherein the fluorescent agent comprises a SYBR Green dye.

23. The method of claim 1, wherein the at least one oligonucleotide primer and the at least one oligonucleotide probe are portions or fragments of the same molecule.

24. The method of claim 1, wherein a plurality of target nucleic acids are amplified and detected, and wherein at least one said oligonucleotide primer is provided for every target nucleic acid amplified and/or detected.

25. The method of claim 1, wherein at least one of a plurality of oligonucleotide primers and a plurality of oligonucleotide probes are used in amplifying and/or detecting the target nucleic acid.

26. The method of claim 1, wherein at least one of the oligonucleotide primers, oligonucleotide probes, and modified DNAs is immobilized on a solid support at the amplifying or detecting stages, or at both stages.

27. The method of claim 1, wherein the base-modified duplex-stabilizing dNTP represents a fraction of the respective natural dNTP or completely replaces the respective natural dNTP.

28. The method of claim 1, wherein at least one of the oligonucleotide primer, oligonucleotide probe, and modified DNA contains a label and wherein this label affords detecting of the modified DNA.

29. The method of claim 28, wherein the at least one oligonucleotide probe contains the label.

30. The method of claim 29, wherein the label comprises at least one of a fluorescent label and a fluorescence-polarization label.

31. The method of claim 1, wherein the oligonucleotide probe is a FRET probe, wherein the FRET probe changes its fluorescent properties upon forming the complex with the modified DNA, and wherein the changes are indicative of the presence of the complex.

32. The method of claim 31, wherein the FRET probe comprises a hybridization-triggered FRET probe.

33. The method of claim 32, wherein the hybridization-triggered FRET probe comprises at least one of a Scorpion primer and a Beacon probe.

34. The method of claim 31, wherein the FRET probe comprises at least one of a cleavable FRET probe and a cleavable FRET probe comprising a TaqMan probe.

35. The method of claim 15, wherein the detection PCR is performed using at least two oligonucleotide primers, and wherein the oligonucleotide primers provide for exponential amplification of the target nucleic acid.

36. The method of claim 35, wherein the detection PCR comprises quantitative PCR.

37. A method for the detection of a target nucleic acid in a sample, comprising:
amplifying the target nucleic acid using detection PCR in a reaction mixture comprising:
a target nucleic acid, at least two oligonucleotide primers to provide for exponential amplification of the target nucleic acid, a DNA polymerase, and a mixture of deoxynucleoside 5'-triphosphates containing at least one base-modified duplex-stabilizing dNTP, wherein the at least one base-modified duplex-stabilizing dNTP incorporates into amplicons providing copies of a modified DNA with enhanced hybridization properties; and
detecting said modified DNA using at least one oligonucleotide probe that hybridizes to said modified DNA to form a complex, and detecting the complex, wherein presence of the complex is indicative of the presence of the target nucleic acid in the sample.

38. The method of claim 37, wherein the target nucleic acid comprises DNA.

39. The method of claim 37, wherein the target nucleic acid is RNA and amplifying the target nucleic acid includes a stage wherein at least one DNA copy of said RNA is synthesized using a reverse transcriptase.

40. The method of claim 37, wherein one of the oligonucleotide primers and the oligonucleotide probe are portions of fragments of the same molecule.

41. The method of claim 37, wherein a plurality of target nucleic acids are amplified and detected, and wherein at least two of the oligonucleotide primers and at least one of the oligonucleotide probes are provided for every target nucleic acid.

42. The method of claim 37, wherein detecting the modified DNA is performed after the amplification.

43. The method of claim 37, wherein detection of said target nucleic acid is performed in real time.

44. The method of claim 37, wherein at least one of the oligonucleotide primer, oligonucleotide probe and modified DNA is immobilized on a solid support at the amplifying or detecting stages, or at both stages.

45. The method of claim 37, wherein the base-modified duplex-stabilizing dNTP represents a fraction of the respective natural dNTP or completely replaces the respective natural dNTP.

46. The method of claims 37, wherein amplifying the target nucleic acid comprises use of more than one base-modified duplex-stabilizing dNTP, in each case either replacing or representing a fraction of the respective natural dNTP.

47. The method of claim 37, wherein the base-modified duplex-stabilizing dNTP is of Formula I:

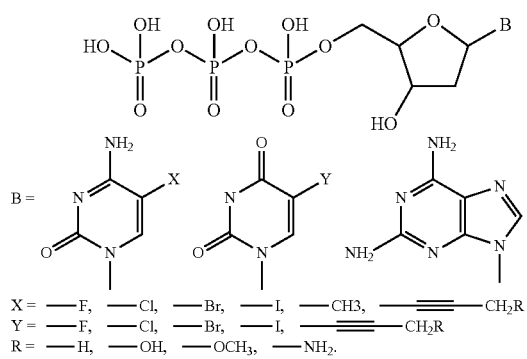

48. The method of claim 37, wherein amplifying and detecting of the target nucleic acid is performed to measure the amount of said target nucleic acid in the sample.

49. The method of claim 37, wherein the oligonucleotide probe contains a label.

50. The method of claim 49, wherein the label comprises at least one of a fluorescent label and a fluorescence-polarization label.

51. The method of claim 37, wherein either one of the oligonucleotide primer or both primers, or the oligonucleotide probe, or both the primer or primers and the probe contain one or more duplex-stabilizing modification comprising at least one of modified nucleotides and/or a tail conjugated to the 5'-end of said oligonucleotide primer.

52. The method of claim 51, wherein the at least one oligonucleotide primer comprises a duplex-stabilizing modification comprising at least one of modified nucleotides and/or a tail conjugated to the 5'-end of said oligonucleotide primer, and wherein the tail comprises at least one of an intercalator and a minor groove binder.

53. The method of claim 37, wherein the oligonucleotide probe comprises a FRET probe, wherein the FRET probe changes its fluorescent properties upon forming the complex with the modified DNA, and wherein the changes are indicative of the presence of the complex.

54. The method of claim 53, wherein the FRET probe comprises a hybridization-triggered FRET probe.

55. The method of claim 54, wherein the hybridization-triggered FRET probe comprises at least one of a Scorpion primer and a Beacon probe.

56. The method of claim 53, wherein the FRET probe comprises at least one of a cleavable FRET probe and a cleavable FRET probe comprising a TaqMan probe.

57. The method of claim 37, wherein the detection PCR comprises quantitative PCR.

* * * * *

SEQUENCE LISTING

```
<160> NUMBER OF SEQ ID NOS: 28

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide

<400> SEQUENCE: 1
tattaataat attattaaat at                                                 22

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide

<400> SEQUENCE: 2
tatcaataat attattaaat at                                                 22

<210> SEQ ID NO 3
<211> LENGTH: 22
<212> TYPE: DNA
<213> ORGANISM: Artificial Sequence
<220> FEATURE:
<223> OTHER INFORMATION: Oligonucleotide

<400> SEQUENCE: 3
tatcaataat gttattaaat at                                                 22

<210> SEQ ID NO 4
<211> LENGTH: 22
<212> TYPE: DNA
<213> ORGANISM: Artificial Sequence
<220> FEATURE:
<223> OTHER INFORMATION: Oligonucleotide

<400> SEQUENCE: 4
tatcaatgat gttattaaat at                                                 22

<210> SEQ ID NO 5
<211> LENGTH: 22
<212> TYPE: DNA
<213> ORGANISM: Artificial Sequence
<220> FEATURE:
<223> OTHER INFORMATION: Oligonucleotide

<400> SEQUENCE: 5
tatcaatgat gttattagat at                                                 22

<210> SEQ ID NO 6
<211> LENGTH: 22
```

```
<212> TYPE: DNA
<213> ORGANISM: Artificial Sequence
<220> FEATURE:
<223> OTHER INFORMATION: Oligonucleotide

<400> SEQUENCE: 6
catcaatgat gttattagat at                                          22

<210> SEQ ID NO 7
<211> LENGTH: 22
<212> TYPE: DNA
<213> ORGANISM: Artificial Sequence
<220> FEATURE:
<223> OTHER INFORMATION: Oligonucleotide

<400> SEQUENCE: 7
catcagtgat gttattagat at                                          22

<210> SEQ ID NO 8
<211> LENGTH: 22
<212> TYPE: DNA
<213> ORGANISM: Artificial Sequence
<220> FEATURE:
<223> OTHER INFORMATION: Oligonucleotide

<400> SEQUENCE: 8
catcagtgat gtcattagat at                                          22

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide

<400> SEQUENCE: 9
catcagtgat gtcattagac at                                          22

<210> SEQ ID NO 10
<211> LENGTH: 22
<212> TYPE: DNA
<213> ORGANISM: Artificial Sequence
<220> FEATURE:
<223> OTHER INFORMATION: Oligonucleotide

<400> SEQUENCE: 10
catcagtgac gtcattagac at                                          22

<210> SEQ ID NO 11
<211> LENGTH: 22
<212> TYPE: DNA
<213> ORGANISM: Artificial Sequence
<220> FEATURE:
<223> OTHER INFORMATION: Oligonucleotide

<400> SEQUENCE: 11
catcagtgac gtcattagac ac                                          22

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide

<400> SEQUENCE: 12
catcagtgac gtcactagac ac                                          22
```

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide

<400> SEQUENCE: 13
catcagtgac gtcactggac ac                                              22

<210> SEQ ID NO 14
<211> LENGTH: 22
<212> TYPE: DNA
<213> ORGANISM: Artificial Sequence
<220> FEATURE:
<223> OTHER INFORMATION: Oligonucleotide

<400> SEQUENCE: 14
cgtcagtgac gtcactggac ac                                              22

<210> SEQ ID NO 15
<211> LENGTH: 22
<212> TYPE: DNA
<213> ORGANISM: Artificial Sequence
<220> FEATURE:
<223> OTHER INFORMATION: Oligonucleotide

<400> SEQUENCE: 15
cgtcagtggc gtcactggac ac                                              22

<210> SEQ ID NO 16
<211> LENGTH: 22
<212> TYPE: DNA
<213> ORGANISM: Artificial Sequence
<220> FEATURE:
<223> OTHER INFORMATION: Oligonucleotide

<400> SEQUENCE: 16
cgtcagtggc gtcgctggac ac                                              22

<210> SEQ ID NO 17
<211> LENGTH: 22
<212> TYPE: DNA
<213> ORGANISM: Artificial Sequence
<220> FEATURE:
<223> OTHER INFORMATION: Oligonucleotide

<400> SEQUENCE: 17
cgtcagtggc gtcgctggac gc                                              22

<210> SEQ ID NO 18
<211> LENGTH: 22
<212> TYPE: DNA
<213> ORGANISM: Artificial Sequence
<220> FEATURE:
<223> OTHER INFORMATION: Oligonucleotide

<400> SEQUENCE: 18
cgccagtggc gtcgctggac gc                                              22

<210> SEQ ID NO 19
<211> LENGTH: 22
<212> TYPE: DNA
<213> ORGANISM: Artificial Sequence
<220> FEATURE:
<223> OTHER INFORMATION: Oligonucleotide

```
<400> SEQUENCE: 19
cgccagtggc gccgctggac gc                                              22

<210> SEQ ID NO 20
<211> LENGTH: 22
<212> TYPE: DNA
<213> ORGANISM: Artificial Sequence
<220> FEATURE:
<223> OTHER INFORMATION: Oligonucleotide

<400> SEQUENCE: 20
cgccggtggc gccgctggac gc                                              22

<210> SEQ ID NO 21
<211> LENGTH: 22
<212> TYPE: DNA
<213> ORGANISM: Artificial Sequence
<220> FEATURE:
<223> OTHER INFORMATION: Oligonucleotide

<400> SEQUENCE: 21
cgccggtggc gccgccggac gc                                              22

<210> SEQ ID NO 22
<211> LENGTH: 22
<212> TYPE: DNA
<213> ORGANISM: Artificial Sequence
<220> FEATURE:
<223> OTHER INFORMATION: Oligonucleotide

<400> SEQUENCE: 22
cgccggtggc gccgccgggc gc                                              22

<210> SEQ ID NO 23
<211> LENGTH: 22
<212> TYPE: DNA
<213> ORGANISM: Artificial Sequence
<220> FEATURE:
<223> OTHER INFORMATION: Oligonucleotide

<400> SEQUENCE: 23
cgccggcggc gccgccgggc gc                                              22

<210> SEQ ID NO 24
<211> LENGTH: 96
<212> TYPE: DNA
<213> ORGANISM: Artificial Sequence
<220> FEATURE:
<223> OTHER INFORMATION: Oligonucleotide

<400> SEQUENCE: 24
cgggcattcc tgaagctgac agcattcggg ccgagatgtc tcgctccgtg gccttagctg     60
tgctcgcgct actctctctt tctggcctgg aggcta                              96

<210> SEQ ID NO 25
<211> LENGTH: 21
<212> TYPE: DNA
<213> ORGANISM: Artificial Sequence
<220> FEATURE:
<223> OTHER INFORMATION: Oligonucleotide

<400> SEQUENCE: 25
gcattcctga agctgacagc a                                               21
```

```
<210> SEQ ID NO 26
<211> LENGTH: 24
<212> TYPE: DNA
<213> ORGANISM: Artificial Sequence
<220> FEATURE:
<223> OTHER INFORMATION: Oligonucleotide

<400> SEQUENCE: 26
gatgagagag aaagaccgga cctc                                              24

<210> SEQ ID NO 27
<211> LENGTH: 22
<212> TYPE: DNA
<213> ORGANISM: Artificial Sequence
<220> FEATURE:
<223> OTHER INFORMATION: Oligonucleotide

<400> SEQUENCE: 27
ccgtggcctt agctgtgctc gc                                                22

<210> SEQ ID NO 28
<211> LENGTH: 33
<212> TYPE: DNA
<213> ORGANISM: Artificial Sequence
<220> FEATURE:
<223> OTHER INFORMATION: Oligonucleotide

<400> SEQUENCE: 28
cgggcgatgt ctcgctccgt ggccttacgc ccg                                    33
```